(12) United States Patent
Waxman et al.

(10) Patent No.: US 6,207,648 B1
(45) Date of Patent: Mar. 27, 2001

(54) METHODS OF USING CYTOCHROME P450 REDUCTASE FOR THE ENHANCEMENT OF P450-BASED ANTI-CANCER GENE THERAPY

(75) Inventors: David J. Waxman, Newton, MA (US); Ling Chen, Blue Bell, PA (US)

(73) Assignee: Trustees of Boston University, Boston, MA (US)

(*) Notice: Subject to any disclaimer, the term of this patent is extended or adjusted under 35 U.S.C. 154(b) by 0 days.

(21) Appl. No.: 09/118,179

(22) Filed: Jul. 17, 1998

Related U.S. Application Data

(60) Provisional application No. 60/053,677, filed on Jul. 24, 1997.

(51) Int. Cl.$^7$ .......................... A01N 43/04; C12N 15/00; C12N 15/63; C07H 21/04

(52) U.S. Cl. .................. 514/44; 435/320.1; 435/455; 536/23.2; 536/23.4

(58) Field of Search .................. 514/44; 435/320.1, 435/455; 536/23.2, 23.4

(56) References Cited

U.S. PATENT DOCUMENTS

| | | | |
|---|---|---|---|
| 5,529,774 | 6/1996 | Barba et al. | 424/93.21 |
| 5,591,624 | 1/1997 | Barber et al. | 435/240.2 |
| 5,601,818 | 2/1997 | Freeman et al. | 424/93.21 |
| 5,631,236 | 5/1997 | Woo et al. | 514/44 |
| 5,670,488 | 9/1997 | Gregory et al. | 514/44 |
| 5,688,773 | 11/1997 | Chiocca et al. | 514/44 |
| 5,691,177 | 11/1997 | Guber et al. | 435/172.3 |
| 5,741,486 | 4/1998 | Pathak et al. | 424/93.21 |
| 5,756,283 | 5/1998 | Wilson et al. | 435/5 |
| 5,763,217 | 6/1998 | Cynader et al. | 435/69.1 |
| 5,763,242 | 6/1998 | Zhang et al. | 435/172.3 |
| 6,080,849 | * 6/2000 | Bermudes et al. | 536/23.7 |

FOREIGN PATENT DOCUMENTS

| | | |
|---|---|---|
| WO 95/06486 | 3/1995 | (WO) . |
| WO 00/14256 | 3/2000 | (WO) . |

OTHER PUBLICATIONS

Boyer, M., Oncology Research, vol. 9, p. 391–395, 1997.*
Bremner, J., Cancer and Metastasis Reviews, vol. 12, p. 177–193, 1993.*
Mastrangelo et al., Seminars in Oncology, vol. 23 (1), p. 4–21, 1996.*
Orkin et al., Report and Recommendations of the Panel to Assess the NIK investment in Research on Gene Therapy, 1995.*
Ram and Waxman, J Biol Chem, 267(5), p. 3294–3301, 1992.*
Honkakoski et al., Biochem J., 285(3), p. 979–983, 1992.*
Sampol et al., Biochemical and Biophysical Research Communications, 235(3), p. 557–561, 1997.*

Abdallah, B., et al., "Non–viral gene transfer: Applications in developmental biology and gene therapy," *Biol. Cell* 85:1–7 (1995).
Aghi, M., et al., "Synergistic Anticancer Effects of Ganciclovir/Thymidine Kinase and 5–Fluorocytosine/Cytosine Deaminase Gene Therapies," *J. Natl. Cancer Inst.* 90:370–380 (Mar. 1998).
Ali, M., et al., "The use of DNA viruses as vectors for gene therapy," *Gene Therapy* 1:367–384 (1994).
Ascenzioni, F., et al., "Mammalian artificial chromosomes–vectors for somatic gene therapy," *Cancer Letters* 118:135–142 (Oct. 1997).
Ayash, L.J., et al., "Cyclophosphamide Pharmacokinetics: Correlation with Cardiac Toxicity and Tumor Response," *J. Clin. Oncology* 10:995–1000 (1992).
Bargou, R.C., et al., "Overexpression of the Death–promoting Gene bax–α which is Downregulated in Breast Cancer Restores Sensitivity to Different Apoptotic Stimuli and Reduces Tumor Growth in SCID Mice," *J. Clin. Invest.* 97:2651–2659 (Jun. 1996).
Barker, M., et al., "Development of an Animal Brain Tumor Model and Its Response to Therapy with 1,3–Bis(2–chloroethyl)–1–nitrosurea," *Cancer Res.* 33:976–983 (1973).
Bartoszek, A. and C.R. Wolf, "Enhancement of Doxorubicin Toxicity Following Activation by NADPH Cytochrome P450 Reductase," *Biochem. Pharm.* 43:1449–1457 (1992).
Belcourt, M.F., et al., "Differential toxicity of mitomycin C and porfiromycin to aerobic and hypoxic Chinese hamster ovary cells overexpressing human NADPH:cytochrome c (p–450) reductase," *Proc. Natl. Acad. Sci. USA* 93:456–460 (Jan. 1996).
Belinsky, M. and A.K. Jaiswal, "NAD(P)H: Quinone oxidoreductase$_1$ (DT–diaphorase) expression in normal and tumor tissues," *Cancer and Metastasis Rev.* 12:103–117 (1993).
Benedetti, S., et al., "Limited Efficacy of the HSV–TK/GCV System for Gene Therapy of Malignant Gliomas and Perspectives for the Combined Transduction of the Interleukin–4 Gene," *Human Gene Therapy* 8:1345–1353 (Jul. 1997).
Bilbao, G., et al., "Adenoviral/retroviral vector chimeras: a novel strategy to achieve high–efficiency stable transduction in vivo," *FASEB J.* 11:624–634 (Jul. 1997).

(List continued on next page.)

Primary Examiner—Deborah J. Clark
Assistant Examiner—S L Chen
(74) *Attorney, Agent, or Firm*—Sterne, Kessler, Goldstein & Fox, P.L.L.C.

(57) ABSTRACT

Methods of killing neoplastic cells are provided. The invention relates to the use of NADPH-cytochrome P450 reductase (RED) gene transfer in combination with cytochrome P450 gene transfer to enhance the sensitivity of tumor cells to anti-cancer drugs that are activated by P450 enzymes. The use of bioreductive drugs that are activated by RED and/or cytochrome P450, in this paradigm, is also provided.

54 Claims, 34 Drawing Sheets

OTHER PUBLICATIONS

Bourrié, M., et al., "Cytochrome P450 Isoform Inhibitors as a Tool for the Investigation of Metabolic Reactions Catalyzed by Human Liver Microsomes," *J. Pharm. Exper. Ther.* 277:321–332 (Apr. 1996).

Boyd, M.R. and K.D. Paull, "Some Practical Considerations and Applications of the National Cancer Institute In Vitro Anticancer Drug Discovery Screen," *Drug Development Res.* 34:91–109 (1995).

Boyer, M.J., "Bioreductive Agents: A Clinical Update," *Oncology Res.* 9:391–395 (Jun. 1997).

Bremner, J.C.M., "Assessing the bioreductive effectiveness of the nitroimidazole RSU1069 and its prodrug RB6145: with particular reference to in vivo methods of evaluation," *Cancer and Metastasis Rev.* 12:177–193 (1993).

Brody, S.L. and R.G. Crystal, "Adenovirus–Mediated in Vivo Gene Transfer," *Ann. NY Acad. Sci.* 716:90–103 (1994).

Brown, J.M. and A.J. Giaccia, "The Unique Physiology of Solid Tumors: Opportunities (and Problems) for Cancer Therapy," *Cancer Res.* 58:1408–1416 (Apr. 1998).

Burns, J.C., et al., "Vesicular stomatitis virus G glycoprotein pseudotyped retroviral vectors: Concentration to very high titer and efficient gene transfer into mammalian and non-mammalian cells," *Proc. Natl. Acad. Sci. USA* 90:8033–8037 (1993).

Calos, M.P., "The potential of extrachromosomal replicating vectors for gene therapy," *Trends in Genetics* 12:463–466 (Nov. 1996).

Caruso, M., et al., "Regression of established macroscopic liver metastases after in situ transduction of a suicide gene," *Proc. Natl. Acad. Sci. USA* 90:7024–7028 (1993).

Cawley, G.F., et al., "Substrate–Dependent Competition of Different P450 Isozymes for Limiting NADPH–Cytochrome P450 Reductase," *Biochem.* 34:1244–1247 (1995).

Chang, T.K.H., et al., "The lithocholic acid 6β–hydroxylase cytochrome P–450, CYP 3A10, is an active catalyst of steroid–hormone 6β–hydroxylation," *Biochem. J.* 291:429–433 (1993).

Chang, T.K.H., et al., "Differential Activation of Cyclophosphamide and Ifosphamide by Cytochromes P–450 2B and 3A in Human Liver Microsomes," *Cancer Res.* 53:5629–5637 (1993).

Chang, T.K.H., et al., "Identification of the polymorphically expressed CYP2C19 and the wild–type CYP2C9–ILE$^{359}$ allele as low–$K_m$ catalysts of cyclophosphamide and ifosfamide activation," *Pharmacogenetics* 7:211–221 (Jun. 1997).

Chase, M., et al., "An oncolytic viral mutant that delivers the CYP2B1 transgene and augments cyclophosphamide chemotherapy," *Nature Biotech.* 16:444–448 (May 1998).

Chen, C–Y., et al., "Effect of Herpes Simplex Virus Thymidine Kinase Expression Levels on Ganciclovir–Mediated Cytotoxicity and the "Bystander Effect"," *Human Gene Therapy* 6:1467–1476 (1995).

Chen, L. and D.J. Waxman, "Intratumoral Activation and Enhanced Chemotherapeutic Effect of Oxazaphosphorines following Cytochrome P–450 Gene Transfer: Development of a Combined Chemotherapy/Cancer Gene Therapy Strategy," *Cancer Res.* 55:581–589 (1995).

Chen, L., et al., "Sensitization of Human Breast Cancer Cells to Cyclophosphamide and Ifosfamide by Transfer of a Liver Cytochrome P450 Gene," *Cancer Res.* 56:1331–1340 (Mar. 1996).

Chen, L., et al., "Eradication of Murine Bladder Carcinoma by Intratumor Injection of a Bicistronic Adenoviral Vector Carrying cDNAs for the IL–12 Heterodimer and Its Inhibition by the IL–12 p40 Subunit Homodimer," *J. Immunology* 159:351–359 (Jul. 1997).

Chen, L., et al., "Potentiation of Cytochrome P450/Cyclophosphamide–based Cancer Gene Therapy by Coexpression of the P450 Reductase Gene," *Cancer Res.* 57:4830–4837 (Nov. 1997).

Chen, X., et al., "Cancer Gene Therapy by Direct Tumor Injections of a Nonviral T7 Vector Encoding a Thymidine Kinase Gene," *Human Gene Therapy* 9:729–736 (Mar. 1998).

Chirgwin, J.M., et al., "Isolation of Biologically Active Ribonucleic Acid from Sources Enriched in Ribonuclease," *Biochem.* 18:5294–5299 (1979).

Clarke, L. and D.J. Waxman, "Oxidative Metabolism of Cyclophosphamide: Identification of the Hepatic Monooxygenase Catalysts of Drug Activation," *Cancer Res.* 49:2344–2350 (1989).

Clary, B.M., et al., "Inhibition of established pancreatic cancers following specific active immunotherapy with interleukin–2 gene–transduced tumor cells," *Cancer Gene Therapy* 4:97–104 (Mar./Apr. 1997).

Connors, T.A., "The choice of prodrugs for gene directed enzyme prodrug therapy of cancer," *Gene Therapy* 2:702–709 (1995).

Culver, K.W., "Clinical Applications of Gene Therapy for Cancer," *Clin. Chem.* 40:510–512 (1994).

Dachs, G.U., et al., "Targeting gene expression to hypoxic tumor cells," *Nature Med.* 3:515–520 (May 1997).

Danos, O., "Construction of Retroviral Packaging Cell Lines," in: *Methods in Molecular Biology, vol. 8, Practical Molecular Virology: Viral Vectors for Gene Expression*, Collins, M.L.K., ed., The Humana Press,Inc., Clifton, NJ, pp. 17–27 (1991).

Dehal, S.S. and D. Kupfer, "CYP2D6 Catalyzes Tamoxifen 4–Hydroxylation in Human Liver," *Cancer Res.* 57:3402–3406 (Aug. 1997).

Deonarain, M.P., et al., "Genetic delivery of enzymes for cancer therapy," *Gene Therapy* 2:235–244 (1995).

Desoize, B. and J. Robert, "Individual Dose Adaptation of Anticancer Drugs," *Eur. J. Cancer* 30A:844–851 (1994).

Dornburg, R., "Reticuloendotheliosis viruses and derived vectors," *Gene Therapy* 2:301–310 (1995).

Drabek, D., et al., "The expression of bacterial nitroreductase in transgenic mice results in specific cell killing by the prodrug CB1954," *Gene Therapy* 4:93–100 (Feb. 1997).

Eck, S.L., et al., "Treatment of Advanced CNS Malignancies with the Recombinant Adenovirus H5.010RSVTK: A Phase I Trial," *Human Gene Therapy* 7:1465–1482 (Aug. 1996).

Edwards, R.J., et al., "Short Synthetic Peptides Exploited for Reliable and Specific Targeting of Antibodies to the C–Termini of Cytochrome P450 Enzymes," *Biochem. Pharm.* 49:39–47 (1995).

Elwell, J.H., et al., "Adaptation of Human Tumor Cells to Tirapazamine under Aerobic Conditions," *Biochem. Pharm.* 54:249–257 (Jul. 1997).

Ezzeddine, Z.D., et al., "Selective Killing of Glioma Cells in Culture and in Vivo by Retrovirus Transfer of the Herpes Simplex Virus Thymidine Kinase Gene," *New Biologist* 3:608–614 (1991).

Faber, O.K., et al., "The Effect of Chloramphenicol and Sulphaphenazole on the Biotransformation of Cyclophosphamide in Man," *Br. J. Clin. Pharm.* 2:281–285 (1975).

Feng, M., et al., "Stable in vivo gene transduction via a novel adenoviral/retroviral chimeric vector," *Nature Biotech.* 15:866–870 (Sep. 1997).

Fisher, C.W., et al., "High–level expression in *Escherichia coli* of enzymatically active fusion proteins containing the domains of mammalian cytochromes P450 and NADPH–P450 reductase flavoprotein," *Proc. Natl. Acad. Sci. USA* 89:10817–10821 (1992).

Fisher, C.W.A., et al., "Construction of Plasmids and Expression in *Escherichia coli* of Enzymatically Active Fusion Proteins Containing the Heme–Domain of a P450 Linked to NADPH–P450 Reductase," *Methods Enzymology* 272:15–25 (Sep. 1996).

Fitzsimmons, S.A., et al., "Reductase Enzyme Expression Across the National Cancer Institute Tumor Cell Line Panel: Correlation with Sensitivity to Mitomycin C and E09," *J. Natl. Cancer Inst.* 88:259–269 (Mar. 1996).

Fleming, R.A., "An Overview of Cyclophosphamide and Ifosfamide Pharmacology," *Pharmacotherapy* 17:146S–154S (Sep.–Oct. 1997).

Flotte, T.R. and B.J. Carter, "Adeno–associated virus vectors for gene therapy," *Gene Therapy* 2:357–362 (1995).

Foster, J.R., et al., "Induction of Drug–Metabolizing Enzymes in Human Pancreatic Cancer and Chronic Pancreatitis," *J. Path.* 169:457–463 (1993).

Freeman, S.M., et al., "The "Bystander Effect": Tumor Regression when a Fraction of the Tumor Mass is Genetically Modified," *Cancer Res.* 53:5274–5283 (1993).

Freeman, S.M., et al. "In Situ Use of Suicide Genes for Cancer Therapy," *Seminars Oncology* 23:31–45 (Feb. 1996).

Friedlos, F., et al., "Mustard Prodrugs for Activation by *Escherichia coli* Nitroreductase in Gene–Directed Enzyme Prodrug Therapy," *J. Med. Chem.* 40:1270–1275 (Apr. 1997).

Furuya, H., et al., "Polymerase Chain Reaction–Directed Identification, Cloning, and Quantification of Human CYP2C18 mRNA," *Molec. Pharm.* 40:375–382 (1991).

Gagandeep, S., et al., Prodrug–activated gene therapy: Involvement of an immunological component in the "bystander effect," *Cancer Gene Therapy* 3:83–88 (Mar./Apr. 1996).

Ghattas, I.R., et al., "The Encephalomyocarditis Virus Internal Ribosome Entry Site Allows Efficient Coexpression of Two Genes from a Recombinant Provirus in Cultured Cells and in Embryos," *Molec. Cell. Biol.* 11:5848–5859 (1991).

Goeptar, A.R., et al., "Cytochrome P450 2B1–Mediated One–Electron Reduction of Adriamycin: A Study with Rat Liver Microsomes and Purified Enzymes," *Molec. Pharm.* 44:1267–1277 (1993).

Goeptar, A.R., et al., "Cytotoxicity of Mitomycin C and Adriamycin in Freshly Isolated Rat Hepatocytes: The Role of Cytochrome P450," *Cancer Res.* 54:2411–2418 (1994).

Goeptar, A.R., et al., "Oxygen and Xenobiotic Reductase Activities of Cytochrome P450," *Crit. Rev. Toxicology* 25:25–65 (1995).

Goldstein, J.A. and S.M.F. de Morais, "Biochemistry and molecular biology of the human CYP2C subfamily," *Pharmacogenetics* 4:285–299 (1994).

Gonzalez, F.J. and C.B. Kasper, "Sequential Translocation of Two Phenobarbital–Induced Polysomal Messenger Ribonucleic Acids from the Nuclear Envelope to the Endoplasmic Reticulum," *Biochem.* 20:2292–2298 (1981).

Goren, M.P., et al., "Dechloroethylation of Ifosfamide and Neurotoxicity," *The Lancet II*:1219–1220 (1986).

Graham, F.L. and L. Prevec, "Manipulation of Adenovirus Vectors," in: *Methods in Molecular Biology, vol. 7: Gene Transfer and Expression Protocols*, Murray, E.J., ed., The Humana Press, Inc., Clifton, NJ, pp. 109–128 (1991).

Graham, M.A., et al., "Drug Metabolism in Carcinogenesis and Cancer Chemotherapy," *Pharmaco. Ther.* 51:275–289 (1991).

Graham, M.A., et al., "Pharmacokinetics of the hypoxic cell cytotoxic agent tirapazamine and its major bioreductive metabolites in mice and humans: retrospective analysis of a pharmacokinetically guided dose–escalation strategy in a phase I trial," *Cancer Chemother. Pharmacol.* 40:1–10 (May 1997).

Grant, R. and J.W. Ironside, "Glutathione S–transferases and cytochrome P450 detoxifying enzyme distribution in human cerebral glioma," *J. Neuro–Oncology* 25:1–7 (1995).

Green, N.K., et al., "Sensitization of colorectal and pancreatic cancer cell lines to the prodrug 5–(aziridin–1–yl)–2, 4–dinitrobenzamide (CB1954) by retroviral transduction and expression of the *E. coli* nitroreductase gene," *Cancer Gene Therapy* 4:229–238 (Jul.–Aug. 1997).

Günzburg, W.H., et al., "Regulated Gene Expression after Retroviral Vector–Mediated Delivery of Cancer–Relevant Therapeutic Genes," *Recent Results in Cancer Res.*144:116–126 (Sep. 1998).

Gurney, H., "Dose Calculation of Anticancer Drugs: A Review of the Current Practice and Introduction of an Alternative," *J. Clin. Oncology* 14:2590–2611 (Sep. 1996).

Halpert, J.R., et al., "Contemporary Issues in Toxicology: Selective Inhibitors of Cytochromes P450," *Toxicol. Applied Pharm.* 125:163–175 (1994).

Harris, M.P., et al., "Adenovirus–mediated p53 gene transfer inhibits growth of human tumor cells expressing mutant p53 protein," *Cancer Gene Therapy* 3:121–130 (Mar.–Apr. 1996).

He, Y.A., et al., "Identification of Three Key Residues in Substrate Recognition Site 5 of Human Cytochrome P450 3A4 by Cassette and Site–Directed Mutagenesis," *Biochem.* 36:8831–8839 (Jul. 1997).

Heise, C., et al., "ONYX–015, an E1B gene–attenuated adenovirus, causes tumor–specific cytolysis and antitumoral efficacy that can be augmented by standard chemotherapeutic agents," *Nature Med.* 3:639–645 (Jun. 1997).

Hofmann, A., et al., "Rapid retroviral delivery of tetracycline–inducible genes in a single autoregulatory cassette," *Proc. Natl. Acad. Sci. USA* 93:5185–5190 (May 1996).

Hubbard, S.M. and J.F. Jenkins, "Chemotherapy Administration: Practical Guidelines," in: *Cancer Chemotherapy: Principles and Practice*, Chabner, B.A. and J.M. Collins, eds., J.B. Lippincott, Inc., Philadelphia, PA, pp. 449–464 (1990).

Huber, B.E., et al., "In Vivo Antitumor Activity of 5–Fluorocytosine on Human Colorectal Carcinoma Cells Genetically Modified to Express Cytosine Deaminase," *Cancer Res.* 53:4619–4626.

Hwang, J.-J., et al., "Novel Retroviral Vector Transferring a Suicide Gene and a Selectable Marker Gene with Enhanced Gene Expression by Using a Tetracycline–Responsive Expression System," *J. Virology* 70:8138–8141 (Nov. 1996).

Jacoby, D.R., et al., "Hybrid vectors: a new generation of virus–based vectors designed to control the cellular fate of delivered genes," *Gene Therapy* 4:1281–1283 (Dec. 1997).

Jones, G.D.D. and M. Weinfeld, "Dual Action of Tirapazamine in the Induction of DNA Strand Breaks," *Cancer Res.* 56:1584–1590 (Apr. 1996).

Kaijser, G.P., et al., "The Analysis of Ifosfamide and its Metabolites (Review)," *Anticancer Res.* 13:1311–1324 (1993).

Kaptein, L.C.M., et al., "Optimized conditions for the production of recombinant amphotropic retroviral vector preparations," *Gene Therapy* 4:172–176 (Feb. 1997).

Kivistö, K.T., et al., "The role of human cytochrome P450 enzymes in the metabolism of anticancer agents: implications for drug interactions," *Br. J. Clin. Pharm.* 40:523–530 (1995).

Kondo, S., et al., "Retroviral Transfer of CPP32β Gene into Malignant Gliomas in Vitro and in Vivo," *Cancer Res.* 58:962–967 (Mar. 1998).

Kotani, H., et al., "Improved Methods of Retroviral Vector Transduction and Production for Gene Therapy," *Human Gene Therapy* 5:19–28 (1994).

Kramm, C.M., et al., "Gene Therapy for Brain Tumors," *Brain Path.* 5:345–381 (1995).

Kukowska–Latallo, J.F., et al., "Efficient transfer of genetic material into mammalian cells using Starburst polyamidoamine dendrimers," *Proc. Natl. Acad. Sci. USA* 93:4897–4902 (May 1996).

Kurowski, V. and T. Wagner, "Comparative pharmacokinetics of ifosfamide, 4–hydroxyifosfamide, chloroacetaldehyde, and 2– and 3–dechloroethylifosfamide in patients on fractionated intravenous ifosfamide therapy," *Cancer Chemother. Pharmacol.* 33:36–42 (1993).

Lan, K.-H., et al., "In Vivo Selective Gene Expression and Therapy Mediated by Adenoviral Vectors for Human Carcinoembryonic Antigen–producing Gastric Carcinoma," *Cancer Res.* 57:4279–4284 (Oct. 1997).

Lartigau, E. and M. Guichard, "The effect of tirapazamine (SR–4233) alone or combined with chemotherapeutic agents on xenografted human tumours," *Br. J. Cancer* 73:1480–1485 (Jun. 1996).

Latchman, D.S., "Herpes Simplex Virus Vectors for Gene Therapy," *Molec. Biotech.* 2:179–195 (1994).

Le Blanc, G.A. and D.J. Waxman, "Interaction of Anticancer Drugs with Hepatic Monooxygenase Enzymes," *Drug Metabolism Reviews* 20:395–439 (1989).

Lee, R.J. and L. Huang, "Lipidic Vector Systems for Gene Transfer," *Crit. Rev. Ther. Drug Carrier Systems* 14:173–206 (Apr. 1997).

Lemaire, P. and D.R. Livingstone, "Inhibition Studies on the Involvement of Flavoprotein Reductases in Menadione–and Nitrofurantoin–Stimulated Oxyradical Production by Hepatic Microsomes of Flounder (*Platichthys flesus*)," *J. Biochem. Toxicol.* 9:87–95 (1994).

Link, C.J., et al., "A Phase I Trial of In Vivo Gene Therapy with the Herpes Simplex Thymidine Kinase/Ganciclovir System for the Treatment of Refractory or Recurrent Ovarian Cancer," *Human Gene Therapy* 7:1161–1179 (Jun. 1996).

Manome, Y., et al., "Gene therapy for malignant gliomas using replication incompetent retroviral and adenoviral vectors encoding the cytochrome P450 2B1 gene together with cyclophosphamide," *Gene Therapy* 3:513–520 (Jun. 1996).

Marais, R., et al., "Gene–directed Enzyme Prodrug Therapy with a Mustard Prodrug/Carboxypeptidase G2 Combination," *Cancer Res.* 56:4735–4742 (Oct. 1996).

Massie, B., et al., "Inducible Overexpression of a Toxic Protein by an Adenovirus Vector with a Tetracycline–Regulatable Expression Cassette," *J. Virology* 72:2289–2296 (Mar. 1998).

McGuire, J.J., et al., "Inhibition of the Biotransformation and Pharmacological Actions of Glyceryl Trinitrate by the Flavoprotein Inhibitor, Diphenyleneiodonium Sulfate," *J. Pharm. Exper. Ther.* 271:708–714 (1994).

Meschter, C.L., et al., "A 13–Week Toxicologic and Pathologic Evaluation of Prolonged Cytochromes P450 Inhibition by 1–Aminobenzotriazole in Male Rats," *Fundamental Applied Toxicol.* 22:369–381 (1994).

Mesnil, M., et al., "Bystander killing of cancer cells by herpes simplex virus thymidine kinase gene is mediated by connexins," *Proc. Natl. Acad. Sci. USA* 93:1831–1835 (Mar. 1996).

Miller, A.D., "Retrovirus Packaging Cells," *Human Gene Therapy* 1:5–14 (1990).

Miller, N. and J. Whelan, "Progress in Transcriptionally Targeted and Regulatable Vectors for Genetic Therapy," *Human Gene Therapy* 8:803–815 (May 1997).

Miwa, G.T., et al., "Studies on the Rate–Limiting Enzyme Component in the Microsomal Monooxygenase System," *J. Biol. Chem.* 253:1921–1929 (1978).

Moolten, F.L. and J.M. Wells, "Curability of Tumors Bearing Herpes Thymidine Kinase Genes Transfered by Retroviral Vectors," *J. Natl. Cancer Institute* 82:297–300 (1990).

Moolten, F.L., "Drug sensitivity ("suicide") genes for selective cancer chemotherapy," *Cancer Gene Therapy* 1:279–287 (1994).

Morgan, R.A., et al., "Retroviral vectors containing putative internal ribosome entry sites: development of a polycistronic gene transfer system and applications to human gene therapy," *Nucleic Acids Res.* 20:1293–1299 (1992).

Morgenstern, J.P. and H. Land, "Advanced mammalian gene transfer: high titre retroviral vectors with multiple drug selection markers and a complementary helper–free packaging cell line," *Nucleic Acids Res.* 18:3587–3596 (1990).

Mullen, C.A., et al., "Transfer of the bacterial gene for cytosine deaminase to mammalian cells confers lethal sensitivity to 5–fluorocytosine: A negative selection system," *Proc. Natl. Acad. Sci. USA* 89:33–37 (1992).

Mullen, C.A., et al., "Tumors Expressing the Cytosine Deaminase Suicide Gene Can Be Eliminated in Vivo with 5–Fluorocytosine and Induce Protective Immunity to Wild Type Tumor," *Cancer Res.* 54:1503–1506 (1994).

Murdoch, B., et al., "A rapid screening procedure for the identification of high–titer retrovirus packaging clones," *Gene Therapy* 4:744–749 (Jul. 1997).

Nakanishi, M., "Gene Introduction into Animal Tissues," *Crit. Rev. Ther. Drug Carrier Systems* 12:263–310 (1995).

Naldini, L., et al., "In Vivo Gene Delivery and Stable Transduction of Nondividing Cells by a Lentiviral Vector," *Science* 272:263–267 (Apr. 1996).

Nelson, D.R., et al., "P450 superfamily: update on new sequences, gene mapping, accession numbers and nomenclature," *Pharmacogenetics* 6:1–42 (Feb. 1996).

Newton, D.J., et al., "Cytochrome P450 Inhibitors: Evaluation of Specificities in the In Vitro Metabolism of Therapeutic Agents by Human Liver Microsomes," *Drug Metabolism and Disposition* 23:154–158 (1995).

Ng, S.–F. And D.J. Waxman, "Activation of thio–TEPA cytotoxicity toward human breast cancer cells by hepatic cytochrome P450," *Intl. J. Oncology* 2:731–738 (1993).

Ohno, K. and D. Meruelo, "Multi–Drug Delivery System Using Streptavidin–Transforming Growth Factor–α Chimeric Protein," *DNA and Cell Biol.* 15:401–406 (May 1996).

Ohno, K., et al., "Cell–Specific, Multidrug Delivery System Using Streptavidin–Protein A Fusion Protein," *Biochem. Molec. Med.* 58:227–233 (Aug. 1996).

Ojeifo, J.O., et al., "Towards endothelial–cell–directed cancer immunotherapy: in vitro expression of human recombinant cytokine genes by human and mouse primary endothelial cells," *Cytokines and Molecular Therapy* 2:89–101 (Jun. 1996).

Oldfield, E.H., et al., "Gene Therapy for the Treatment of Brain Tumors Using Intra–Tumoral Transduction with the Thymidine Kinase Gene and Intravenous Ganciclovir," *Human Gene Therapy* 4:39–69 (1993).

O'Leary, K.A., et al., "NADPH Cytochrome P–450 Oxidoreductase Gene: Identification and Characterization of the Promoter Region," *Arch. Biochem. Biophys.* 310:452–459 (1994).

O'Malley,Jr., B.W., et al., "Combination Gene Therapy for Oral Cancer in a Murine Model," *Cancer Res.* 56:1737–1741 (Apr. 1996).

O'Malley,Jr., B.W. and D. Li, "Combination Gene Therapy for Salivary Gland Cancer," *Annals NY Acad. Sci.* 842:163–170 (Apr. 1998).

Onodera, M., et al., "A Simple and Reliable Method for Screening Retroviral Producer Clones Without Selectable Markers," *Human Gene Therapy* 8:1189–1194 (Jul. 1997).

O'Rourke, J.F., et al., "Hypoxia Response Elements," *Oncology Res.* 9:327–332 (Jun. 1997).

Paine–Murrieta, G.D., et al., "Human tumor models in the severe combined immune deficient (scid) mouse," *Cancer Chemother. Pharmacol.* 40:209–214 (Jun. 1997).

Patterson, A.V., et al., "Importance of P450 reductase activity in determining sensitivity of breast tumour cells to the bioreductive drug, tirapazimine (SR 4233)," *Br. J. Cancer* 72:1144–1150 (1995).

Patterson, A.V., et al., "Novel gene therapy approaches to targeting reductive enzyme expression to regions of tumor hypoxia," *Proc. Am. Assoc. Cancer Res.* 37:340–341, Abstract No. 2323 (Mar. 1996).

Patterson, A.V., et al., "Overexpression of human NADPH: cytochrome c (P450) reductase confers enhanced sensitivity to both tirapazamine (SR 4233) and RSU 1069," *Br. J. Cancer* 76:1338–1347 (May 1997).

Patterson, L.H., "Rationale for the use of aliphatic N–oxides of cytotoxic anthraquinones as prodrug DNA binding agents: a new class of bioreductive agent," *Cancer Metastasis Rev.* 12:119–134 (1993).

Pawelek, J.M., et al., "Tumor–targeted Salmonella as a Novel Anticancer Vector," *Cancer Res.* 57:4537–4544 (Oct. 1997).

Pear, W.S., et al., "Production of high–titer helper–free retroviruses by transient transfection," *Proc. Natl. Acad. Sci. USA* 90:8392–8396 (1993).

Peters, W.P., et al., "High–Dose Chemotherapy and Autologous Bone Marrow Support as Consolidation After Standard–Dose Adjuvant Therapy for High–Risk Primary Breast Cancer," *J. Clin. Oncol.* 11:1132–1143 (1993).

Phillips, A.H. and R.C. Langdon, "Hepatic Triphosphopyridine Nucleotide–Cytochrome C Reductase: Isolation, Characterization, and Kinetic Studies," *J. Biol. Chem.* 237:2652–2660 (1962).

Phillips, S.C., "Receptor–mediated DNA Delivery Approaches to Human Gene Therapy," *Biologicals* 23:13–16 (1995).

Pope, I.M., et al., "The Role of the Bystander Effect in Suicide Gene Therapy," *Eur. J. Cancer* 33:1005–1016 (Jun. 1997).

Porter, T.D., et al., "NADPH–Cytochrome P–450 Oxidoreductase Gene Organization Correlates with Structural Domains of the Protein," *Biochem.* 29:9814–9818 (1990).

Porter, T.D., "An unusual yet strongly conserved flavoprotein reductase in bacteria and mammals," *TIBS* 16:154–158 (1991).

Rainov, N.G., et al., "Retrovirus–mediated gene therapy of experimental brain neoplasms using the herpes simplex virus–thymidine kinase/ganciclovir paradigm," *Cancer Gene Therapy* 3:99–106 (Mar.–Apr. 1996).

Rainov, N.G., et al., "New Prodrug Activation Gene Therpay for Cancer Using Cytochrome P450 4B1 and 2–Aminoanthracene/4–Ipomeanol," *Human Gene Therapy* 9:1261–1273 (Jun. 1998).

Rancourt, C., et al., "Endothelial Cell Vehicles for Delivery of Cytotoxic Genes as a Gene Therapy Approach for Carcinoma of the Ovary," *Clin. Cancer Res.* 4:265–270 (Feb. 1998).

Ram, P.A. and D.J. Waxman, "Thyroid Hormone Stimulation of NADPH P450 Reductase Expression in Liver and Extrahepatic Tissues," *J. Biol. Chem.* 267:3294–3301 (1992).

Ram, Z., et al., "In Situ Retroviral–mediated Gene transfer for the Treatment of Brain Tumors in Rats," *Cancer Res.* 53:83–88 (1993).

Ram, Z., et al., "Toxicity studies of retroviral–mediated gene transfer for the treatment of brain tumors," *J. Neurosurg.* 79:400–407 (1993).

Rauth, A.M., et al., "Cellular approaches to bioreductive drug mechanisms," *Cancer Metastasis Rev.* 12:153–164 (1993).

Ren, S., et al., "Oxidation of Cyclophosphamide to 4–Hydroxycyclophosphamide and Deschloroethylcyclophosphamide in Human Liver Microsomes," *Cancer Res.* 57:4229–4235 (Oct. 1997).

Riley, R.J., et al., "Initial Characterization of the Major Mouse Cytochrome P450 Enzymes Involved in the Reductive Metabolism of the Hypoxic Cytoxin 3–Amino–1, 2,4–Benzotriazine–1,4–Di–N–Oxide (Tirapazamine, SR 4233, WIN 59075)," *Biochem. Pharm.* 45:1065–1077 (1993).

Robbins, P.D., et al., "Viral vectors for gene therapy," *TIBTECH* 16:35–40 (Jan. 1998).

Rogulski, K.R., et al., "Glioma Cells Transduced with an *Escherichia coli* CD/HSV–1 TK Fusion Gene Exhibit Enhanced Metabolic Suicide and Radiosensitivity," *Human Gene Therapy* 8:73–85 (Jan. 1997).

Rosenfeld, M.E. and D.T. Curiel, "Gene therapy strategies for novel cancer therapeutics," *Current Opinion Oncology* 8:72–77 (Jan. 1996).

Roth, J.A., et al., "Retrovirus–mediated wild–type p53 gene transfer to tumors of patients with lung cancer," *Nature Med.* 2:985–991 (Sep. 1996).

Roth, J.A. and R.J. Cristiano, "Gene Therapy for Cancer: What Have We Done and Where Are We Going?," *J. Natl. Cancer Institute* 89:21–39 (Jan. 1997).

Sawamura, A.O., et al., "Transfection of Human Cytochrome P–450 Reductase cDNA and Its Effect on the Sensitivity to Toxins," *Oncology* 53:406–411 (Sep.–Oct. 1996).

Schneider, A., "Stable Expression of Human Cytochrome P450 3A4 in Conjunction with Human NADPH–Cytochrome P450 Oxidoreductase in V79 Chinese Hamster Cells," *Arch. Biochem. Biophys.* 332:295–304 (Aug. 1996).

Schnierle, B.S. and B. Groner, "Retroviral targeted delivery," *Gene Therapy* 3:1069–1073 (Dec. 1996).

Scudiero, D.A., et al., "Evaluation of a Soluble Tetrazolium/Formazan Assay for Cell Growth and Drug Sensitivity in Culture Using Human and Other Tumor Cell Lines," *Cancer Res.* 48:4827–4833 (1988).

Shaughnessy, E., et al., "Parvoviral Vectors for the Gene Therapy of Cancer," *Seminars Oncology* 23:159–171 (Feb. 1996).

Shephard, E.A., et al., "Quantification of Cytochrome P450 Reductase Gene Expression in Human Tissues," *Arch. Biochem. Biophys.* 294:168–172 (1992).

Shet, M.S., et al., "Human cytochrome P450 3A4: Enzymatic properties of a purified recombinant fusion protein containing NADPH–P450 reductase," *Proc. Natl. Acad. Sci. USA* 90:11748–11752 (1993).

Shimada, T., et al., "Interindividual Variations in Human Liver Cytochrome P–450 Enzymes Involved in the Oxidation of Drugs, Carcinogens and Toxic Chemicals: Studies with Liver Microsomes of 30 Japanese and 30 Caucasians," *J. Pharm. Exper. Ther.* 270:414–423 (1994).

Short, M.P., et al., "Gene Delivery to Glioma Cells in Rat Brain by Grafting of a Retrovirus Packaging Cell Line," *J. Neurosci. Res.* 27:427–439 (1990).

Siemann, D.W., "The in situ tumour response to combinations of cyclophosphamide and tirapazamine," *Br. J. Cancer* 74:S65–S69 (Jul. 1996).

Siim, B.G. et al., "Tirapazamine–induced DNA damage measured using the comet assay correlates with cytotoxicity towards hypoxic tumour cells in vitro," *Br. J. Cancer* 73:952–960 (Apr. 1996).

Sladek, N.E., "Metabolism of Oxazaphosphorines," *Pharm. Ther.* 37:301–355 (1988).

Smiley, W.R., et al., "Establishment of Parameters for Optimal Transduction Efficiency and Antitumor Effects with Purified High–Titer HSV–TK Retroviral Vector in Established Solid Tumors," *Human Gene Therapy* 8:965–977 (May 1997).

Smith, G., et al., "Regulation of cytochrome P450 gene expression in human colon and breast tumour xenografts," *Br. J. Cancer* 68:57–63 (1993).

Strobel, H.W., et al., "NADPH Cytochrome P450 Reductase and Its Structural and Functional Domains," in: *Cytochrome P450: Structure, Mechanism, and Biochemistry*, Ortiz de Montellano, P.R., ed., Plenum Press, NY, pp. 225–244 (1995).

Struck, R.F., et al., "Plasma Pharmacokinetics of Cyclophosphamide and Its Cytotoxic Metabolites after Intravenous versus Oral Administration in a Randomized, Crossover Trial," *Cancer Res.* 47:2723–2726 (1987).

Szklarz, G.D., et al., "Site–Directed Mutagenesis as a Tool for Molecular Modeling of Cytochrome P450 2B1," *Biochem.* 34:14312–14322 (1995).

Tahara, H., et al., "Effective Eradication of Established Murine Tumors with IL–12 Gene Therapy Using a Polycistronic Retroviral Vector," *J. Immunol.* 154:6466–6474 (1995).

Tang, M.X., et al., "In Vitro Gene Delivery by Degraded Polyamidoamine Dendrimers," *Bioconjugate Chem.* 7:703–714 (Nov.–Dec. 1996).

Tapscott, S.J., et al., "Gene therapy of rat 9L gliosarcoma tumors by transduction with selectable genes does not require drug selection," *Proc. Natl. Acad. Sci. USA* 91:8185–8189 (1994).

Thigpen, T., "Editorial," *Gynecologic Oncol.* 42:191–192 (1991).

Tos, A.G., et al., "Retroviral Vector–Mediated Transfer of the Tumor Necrosis Factor α Gene Into Human Cancer Cells Restores an Apoptotic Cell Death Program and Induces a Bystander–Killing Effect," *Blood* 87:2486–2495 (Mar. 1996).

Uckert, W., et al., "Double Suicide Gene (Cytosine Deaminase and Herpes Simplex Virus Thymidine Kinase) but Not Single Gene Transfer Allows Reliable Elimination of Tumor Cells In Vivo," *Human Gene Therapy* 9:855–865 (Apr. 1998).

van Maanen, J.M.S., et al., "Cytochrome P–450–mediated O–Demethylation: A Route in the Metabolic Activation of Etoposide (VP–16–213)," *Cancer Res.* 47:4658–4662 (1987).

van Warmerdam, L.J.C., "Tailor–made chemotherapy for cancer patients," *Netherlands J. Med.* 51:30–35 (Jul. 1997).

Vermilion, J.L., et al., "Separate Roles for FMN and FAD in Catalysis by Liver Microsomal NADPH–cytochrome P–450 Reductase," *J. Biol. Chem.* 256:266–277 (1981).

Vile, R.G., "Tumor–specific gene expression," *Seminars Cancer Biology* 5:429–436 (1994).

Vile, R.G. and S.J. Russell, "Retroviruses as vectors," *Br. Med. Bulletin* 51:12–30 (1995).

von Rüden, T., et al., "Generation of High–Titer Retroviral Vectors Following Receptor–Mediated, Adenovirus–Augmented Transfection," *BioTechniques* 18:484–489 (1995).

Walker, D., et al., "Identification of the Major Human Hepatic Cytochrome P450 Involved in Activation and N–Dechloroethylation of Ifosfamide," *Biochem. Pharm.* 47:1157–1163 (1994).

Walther, W. and U. Stein, "Cell type specific and inducible promoters for vectors in gene therapy as an approach for cell targeting," *J. Mol. Med.* 74:379–392 (Jul. 1996).

Watson, J.D., et al., "Working Toward Human Gene Therapy," in: *Recombinant DNA*, $2^{nd}$ edition, W.H. Freeman, Inc., NY, pp. 567–581 (1992).

Waxman, D.J. and C. Walsh, "Phenobarbital–induced Rat Liver Cytochrome P–450: Purification and Characterization of Two Closely Related Isozymic Forms," *J. Biol. Chem.* 257:10446–10457 (1982).

Waxman, D.J., et al., "Regulation of Rat Hepatic Cytochrome P–450: Age–Dependent Expression, Hormonal Imprinting, and Xenobiotic Inducibility of Sex–Specific Isoenzymes," *Biochem.* 24:4409–4417 (1985).

Waxman, D.J., et al., "Hypophysectomy Differentially Alters P–450 Protein Levels and Enzyme Activities in Rat Liver: Pituitary Control of Hepatic NADPH Cytochrome P–450 Reductase," *Molec. Pharm.* 35:519–525 (1989).

Waxman, D.J., "Rat Hepatic P450IIA and P450IIC Subfamily Expression Using Catalytic, Immunochemical, and Molecular Probes," *Methods Enzymology* 206:249–267 (1991).

Weber, G.F. and D.J. Waxman, "Activation of the Anti–Cancer Drug Ifosphamide by Rat Liver Microsomal P450 Enzymes," *Biochem. Pharm.* 45:1685–1694 (1993).

Wei, M.X., et al., "Experimental Tumor Therapy in Mice Using the Cyclophosphamide–Activating Cytochrome P450 2B1 Gene," *Human Gene Therapy* 5:969–978 (1994).

Wilson, J.M., "Vectors–shuttle vehicles for gene therapy," *Clin. Exp. Immunol.* 107:31–32 (Jan. 1997).

Workman, P. and I.J. Stratford, "The experimental development of bioreductive drugs and their role in cancer therapy," *Cancer Metastasis Rev.* 12:73–82 (1993).

Wyman, T.B., et al., "Design, Synthesis, and Characterization of a Cationic Peptide that Binds to Nucleic Acids and Permeabilizes Bilayers," *Biochem.* 36:3008–3017 (Mar. 1997).

Yabusaki, Y., "Artificial P450/reductase fusion enzymes: What can we learn from their structures?" *Biochimie* 77:594–603 (1995).

Yamano, S., et al., "Human NADPH–P450 Oxidoreductase: Complementary DNA Cloning, Sequence and Vaccinia Virus–Mediated Expression and Localization of the CYPOR Gene to Chromosome 7," *Molec. Pharm.* 35:83–88 (1989).

Yu, J.S., et al., "Retroviral Delivery and Tetracycline–dependent Expression of IL–1β–converting Enzyme (ICE) in a Rat Glioma Model Provides Controlled Induction of Apoptotic Death in Tumor Cells," *Cancer Res.* 56:5423–5427 (Dec. 1996).

Zhang, J. and S.J. Russell, "Vectors for cancer gene therapy," *Cancer Metastasis Rev.* 15:385–401 (Sep. 1996).

Zufferey, R., et al., "Multiply attenuated lentiviral vector achieves efficient gene delivery in vivo," *Nature Biotech.* 15:871–875 (Sep. 1997).x

* cited by examiner

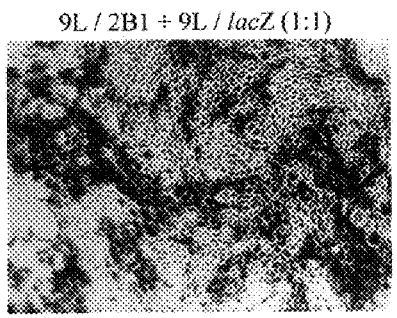
FIG.6A  9L / 2B1 + 9L / lacZ (1:1)
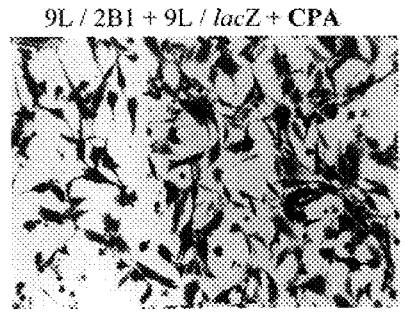
FIG.6B  9L / 2B1 + 9L / lacZ + CPA
FIG.6C  9L / 2B1 / RED + 9L / lacZ (1:1)
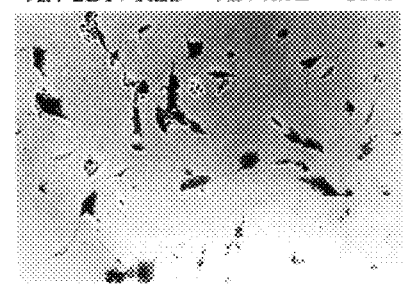
FIG.6D  9L / 2B1 / RED + 9L / lacZ + CPA

CYP2B6

CYP2Cs

METHODS OF USING CYTOCHROME P450 REDUCTASE FOR THE ENHANCEMENT OF P450-BASED ANTI-CANCER GENE THERAPY

CROSS REFERENCE TO RELATED APPLICATIONS

This application claims the benefit of U.S. Provisional application Ser. No. No. 60/053,677, filed Jul. 24, 1997, which is herein incorporated by reference.

STATEMENT AS TO RIGHTS TO INVENTIONS MADE UNDER FEDERALLY-SPONSORED RESEARCH AND DEVELOPMENT

The U.S. Government has a paid-up license in this invention and the right in limited circumstances to require the patent owner to license others on reasonable terms as provided for by the terms of grant number CA49248, awarded by the National Institutes of Health.

BACKGROUND OF THE INVENTION

1. Field of the Invention

The present invention is directed to the killing of neoplastic cells. More specifically, the present invention relates to the use of NADPH cytochrome P450 reductase (RED) to enhance cytochrome P450-based anti-cancer gene therapy.

2. Related Art

Traditional methods for cancer treatment rely on a combination of surgery, radiation, and cytotoxic chemotherapeutic drugs. Although the treatment of tumor cells with cytotoxic chemicals is well known in the art, presently, the therapeutic activity of many cytotoxic anti-cancer drugs is limited by a moderate therapeutic index associated with nonspecific toxicity toward normal host tissues, such as bone marrow, and the emergence of drug-resistant tumor cell sub-populations. One novel approach to enhancing the selectivity of cancer chemotherapeutics, and thereby reducing the toxicity of treatment, involves the application of gene therapy technologies to cancer treatment. See, Roth, J. A. and Cristiano, R. J., *J. Natl. Cancer Inst.* 89:21–39(1997); Rosenfeld, M. E. and Curiel, D. T., *Curr. Opin. Oncol.* 8:72–77 (1996).

In one such therapy known in the art, the phenotype of the target tumor cells is genetically altered to increase the tumors drug sensitivity and responsiveness. One promising strategy involves directly transferring a "chemosensitization" or "suicide" gene encoding a prodrug activation enzyme to malignant cells, in order to confer sensitivity to otherwise innocuous agents (Moolten, F. L., *Cancer Gene Therapy* 1:279–287 (1994); Freeman, S. M., et al., *Semin. Oncol.* 23:31–45 (1996); Deonarain, M. P., et al., *Gene Therapy* 2: 235–244 (1995)).

Several prodrug activation genes have been studied for application in cancer gene therapy. In one example, herpes simplex virus thymidine kinase (HSV-TK) in combination with the prodrug ganciclovir represents a prototypic prodrug/enzyme activation system known in the art with respect to its potential applications in cancer gene therapy. HSV-TK phosphorylates the prodrug ganciclovir and generates nucleoside analogs that induce DNA chain termination and cell death in actively dividing cells. Tumor cells transduced with HSV-TK acquire sensitivity to ganciclovir, a clinically proven agent originally designed for treatment of viral infections. Moolten, F. L. and Wells, J. M., *J. Natl. Cancer Inst.* 82:297–300 (1990); Ezzeddine, Z. D., et al., *New Biol.* 3:608–614 (1991).

In a second example, the bacterial gene cytosine deaminase (CD) is a prodrug/enzyme activation system that has been shown to sensitize tumor cells to the antifungal agent 5-fluorocytosine as a result of its transformation to 5-flurouracil, a known cancer chemotherapeutic agent (Mullen, C. A., et al., *Proc. Natl. Acad. Sci. USA* 89: 33–37 (1992); Huber, B. E., et al., *Cancer Res.* 53:4619–4626 (1993); Mullen, C. A., et al., *Cancer Res.* 54:1503–1506 (1994)). Recent studies using these drug susceptibility genes have yielded promising results. See, e.g., Caruso, M., et al., *Proc. Natl. Acad. Sci. USA* 90:7024–7028 (1993); Oldfield, E., et al., *Hum. Gene Ther.* 4: 39 (1993); Culver, K., *Clin. Chem* 40: 510 (1994); O'Malley, Jr., B. W., et al., *Cancer Res.* 56:1737–1741 (1996); Rainov, N. G., et al., *Cancer Gene Therapy* 3:99–106 (1996).

Several other prodrug-activating enzyme systems have also been investigated (T. A. Connors, *Gene Ther.* 2:702–709 (1995)). These include the bacterial enzyme carboxypeptidase G2, which does not have a mammalian homolog, and can be used to activate certain synthetic mustard prodrugs by cleavage of a glutamic acid moiety to release an active, cytotoxic mustard metabolite (Marais, R., et al., *Cancer Res.* 56: 4735–4742 (1996)), and *E. coli* nitro reductase, which activates the prodrug CB1954 and related mustard prodrug analogs (Drabek, D., et al., *Gene Ther.* 4:93–100 (1997); Green, N. K., et al., *Cancer Gene Ther.* 4:229–238 (1997)), some of which may be superior to CB1954 (Friedlos, F. et al., *J Med Chem* 40:1270–1275 (1997)). The principle underlying these approaches to prodrug activation gene therapy is that transduction of a tumor cell population with the foreign gene confers upon it a unique prodrug activation capacity, and hence a chemosensitivity which is absent from host cells that do not express the gene.

Current gene therapy technologies are limited by their inability to deliver prodrug activation or other therapeutic genes to a population of tumor cells with 100% efficiency. The effectiveness of this cancer gene therapy strategy can be greatly enhanced, however, by using drugs that exhibit a strong "bystander effect" (Pope, I. M., et al., *Eur J Cancer* 33:1005–1016 (1997)). Bystander cytotoxicity results when active drug metabolites diffuse or are otherwise transferred from their site of generation within a transduced tumor cell to a neighboring, naive tumor cell. Ideally, the bystander effect leads to significant tumor regression even when a minority of tumor cells is transduced with the prodrug activation gene (e.g., Chen, L., et al., *Hum Gene Ther.* 6:1467–1476 (1995); Freeman, S., et al., *Cancer Res.* 53:5274–5283 (1993)). Bystander cytotoxic responses may also be mediated through the immune system, following its stimulation by interleukins and other cytokines secreted by tumor cells undergoing apoptosis (Gagandeep, S., et al., *Cancer Gene Ther.* 3:83–88 (1996)).

Although the ganciclovir/HSV-TK and 5-fluorocytosine/ CD systems have shown promise in preclinical studies, and clinical trials are underway (Eck, S. L., et al., *Hum Gene Ther.* 7:1465–1482 (1996); Link, C. J. et al., *Hum Gene Ther.* 7:1161–1179 (1996); Roth, J. A., and Cristiano, R. J., *J Natl Cancer Inst.* 89:21–39 (1997)), several limitations restrict their efficacy and limit their application to cancer chemotherapeutics. These include: (a) the non-mammalian nature of the HSV/TK and CD genes, whose gene products may elicit immune responses that interfere with prodrug activation; (b) their reliance on drugs which were initially developed as antiviral drugs (ganciclovir) or antifungal drugs (5-fluorocytosine) and whose cancer chemotherapeutic activity is uncertain; (c) the dependence of these gene therapy strategies on ongoing tumor cell DNA replication; and (d) the requirement, in the case of HSV-TK, for direct cell-cell contact to elicit an effective bystander cytotoxic response (Mesnil, M., et al., *Proc. Natl. Acad. Sci. USA.* 93: 1831–1835 (1996)). These considerations, together with the general requirement of combination chemotherapies to achieve effective, durable clinical responses, necessitates the development of alterative strategies to treat cancers using suicide gene-based (prodrug activation) gene therapy.

More recently, a drug activation/gene therapy strategy has been developed based on a cytochrome P450 gene ("CYP" or "P450") in combination with a cancer chemotherapeutic agent that is activated through a P450-catalyzed monoxygenase reaction (Chen, L. and Waxman, D. J., *Cancer Research* 55:581–589 (1995); Wei, M. X., et al., *Hum. Gene Ther.* 5:969–978 (1994); U.S. Pat. No. 5,688,773, issued Nov. 18, 1997). Unlike the prodrug activation strategies mentioned above, the P450-based drug activation strategy utilizes a mammalian drug activation gene (rather than a bacterially or virally derived gene), and also utilizes established chemotherapeutic drugs widely used in cancer therapy.

Many anti-cancer drugs are known to be oxygenated by cytochrome P450 enzymes to yield metabolites that are cytotoxic or cytostatic toward tumor cells. These include several commonly used cancer chemotherapeutic drugs, such as cyclophosphamide (CPA), its isomer ifosfamide (IFA), dacarbazine, procarbazine, thio-TEPA, etoposide, 2-aminoanthracene, 4-ipomeanol, and tamoxifen (LeBlanc, G. A. and Waxman, D. J., *Drug Metab. Rev.* 20:395–439 (1989); Ng, S. F. and Waxman D. J., *Intl. J. Oncology* 2:731–738 (1993); Goeptar, A. R., et al., *Cancer Res.* 54:2411–2418 (1994); van Maanen, J. M., et al., *Cancer Res.* 47:4658–4662 (1987); Dehal, S. S., et al., *Cancer Res.* 57:3402–3406 (1997); Rainov, N. G., et al., *Human Gene Therapy* 9:1261–1273 (1998)). Bioreductive metabolism that results in drug activation is also catalyzed by cytochrome P450 enzymes for a variety of anti-cancer drugs. Examples of such drugs include Adriamycin, mitomycin C, and tetramethylbenzoquinone (Goeptar, A. R., et al., *Crit. Rev. Toxicol.* 25:25–65 (1995); Goeptar, A. R., et al., *Mol. Pharmacol.* 44:1267–1277 (1993)).

CPA and IFA undergo bioactivation catalyzed by liver cytochrome P450 enzymes (Sladek, N. E., *Pharmacol. Ther.* 37:301–355 (1988)). Although IFA is an isomer of CPA, it is activated by a distinct subset of P450 enzymes, both in rodent models and in humans (Chang, T. K. H., et al., *Cancer Res.* 53:5629–5637 (1993); Weber, G. F. and Waxman, D. J., *Biochem Pharmacol.* 45:1685–1694 (1993)). The primary 4-hydroxy metabolite is formed at high levels in the liver and spontaneously decomposes, both in the circulation and within the target tumor cells, to yield acrolein and an electrophilic mustard, which exhibits the DNA crosslinking and cytotoxic effects associated with the parent drug. However, the systemic distribution of CPA and IFA and their alkylating metabolites inevitably results in several significant side effects, including cardiotoxicity, renal toxicity, marrow suppression, and neurotoxoxicity (Peters, W. P., et al., *J. Clin. Oncol.* 11:1132–1143 (1993); Ayash, L. J., et al., *J. Clin. Oncol.* 10:995–1000 (1992); Goren, M. P., et al., *Lancet* 2:1219–1220 (1986); Thigpen, T., *Gynecol Oncol.* 42:191–192 (1991)).

Some of these limitations can be overcome using a P450-based drug/enzyme activation system. In one example of this approach, tumor cells were rendered highly sensitive to CPA or IFA by transduction of CYP2B1, which encodes a liver P450 enzyme that exhibits a high rate of CPA and IFA activation (Clarke, L. and Waxman, D. J., *Cancer Res.* 49:2344–2350 (1989); Weber, G. F. and Waxman, D. J., *Biochem. Pharmacol.* 45:1685–1694 (1993)). This enhanced chemosensitivity has been demonstrated both in vitro and in studies using a subcutaneous rodent solid tumor model and human breast tumor grown in nude mice in vivo, and is strikingly effective in spite of the presence of a substantial liver-associated capacity for drug activation in these animals (Chen, L., et al., *Cancer Res.* 55:581–589 (1995); Chen, L., et al., *Cancer Res.* 56:1331–1340 (1996)). This P450-based approach also shows significant utility for gene therapy applications in the treatment of brain tumors (Wei, M. X., et al., *Human Gene Ther.* 5:969–978 (1994); Manome, Y., et al., *Gene Therapy* 3:513–520 (1996); Chase, M., et al., *Nature Biotechnol.* 16:444–448 (1998)).

Although the P450/drug activation system has shown great promise against several tumor types, further enhancement of the activity of this system is needed to achieve clinically effective, durable responses in cancer patients. This requirement is necessitated by two characteristics that are inherent to the P450 enzyme system: (1) P450 enzymes metabolize drugs and other foreign chemicals, including cancer chemotherapeutic drugs, at low rates, with a typical P450 turnover number (moles of metabolite formed/mole P450 enzyme) of only 10–30 per minute; and (2) P450 enzymes metabolize many chemotherapeutic drugs with high Km values, typically in the millimolar range. This compares to plasma drug concentrations that are only in the micromolar range for many chemotherapeutic drugs, including drugs such as CPA and IFA. Thus, current approaches to P450 gene therapy may result in intratumoral drug activation at a low absolute rate and under conditions that are not saturating with respect to drug substrate. Furthermore, since P450 is expressed at a very high level in liver tissue, only a very small fraction of the administered chemotherapeutic drug is metabolized via the tumor cell P450 gene product using the currently available methods for P450 gene therapy (Chen, L. and Waxman, D. J., *Cancer Res.* 55:581–589 (1995)).

Thus, in light of the foregoing, there is a need in the art for a method that will enhance the activity of a P450 gene product delivered to a tumor cell, in a manner that enhances the intratumoral drug activation reaction, in order to increase both the extent and selectivity of tumor cell destruction that occurs following treatment with a P450-activated chemotherapeutic agent. Moreover, in view of the radiation resistance and chemotherapeutic drug insensitivity that characterizes hypoxic tumor cells found in many human tumors (Brown, J. M. and Giaccia, A. J., *Cancer Res.* 58:1408–1416 (1998)), there is a need in the art for a method whereby a P450 gene product delivered to a tumor cell will kill hypoxic tumor cells, which may otherwise escape killing by classical treatment regimens.

SUMMARY OF THE INVENTION

The inventors have discovered that by introducing a cytochrome P450 reductase (RED) gene (and thus a RED gene product) in combination with a cytochrome P450 gene (and thus a P450 gene product) into neoplastic cells, the enzymatic conversion of a P450-activated chemotherapeutic drug to its therapeutically active metabolites is greatly enhanced within the cellular and anatomic locale of the tumor, thereby increasing both the selectivity and efficiency with which neoplastic cells are killed. At the same time, undesirable side-effects to normal host cells are minimized.

Accordingly, the present invention overcomes the disadvantages of the prior art by providing a method for killing neoplastic cells, the method comprising: (a) infecting the neoplastic cells with a vector for gene delivery, the vector comprising a cytochrome P450 gene and a gene encoding RED; (b) treating the neoplastic cells with a chemotherapeutic agent that is activated by the product of the cytochrome P450 gene; and (c) killing the neoplastic cells.

In addition, the present invention provides a method for killing neoplastic cells, the method comprising: (a) infecting the neoplastic cells with two vectors; one vector comprising a cytochrome P450 gene, the other vector comprising a gene encoding RED; (b) treating the neoplastic cells with a chemotherapeutic agent that is activated by the product of the cytochrome P450 gene; and (c) killing the neoplastic cells.

The invention also provides a preferred embodiment of the foregoing methods wherein the cytochrome P450 gene is a mammalian gene, such as P450 1A1, 1A2, 1B1, 2B1, 2B2, 2B4, 2B5, 2B6, 2B11, 2A6, 2C6, 2C8, 2C9, 2C11, 2C18, 2C19, 2D6, 2E1, 3A4, 3A5, 3A7, or 4B1 whose cDNA sequences are known (Nelson, D. R., et al., *Pharmacogenetics* 6:1–42 (1996)). Other cytochrome P450 genes, including members of corresponding P450 gene families and subfamilies in other species, and their allelic variants, site-specific mutants, and chimeric constructs (e.g., Chang, T. K. H., et al., *Pharmacogenetics* 7:211–221 (1997); Szldarz, G. D., et al., *Biochemistry* 34:14312–14322 (1995); He, Y. A., et al., *Biochemistry* 36:8831–8839 (1997)) are also provided as embodiments of the invention, so long as they activate chemotherapeutic agents useful in cancer therapy. Rat cytochrome gene P450 2B1, and human cytochrome genes P450 2B6, P450 2C18, and P450 3A4 are particularly preferred.

In another preferred embodiment of the foregoing methods, the P450-activated chemotherapeutic agent is cyclophosphamide (CPA), ifosfamide (IFA), dacarbazine, procarbazine, thio-TEPA, etoposide (VP-16), tamoxifen, 4-ipomeanol, 2-aminoanthracene, or any other P450-metabolized chemotherapeutic drug. CPA and IFA are particularly preferred.

The invention also provides a very particularly preferred embodiment of the foregoing methods, wherein the cytochrome P450 gene is P450 2B1, P450 2B6, or P450 2C18, and the chemotherapeutic agent is cyclophosphamide. In another very particularly preferred embodiment, the cytochrome P450 gene is P450 2B1 or P450 3A4 and the chemotherapeutic agent is ifosfamide.

The invention also provides a preferred embodiment of the foregoing methods, wherein the P450 gene and the RED gene are delivered using one or more viral vectors, preferably viral vectors whose use for gene therapy is well-established for those skilled in the art. Examples of such viral vectors include retrovirus (including lentivirus), adenovirus, adeno-associated virus, herpes virus (including herpes simplex virus I and II and Epstein Barr virus), poliovirus, papillomavirus, or hybrid vectors having attributes of two or more viruses. Retroviruses and adenoviruses are particularly preferred viral vectors.

In one embodiment, a single viral vector is used to carry both the P450 and the RED genes. If a single vector is used, the P450 gene and the RED gene can be delivered as a fusion gene which encodes a P450-RED fusion protein. Alternatively, the vector for gene delivery can include an internal ribosome entry site (IRES) sequence to achieve coordinate expression of the P450 gene and the RED gene on a bicistronic message. Another alternative is for the vector to contain both the P450 gene and the RED gene under the control of distinct promoters. In another embodiment, two viral vectors are used; one carrying the P450 gene and the other carrying the RED gene.

In another embodiment of the foregoing methods, the P450 gene and the RED gene are delivered using any non-viral vector, preferably one whose use for gene therapy is well-established for those skilled in the art. Examples of such non-viral vectors for gene delivery include prokaryotic vectors (including tumor targeted bacterial vectors), cationic liposomes, DNA-protein complexes, non-viral T7 autogenevectors, fusogenic liposomes, direct injection of nucleic acid ("naked DNA"), particle or receptor-mediated gene transfer, hybrid vectors such as DNA-adenovirus conjugates or other molecular conjugates involving a non-viral and viral component, starburst polyamidoamine dendrimers, cationic peptides, and mammalian artificial chromosomes.

In addition, the present invention provides an embodiment of the foregoing methods wherein the P450 gene and the RED gene are delivered using any cellular vector, preferably one whose use for gene therapy is well-established for those skilled in the art. Examples of such cellular vectors for gene therapy include endothelial cells and macrophages including tumor-infiltrating macrophages, each of which may be modified using viral or non-viral vectors to carry the P450 gene and/or the RED gene, and thus express the P450 and RED gene products.

Further, the present invention provides an embodiment of the foregoing methods, wherein the neoplastic cells are also treated with a bioreductive drug (i. e., the bioreductive drug is administered in addition to treatment with the P450-activated chemotherapeutic agent described above). Alternatively, the bioreductive drug may be used on its own (i.e., in place of the P450-activated chemotherapeutic agent). In a preferred embodiment, the bioreductive drug is a nitroimidazole, a nitroaromatic, a quinone, an aliphatic, aromatic, or heterocyclic N-oxide, or a bioreducible DNA alkylator, that is capable of undergoing RED-catalyzed and/or P450-catalyzed bioreductive activation. Representative examples of such bioreductive drugs include Adriamycin, porfiromycin, mitomycin C, tirapazamine (also known as SR 4233 or TPZ), indoloquinone E09, aziridinylnitroimidazoles RSU 1069 or RB6145, dinitrophenylaziridine (CB1954), 2,3,5,6-tetramethylbenzoquinone (TMQ), diaziquone (AZQ), the intercalator amine N-oxide AQ4N, and the bioreducible DNA alkylators NSC646394 and NSC658926.

In addition, the present invention provides methods for killing neoplastic cells wherein endogenous levels of either cytochrome P450 or RED are increased in the neoplastic cells, and gene transfer is carried out with the gene whose product is not endogenously increased.

Thus, in accordance with this aspect of the invention, a method for killing neoplastic cells is provided, the method comprising: (a) administering an agent that will increase the activity or expression level of endogenous RED in the neoplastic cells; (b) infecting the neoplastic cells with a vector, the vector comprising a cytochrome P450 gene; (c) treating the neoplastic cells with a chemotherapeutic agent that is activated by the gene product of the cytochrome P450 gene; and (d) killing the neoplastic cells. In a preferred embodiment of this method, the cytochrome P450 gene is a mammalian gene, such as P450 1A1, 1 A2, 1B1, 2B1, 2B2, 2B4, 2B5, 2B6, 2B1 1, 2A6, 2C6, 2C8, 2C9, 2C11, 2C18, 2C19, 2D6, 2E1, 3A4, 3A5, 3A7, or 4B1 and members of corresponding P450 gene subfamilies in other species. Rat cytochrome gene P450 2B1, and human cytochrome genes P450 2B6, P450 2C18, and P450 3A4 are particularly preferred.

Also in accordance with this aspect of the invention, a method for killing neoplastic cells is provided, the method comprising: (a) administering an agent that will increase the activity or expression level of endogenous cytochrome P450 in the neoplastic cells; (b) infecting the neoplastic cells with a vector, the vector comprising a RED gene; (c) treating the neoplastic cells with a chemotherapeutic agent that is activated by the product of the cytochrome P450 gene; and (d) killing the neoplastic cells.

The invention also provides preferred embodiments of the foregoing methods, wherein the agent that will increase the activity or expression level of endogenous RED in the neoplastic cells is thyroid hormone or phenobarbital, and the agent that will increase the activity or expression level of endogenous P450 in the neoplastic cells is dexamethasone, rifampin, 1,4-bis-2-(3,5-dichloropyridyloxybenzene) (TCPOBOP), or phenobarbital.

In addition, the invention also provides a preferred embodiment of the foregoing methods, wherein the chemotherapeutic agent is cyclophosphamide, ifosfamide, dacarbazine, procarbazine, thio-TEPA, etoposide (VP-16), tamoxifen, 4-ipomeanol, or 2-aminoanthracene.

The present invention also provides an embodiment of the foregoing methods, wherein the neoplastic cells are also treated with a bioreductive drug (i.e., the bioreductive drug is administered in addition to treatment with the P450-activated chemotherapeutic agent described above). Alternatively, the bioreductive drug may be used on its own (i.e., in place of the P450-activated chemotherapeutic agent). In a preferred embodiment, the bioreductive drug is a nitroimidazole, a nitroaromatic, a quinone, an aliphatic, aromatic or heterocyclic N-oxide, or a bioreducible DNA alkylator, that is capable of undergoing RED-catalyzed and/or P450-catalyzed bioreductive activation. Representative examples of such bioreductive drugs include Adriamycin, porfiromycin, mitomycin C, tirapazamine (TPZ or SR 4233), indoloquinone E09, aziridinylnitroimidazoles RSU 1069 or RB6145, dinitrophenylaziridine (CB1954), 2,3,5,6-tetramethylbenzoquinone (TMQ), diaziquone (AZQ), the intercalator amine N-oxide AQ4N, and the bioreducible DNA alkylators NSC646394 and NSC 658926.

The present invention also provides an embodiment, whereby the cytochrome P450 and RED based drug activation system is combined with established gene/prodrug activation systems, such as ganciclovir/HSV-TK and 5-fluorocytosine/CD. P450/RED gene therapy may also be combined with other established cancer therapeutic genes, including tumor suppressor genes, such as p53; apoptotic factors, such as bax, tumor necrosis factor alpha, and caspases; and cytokines, such as interleukin 2, interleukin 4, and interleukin 12.

In another embodiment of the present invention, the targetting specificity for P450 and RED gene delivery is facilitated by "transcriptional targeting," including the use of tumor-specific or tumor-selective DNA enhancer sequences. Examples of such sequences include those described for genes that encode tyrosinase (melanoma), ERBB2 (pancreatic cancer), carcinoembryonic antigen (lung and gastrointestinal cancer), DF3/MUC1 (breast cancer), alpha-fetoprotein (hepatoma), as well as synthetic gene regulation systems which allow for transcriptional control and other forms of regulated expression of the P450 and/or RED genes. Targeting also includes sequences that control expression of genes induced by hypoxia (hypoxia response elements), or other tumor-specific conditions and factors.

In yet another embodiment of the present invention, the cytochrome P450 and RED-based drug activation system is combined with selective inhibitors of hepatic P450-catalyzed prodrug activation to increase the specificity of intratumoral drug activation.

In another specific embodiment of the present invention, the cytochrome P450 gene product and/or the RED gene product are delivered to the neoplastic cells, rather than delivery of the corresponding gene(s). In this embodiment, streptavidin-biotin-based and other protein delivery methods are employed, which are well known to those skilled in the art.

The invention also provides another embodiment of the invention, whereby the levels of endogenous RED and/or cytochrome P450 are assayed in biopsies prepared from a given human tumor, in order to predict responsiveness to P450-activated chemotherapeutic drugs, like CPA and IFA, or RED-activated bioreductive drugs, like tirapazamine (TPZ).

In another embodiment, levels of endogenous RED are assayed in a given human tumor as a prognostic indicator of the effectiveness of P450-based gene therapy (in the absence of cotransfected RED) and to help determine if RED would be particularly useful to incorporate into a P450-based gene therapy strategy. That is, tumor cells with moderate or low levels of RED activity would be prime candidates for incorporating the RED gene into any P450 based gene therapy paradigm.

Previous studies using the P450/anti-cancer drug activation system have been based on the premise that RED gene transfer is unnecessary because RED is widely expressed in the target tumor cells. Indeed, P450-based cancer gene therapy in combination with CPA treatment is strikingly effective without concomitant transfer of RED (Chen, L. and Waxman, D. J., *Cancer Research* 55:581–589 (1995); Wei, M. X., et al., *Hum. Gene Ther.* 5:969–978 (1994); Chen, L., et al., *Cancer Res.* 56:1331–1340 (1996); Manome, Y., et al., *Gene Therapy* 3:513–520 (1996); Chase, M., et al., *Nature Biotechnol.* 16:444–448 (1998)). In liver cells, which express levels of P450 that are approximately 50–100-fold higher than achieved in the inventors' intratumoral P450 gene expression studies (Chen, L. and Waxman, D. J., *Cancer Research* 55:581–589 (1995)), the RED component can, under certain conditions, be rate-limiting with respect to P450-catalyzed enzymatic reactions (Waxman, D. J., et al., *Mol. Pharmacol.* 35:519–525 (1989)). Titration and reconstitution studies indicate, however, that an equal mole level of RED and P450 is required to achieve maximal P450 monooxygenase activity (Yamano, S., et al., *Mol. Pharmacol.* 36:83–88 (1989)), and that the rate-limiting nature of RED should only be manifest at higher levels of P450 (Miwa, G. T., et al., *J. Biol. Chem.* 253:1921–1929 (1978); Cawley, G. F., et al., *Biochemistry* 34:1244–1247 (1995)).

In the present invention, the inventors have discovered and demonstrated, in vitro and in vivo, that the therapeutic activity of anticancer drug P450-based tumor gene therapy can be enhanced by cotransfer of the RED gene. Despite the expectation that endogenous RED would not be limiting in tumor cells when they are engineered to express low P450 levels (Yamano, S., et al., *Mol. Pharmacol.* 36:83–88 (1989); Waxman, D. J., et al., *Mol. Pharmacol.*, 35:519–525 (1989); Miwa, G. T., et al., *J. Biol. Chem.* 253:1921–1929 (1978)), RED overexpression leads to a substantial augmentation of P450-mediated anti-cancer drug chemosensitivity, both in cells transduced with a P450 gene that is expressed at a high level, and in cells transduced to give a low level of P450 expression. These findings enhance the efficacy of P450-based suicide gene therapy strategies, and facilitate the application of P450 gene therapy to cancer therapeutics.

It is to be understood that both the foregoing general description and the following detailed description are exemplary and explanatory and are intended to provide further explanation of the invention as claimed.

Survival of the parental 9L, 9L-R (cells which overexpress P450 reductase or RED$^{+++}$), P3, P17 (CYP2B1$^+$ cells), PR11, and PR7 (CYP2B1$^+$RED$^{+++}$) cells exposed to CPA (FIGS. 2A and 2B) or IFA (FIG. 2C) are shown.

Figure 2A:
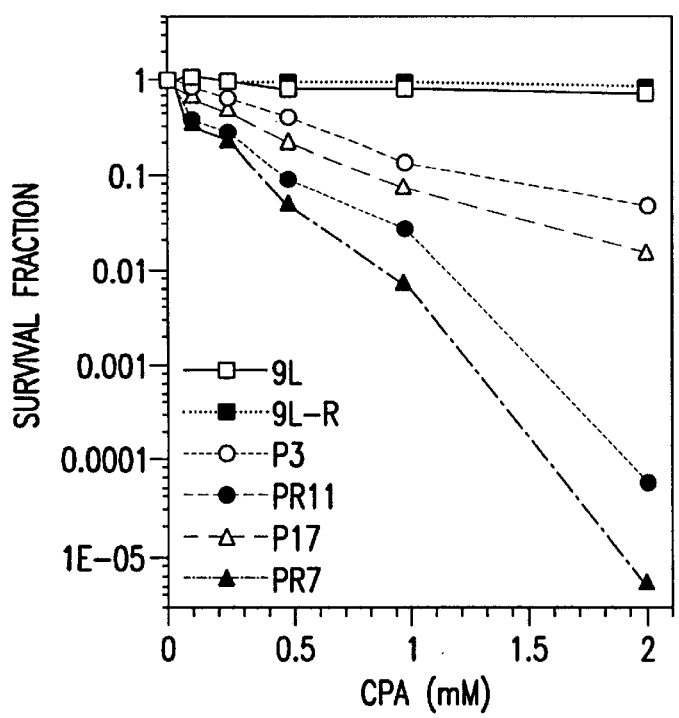
FIGS. 2A, 2B, and 2C are graphs depicting the enhanced cytotoxic effects of the chemotherapeutic drugs CPA and ifosfamide (IFA) on the survival of P450-expressing 9L tumor cells, following co-transfer of the RED gene.
Figure 2B:
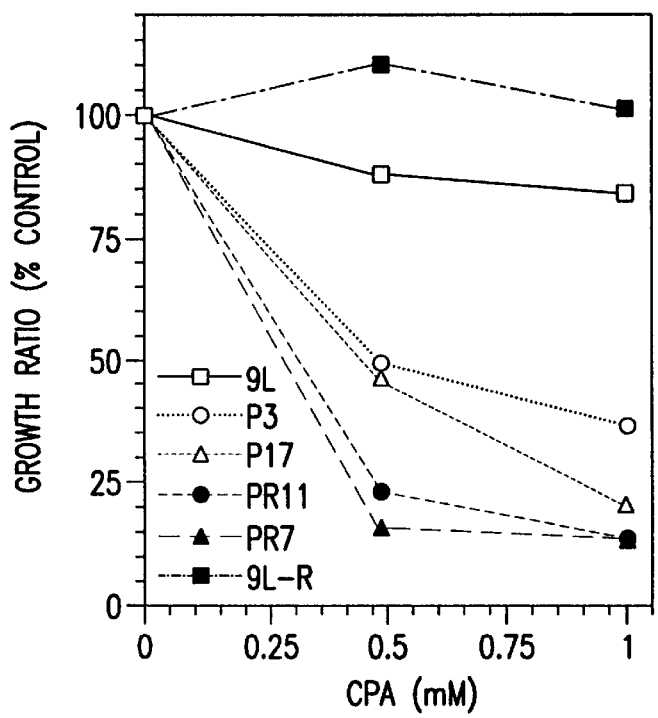
Figure 2C:
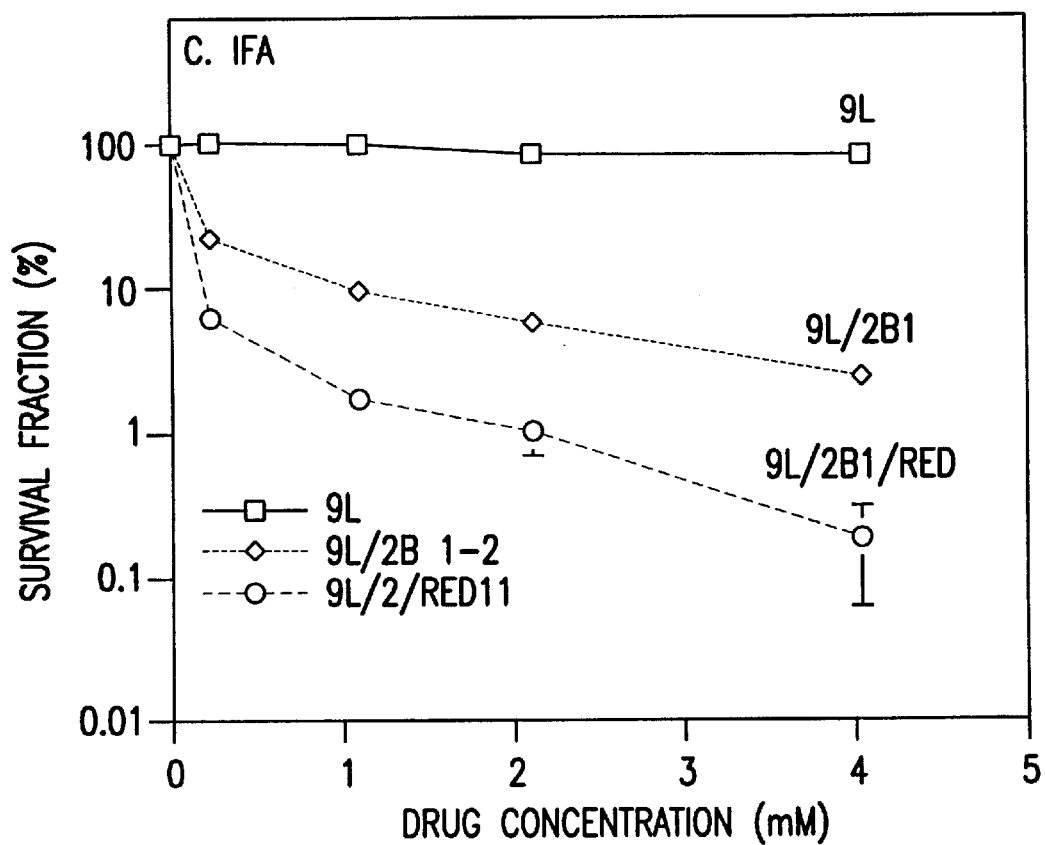

FIGS. 2A and 2C depict the results of a colony formation cytotoxicity assay. Cells were plated in duplicate in 30 mm tissue culture plates at 200, 2,000, and 20,000 cells per well and treated with CPA (FIG. 2A) or IFA (FIG. 2C) at the indicated drug concentrations. Seven days later, plates were stained with crystal violet, and the number of colonies was counted. The survival fraction was expressed as the number of colonies in treated group compared to the untreated control.

FIG. 2B depicts the results from a growth inhibition assay. Cells (1000/well) seeded in 96-well plates were treated with the indicated concentrations of CPA for 4 days. Corresponding controls received no drug treatment. Cell survival was determined by an XTT calorimetric assay. Data (mean for triplicate samples) were expressed as growth ratio (%), i. e., cell number (XTT activity) in drug treated plates as a percentage of the corresponding drug-free controls.

Figure 3A:
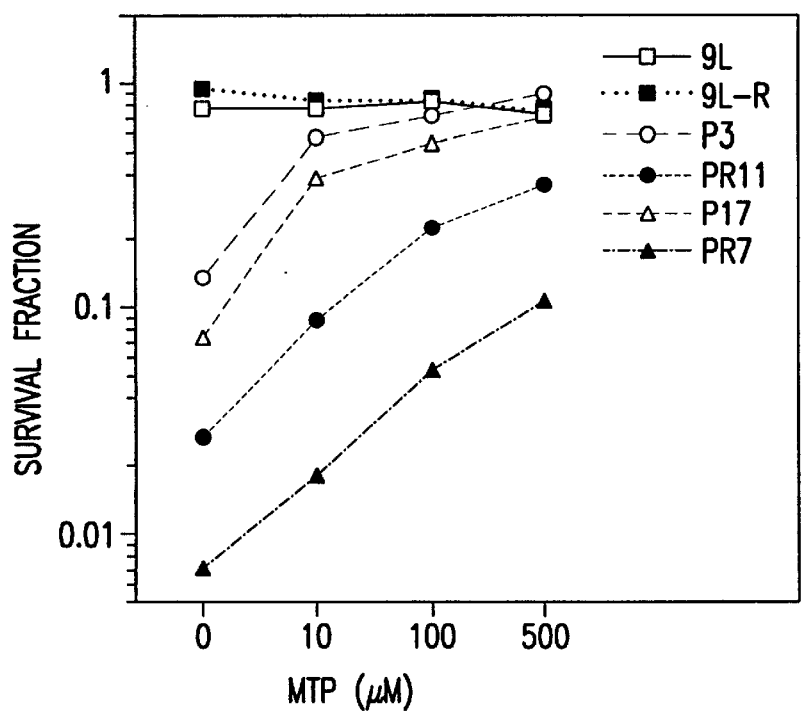
Figure 3B:
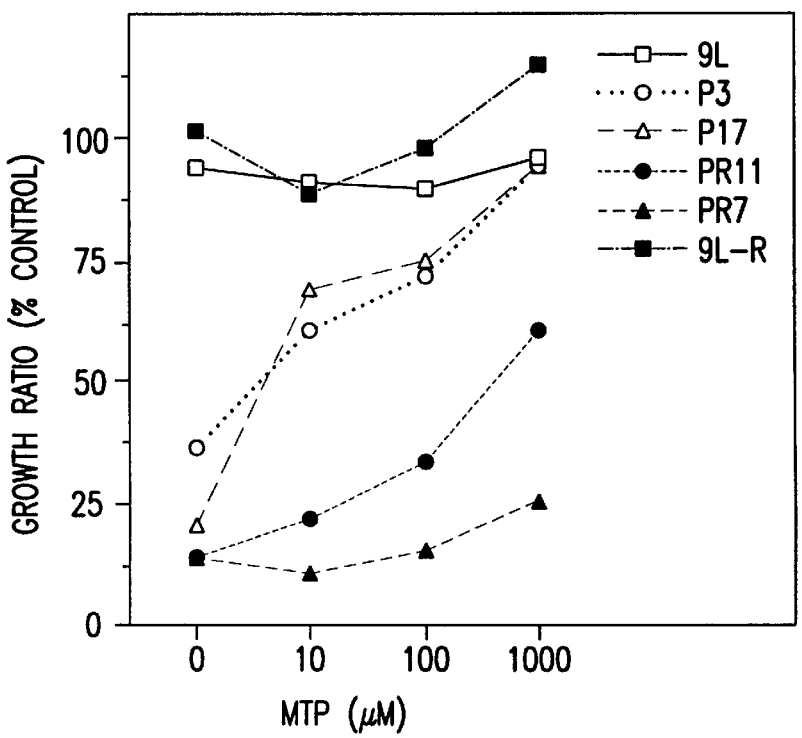

FIGS. 3A and 3B are graphs depicting the protection from CPA cytotoxicity by the P450 enzyme inhibitor metyrapone (MTP) in P450-transduced tumor cells (CYP2B1$^+$), and the less effective protection by MTP in tumor cells transduced with P450 and RED in combination (CYP2B1$^+$RED$^{+++}$).

FIG. 3A depicts results from a colony formation cytotoxicity assay. Cells (200 and 2000 cells/well) were plated in duplicate in 30 mm tissue culture plates and treated with 1 mM cyclophosphamide in the absence or presence of the indicated concentrations of MTP. Seven days after treatment, plates were stained with crystal violet and the number of colonies was counted. The survival fraction is expressed as the number of colonies in each treatment group compared to the untreated control.

FIG. 3B depicts results from a growth inhibition assay. Cells (1000/well) seeded in 96-well plates were treated with 1 mM cyclophosphamide in the absence or presence of MTP, as indicated. Corresponding controls received no drug treatment. Cell survival was determined by an XTT colorimetric assay. Data (mean for triplicate samples) are expressed as growth ratio (%), i.e., cell number (XTT activity) in drug treated plates as a percentage of the corresponding drug-free controls.

Figure 4:
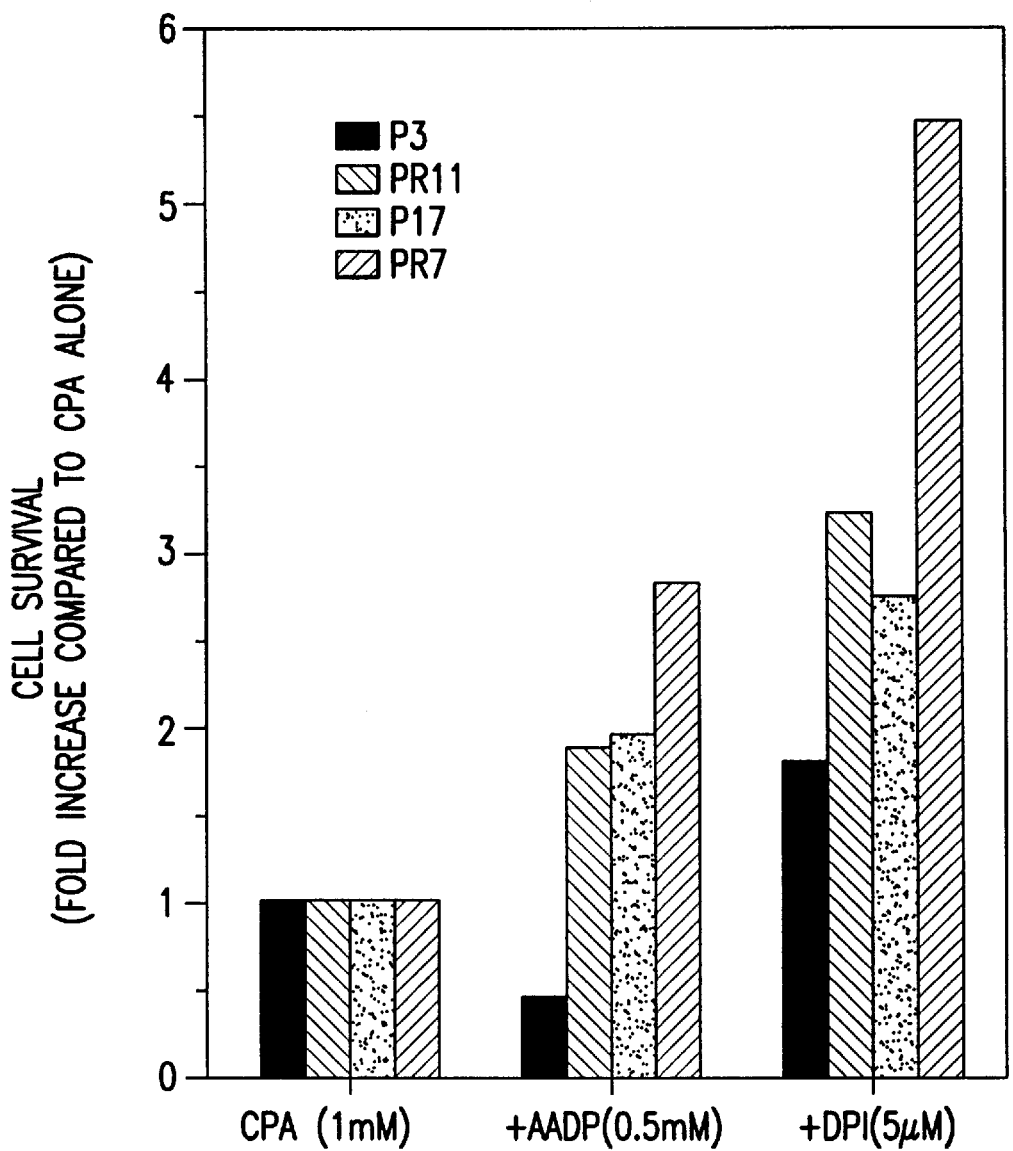

FIG. 4 is a bar graph depicting the protection from CPA cytotoxicity afforded by the RED inhibitors 3-aminopyridine adenine dinucleotide (AADP) and diphenyleneiodonium (DPI) in P450 and RED-transduced tumor cells. Cells (500/well) seeded in 96-well plates were treated with 1 mM cyclophosphamide in the absence or presence of the RED inhibitors AADP (0.5 mM) or DPI (5 μM). Corresponding controls received no drug treatment. Cell survival was determined by an XTT colorimetric assay. Data (mean for triplicate samples) are expressed as growth ratio (%), i.e., cell number (XTT activity) in drug treated plates as a percentage of the corresponding drug-free controls and are representative of 2–3 independent experiments. AADP and DPI were added to the cells 30 minutes prior to CPA treatment.

Figure 5:
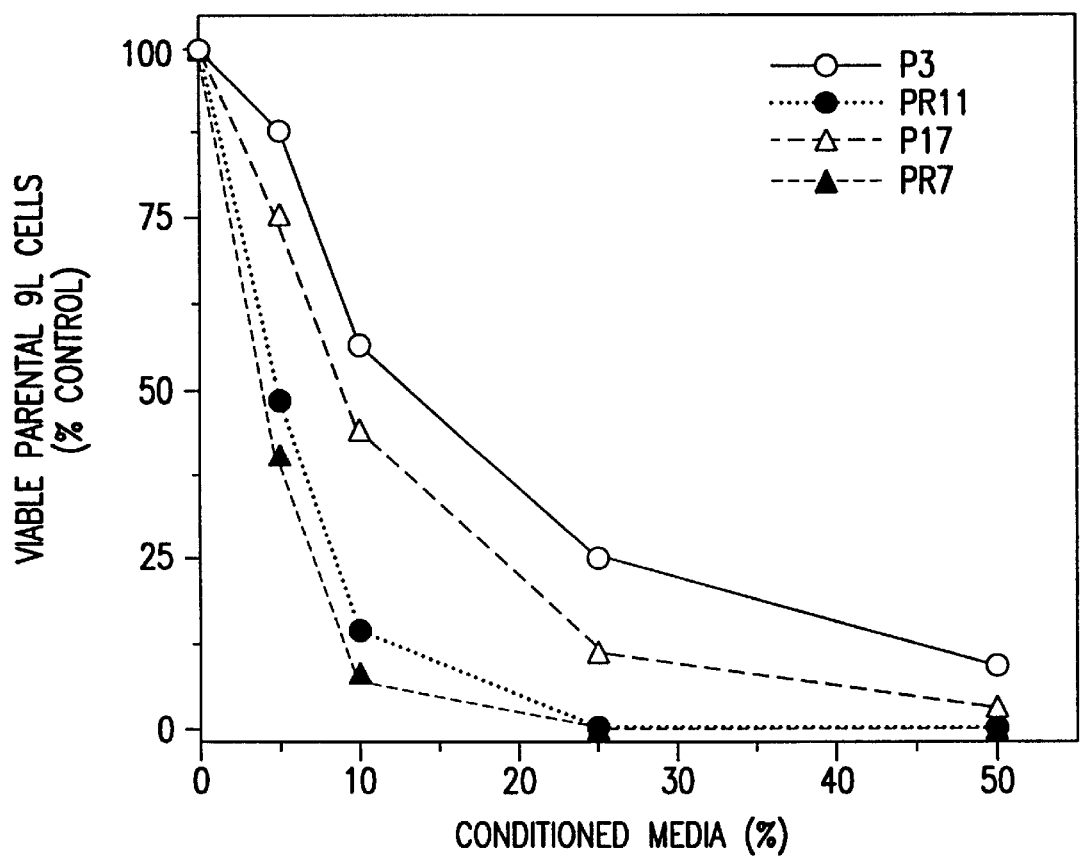

FIG. 5 is a graph depicting the effects of culture media from P450 and RED-transduced tumor cells incubated with CPA, on the survival of wild-type tumor cells. The graph shows that CPA-treated CYP2B1$^+$RED$^{+++}$ cells mediate a strong bystander cytotoxic effect toward CYP2B1-negative cells. Parental 9L cells seeded in 30 mm plates (10$^4$ cells/well) in duplicate were cultured with 5–50% of condition media collected from each of the indicated cell lines (1.5× 10$^6$) incubated with 2 mM CPA for 48 hours as described below in the "Materials Methods" section of Example 1. Five days after treatment, the number of viable parental 9L cells was determined using a hemacytometer based on trypan blue exclusion (mean for duplicate values).

FIGS. 6A, 6B, 6C, and 6D are photographs depicting the bystander cytotoxic effects of CPA-treated P450-containing tumor cells (FIGS. 6A and 6B) or P450 and RED-containing tumor cells (FIGS. 6C and 6D) toward nearby wild-type tumor cells marked with the lacZ gene and revealed by dark staining. CYP2B1$^+$ cells (FIG. 6A) and CYP2B1$^+$RED$^{++}$ cells (FIG. 6C) were mixed with equal numbers of lacZ-marked 9L cells and cultured in the absence (FIGS. 6A and 6C) or in the presence (FIGS. 6B and 6D) of 1 mM CPA. Shown are 0.5% glutaraldehyde-fixed cells, 5 days after beginning drug treatment, stained with X-Gal for 4 hours to visualize the 9L-lacZ cells (dark staining).

Figure 7:
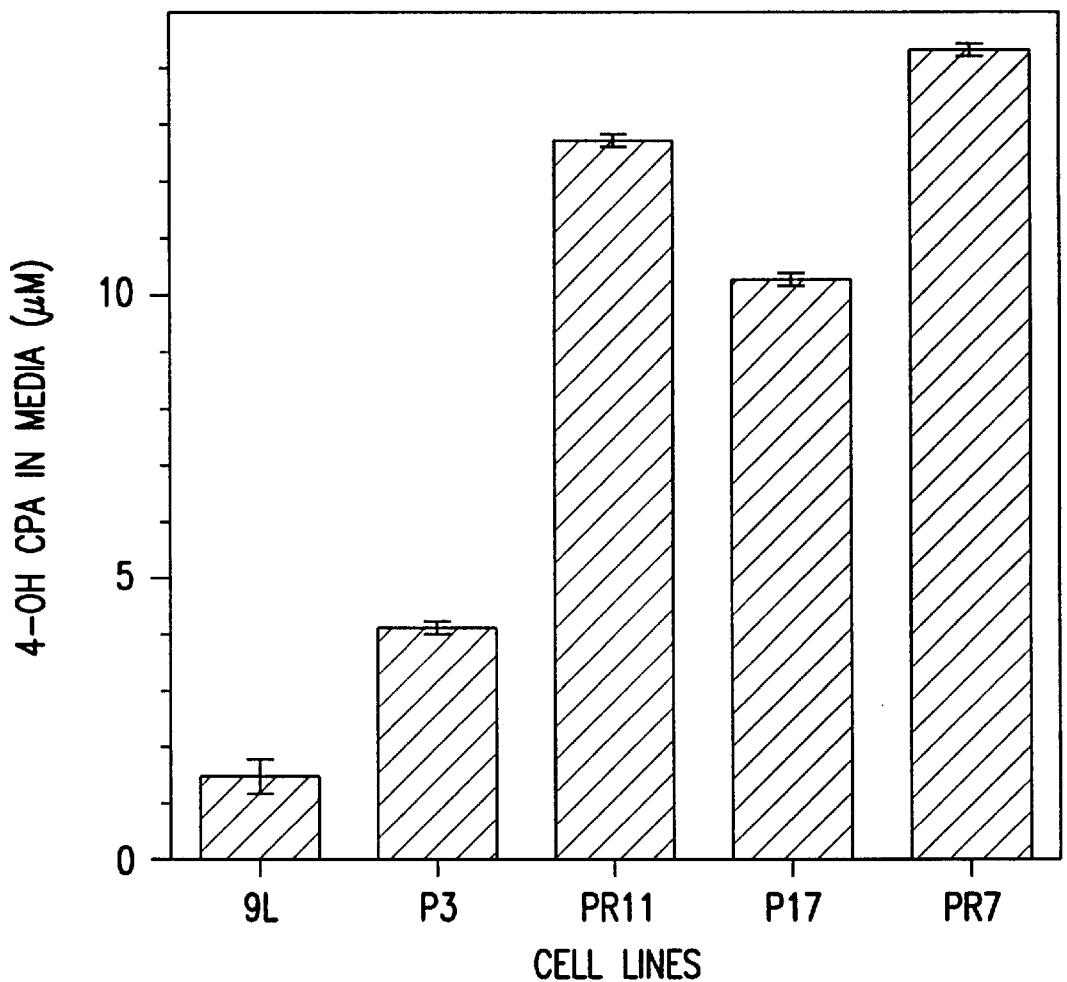

FIG. 7 is a bar graph showing that higher 4-hydroxy-CPA levels are produced by P450 and RED-containing tumor cells compared to tumor cells containing P450 alone. The parental CYP2B1$^+$ cell lines P3 and P17, and their corresponding RED overexpressing derivatives PR11 and PR7 were plated confluent ($1.5 \times 10^6$ cells per 30 mm culture dish) so that the cell number remained relatively constant during the course of the experiment. Cells were incubated for 24 hours with 2 mM CPA in the presence of 5 mM semicarbazide. Medium was collected and then assayed for 4-hydroxy-CPA using a fluorometric assay, as described below in the "Materials and Methods" section of Example 1. Limit of detection in this assay was approximately 1 $\mu$M 4-hydroxy-CPA. The higher CPA 4-hydroxylase activity of line P 17 compared to line P3 is consistent both with the higher cytotoxic potential of CPA-conditioned media from P17 cells (FIG. 5), and with the greater cytotoxicity of CPA toward the P 17 cells in vitro (FIGS. 2, 3) and in vivo (FIG. 9, below).

Figure 8B:
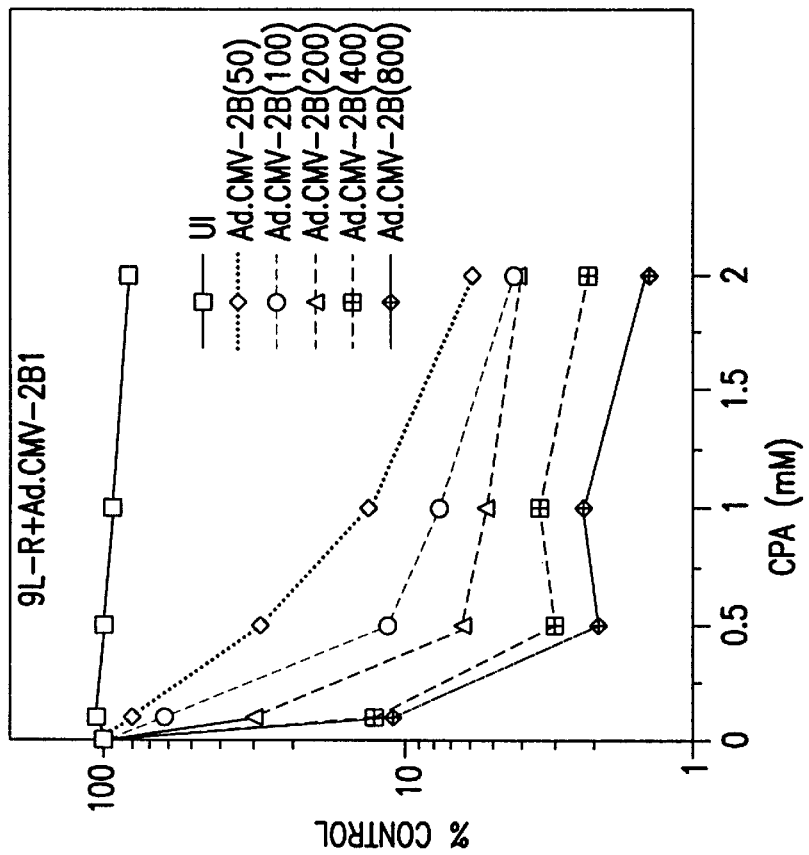
Figure 8A:
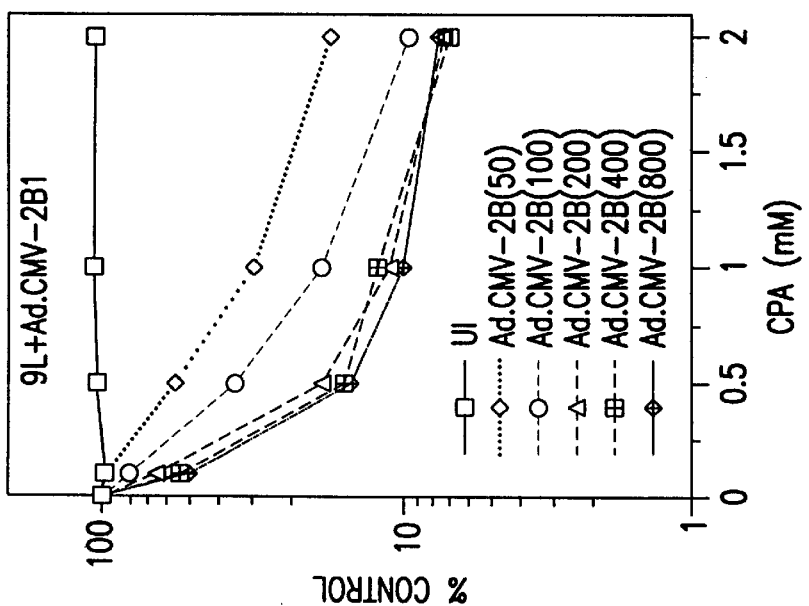

FIGS. 8A and 8B are graphs depicting much greater cytotoxicity of adenovirus-mediated P450 gene transfer combined with CPA treatment in the case of 9L tumor cells engineered to express RED (FIG. 8B), compared to wild-type 9L cells that express basal RED activity (FIG. 8A). Cells were infected with Ad.CMV-2B1 at multiplicities of infection (MOI) ranging from 50–800, as indicated by the values in parenthesis on the right of each panel. Uninfected cells (UI) were used as controls. At 24 hours post infection, cells were replated at 500 cells per well in duplicate on 96-well plates. CPA was then added at concentrations up to 2 mM. After 5 days of incubation, cell survival was determined by an XTT colorimetric assay. Data (mean±range for duplicate samples) are expressed as growth ratio (%), i.e., cell number (XTT activity) in drug treated plates as a percentage of the corresponding drug-free controls.

Figure 9:
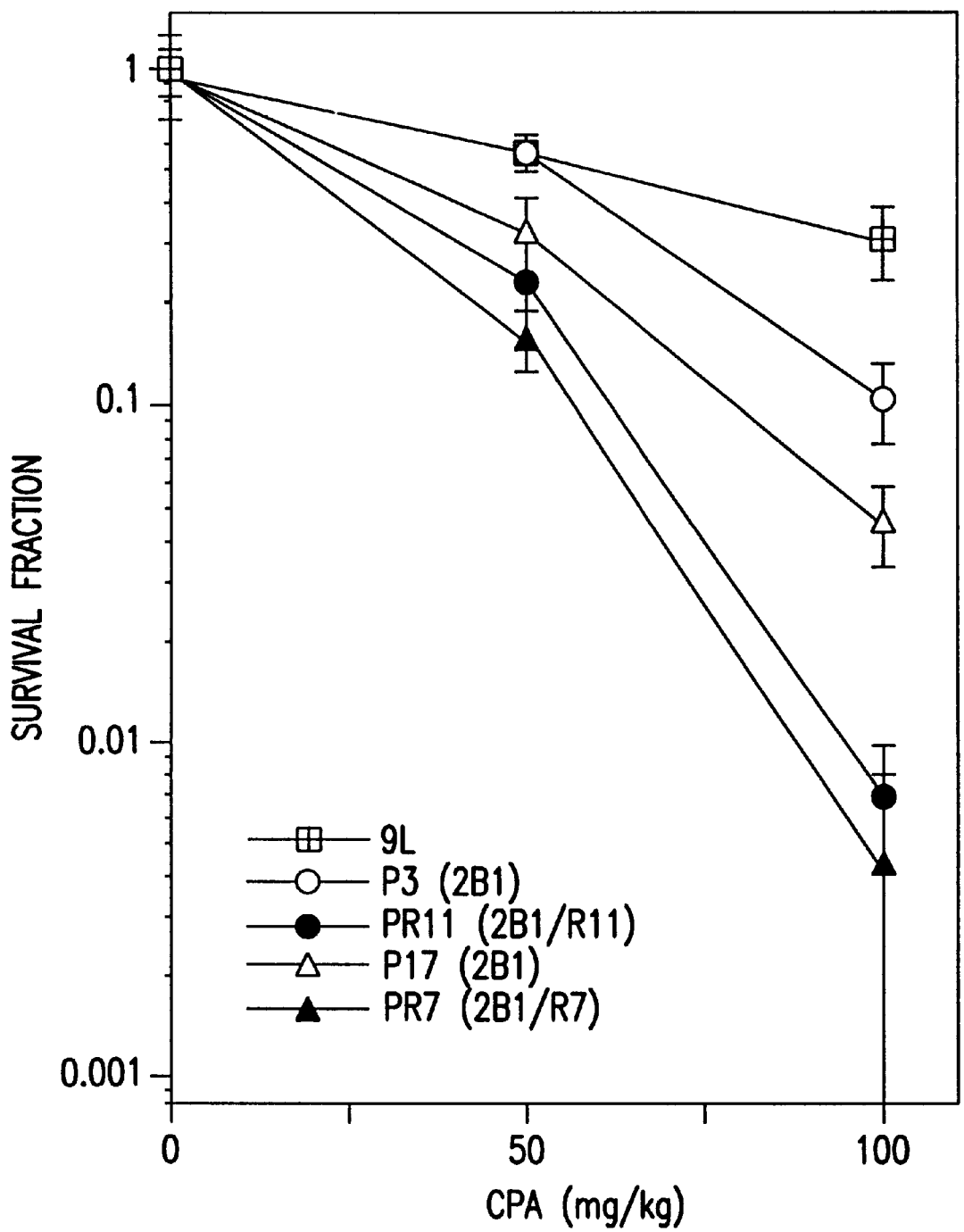

FIG. 9 is a graph depicting the results of an in vivo tumor excision assay, which quantitates the extent of CPA-induced tumor cell kill in rats in vivo for 9L tumors, compared to 9L tumors engineered to express P450 alone (CYP2B1$^+$) or P450 in combination with RED (CYP2B1$^+$RED$^{+++}$). Female Fischer 344 rats were inoculated with parental 9L, CYP2B1$^+$, and CYP2B1$^+$RED$^{+++}$ tumor cells by subcutaneous injection of $2 \times 10^6$ tumor cells/0.2 ml in the hindleg as described below in the "Materials and Methods" section of Example 1. At 2 weeks after tumor implantation, each animal received a single injection of CPA (50 or 100 mg/kg body weight) or saline as control. Twenty four hours later, tumors were excised, and single cell suspensions were prepared for assay of colony formation activity. Results are presented as mean survival fractions as compared to control groups, for 4 or 5 determinations; bars, standard error (SE).

Figure 10:
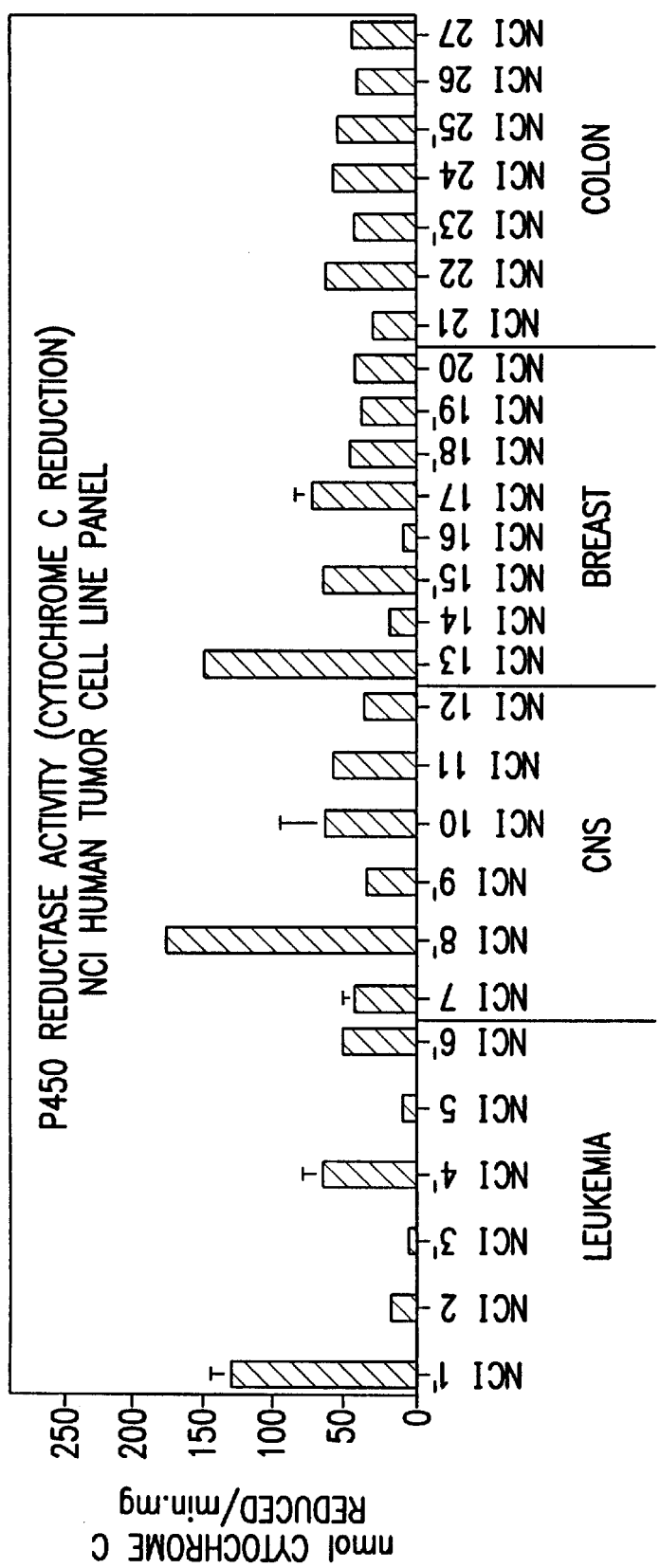
Figure 10:
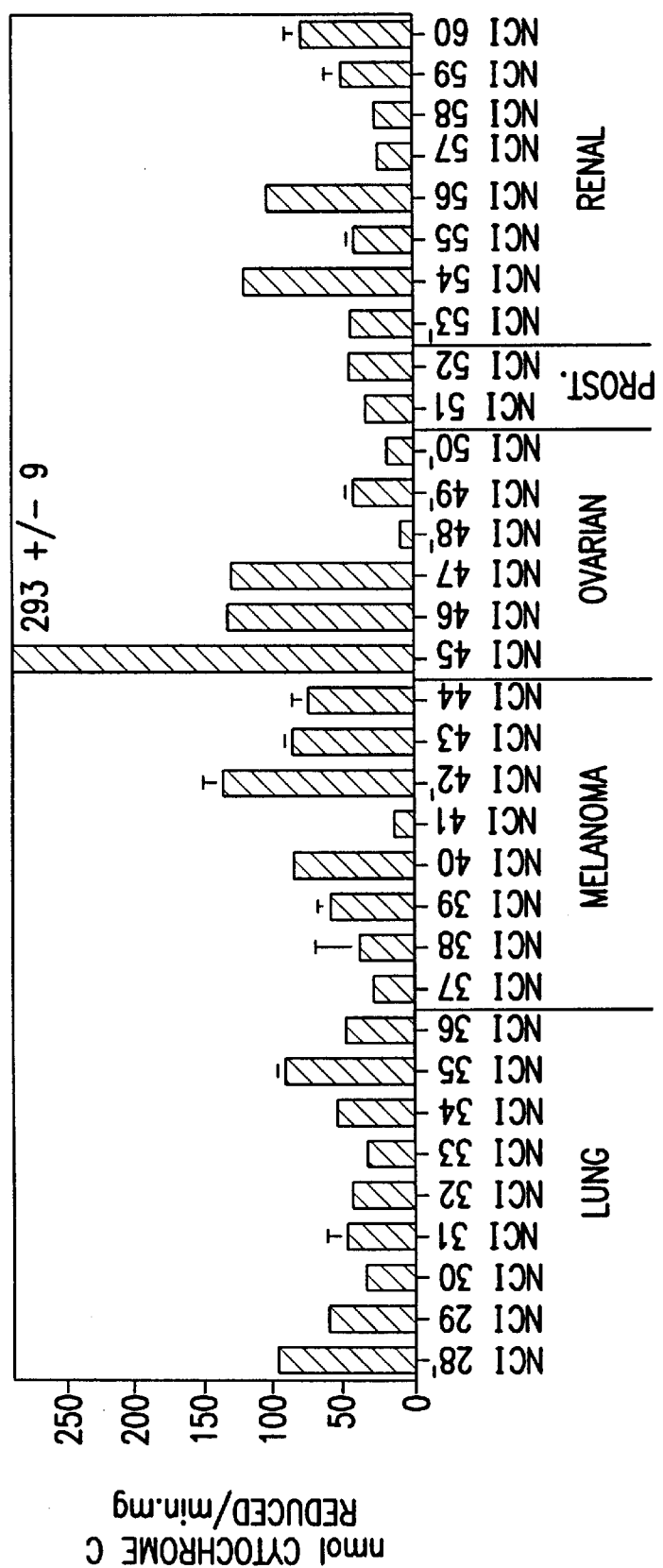

FIG. 10 is a bar graph depicting RED enzyme activity levels (rates of cytochrome C reduction) measured in a panel of 60 individual human tumor cell lines derived from human tumors originating in 9 different tissues. RED activity was determined in isolated cell microsomes by cytochrome C reduction. Data shown are mean±range for duplicate determinations. In most cases, error bars are <5% of the mean values and are too small to be seen in this graphical presentation. The 60 human tumor cell lines are derived from the nine indicated human tumor types and correspond to the panel of cell lines used by the U.S. National Cancer Institute in the In Vitro Anticancer Drug Discovery Screen Program (Boyd, M. R. and Paull, K. D., *Drug Develop Res.* 34:91–109 (1995)).

Figure 11A:
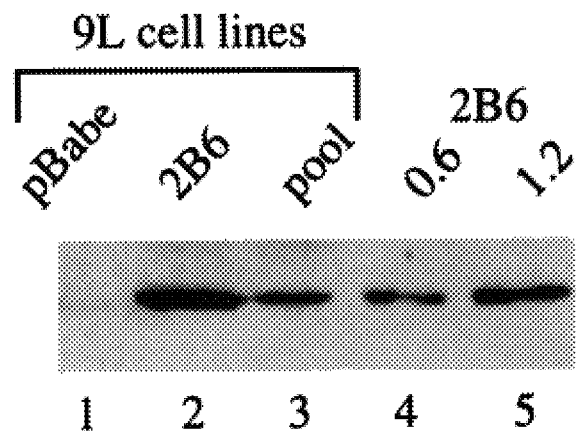
Figure 11B:
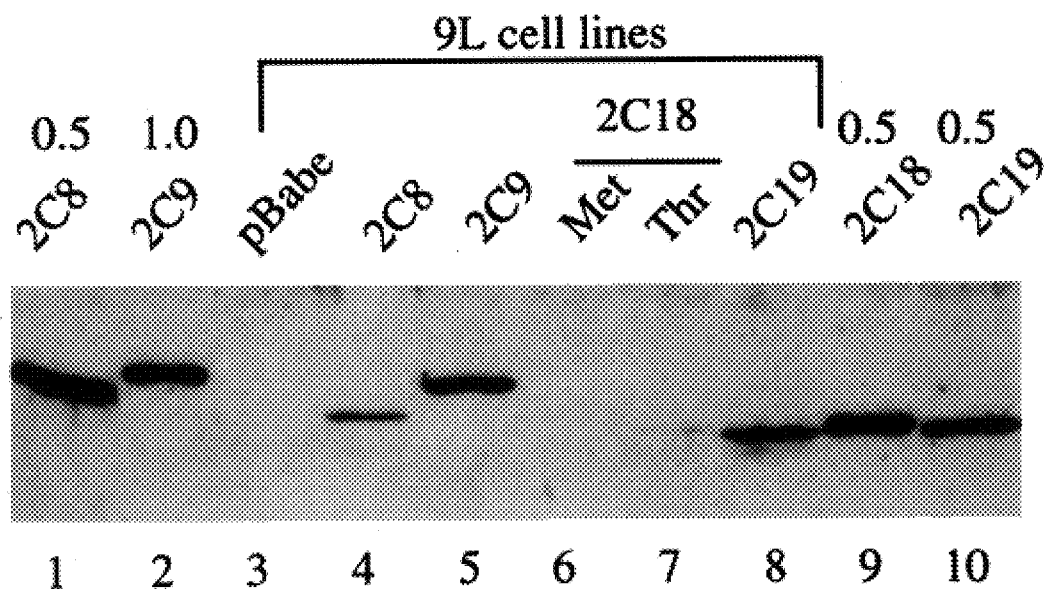

FIGS. 11A and 11B depict Western blot analyses of CYP protein levels in 9L/P450 cell lines. Shown are Western blots of microsomes isolated from wild-type 9L gliosarcoma cells (9L/wt) and 9L/P450 (9L cells transduced with each of the indicated human P450 genes) (60 $\mu$g/lane) probed with antibody to P450 2B6 (FIG. 11A) or P450 2C (FIG. 11B). Lane 3 in FIG. 11A shows 9L microsomes prepared from the original pool of retroviral 2B6 transduced cells, prior to selection of the 2B6 clone shown in lane 2. cDNA-expressed P450 2B6 (FIG. 11A, lanes 4, 5; lymphoblast expression) and cDNA-expressed P450 2C standards (FIG. 11B, lanes 1, 2, 9, 10; yeast expression) were analyzed in parallel at the indicated number of pmol P450 protein per well. Comparable band intensities were obtained for CYP2Cs expressed in lymphoblasts (Gentest). The anti-CYP2C COOH-terminal antibody used in this study (anti-FIPV-COOH) consistently gave stronger Western blot signals with cDNA-expressed 2C8 and lower signals with 2C9 compared with 2C18 and 2C19.

Figure 12:
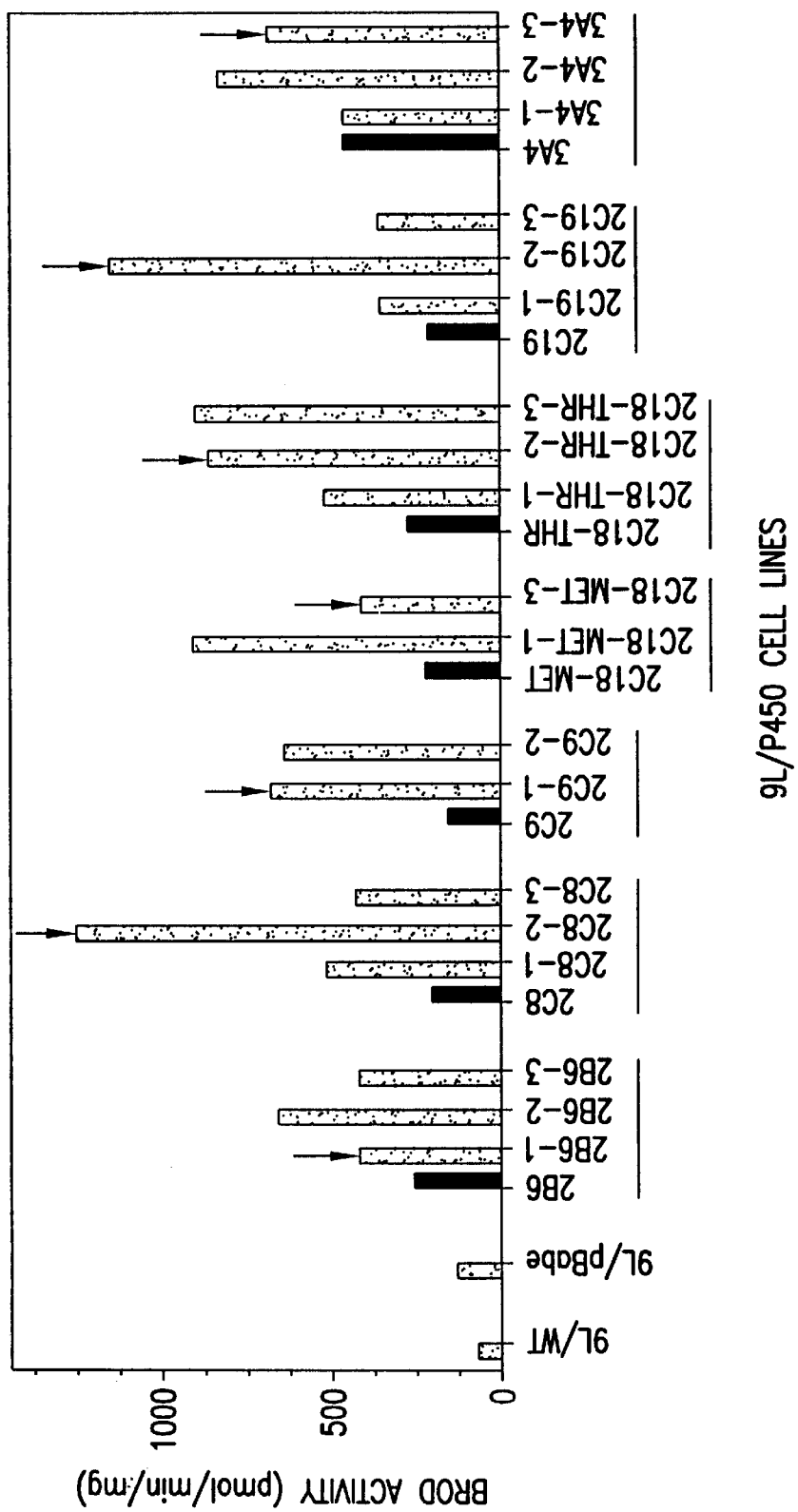

FIG. 12 depicts a bar graph of P450-catalyzed 7-benzyloxyresorufin O-deethylase (BROD) activity in each of the indicated 9L/P450 cell lines. Shown are BROD activity values measured in microsomes prepared from the original retroviral P450-infected 9L cell pools (black bars) or from individual clonal cell lines (designated −1, −2, −3 in this Figure) (speckled bars) selected on the basis of their enhanced sensitivity to CPA or IFA (see, Example 2). Vertical arrows indicate individual clones of each 9LlP450 pool selected for subsequent study.

Figure 13A:
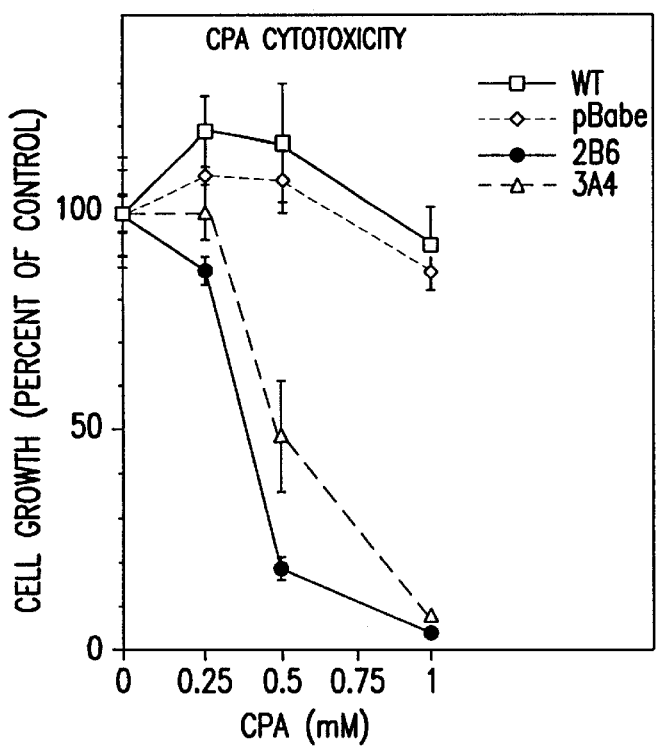
Figure 13B:
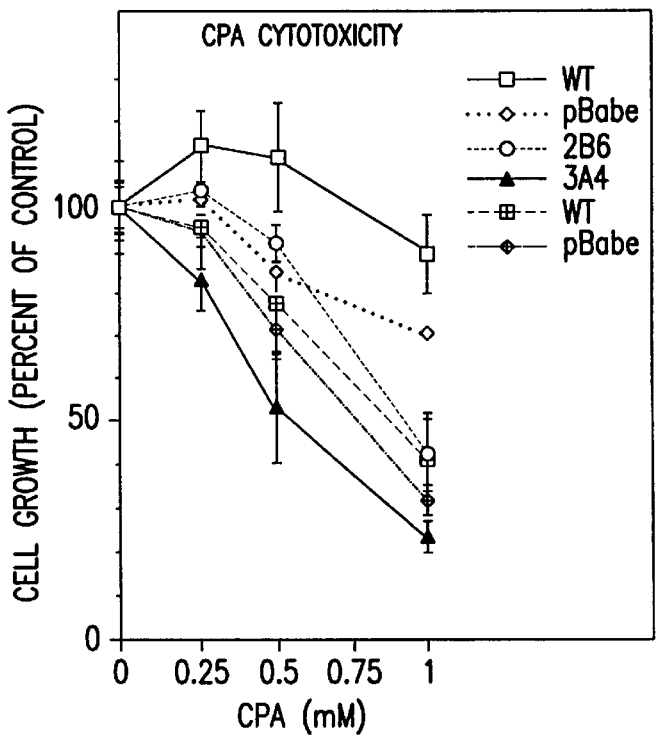
Figure 13C:
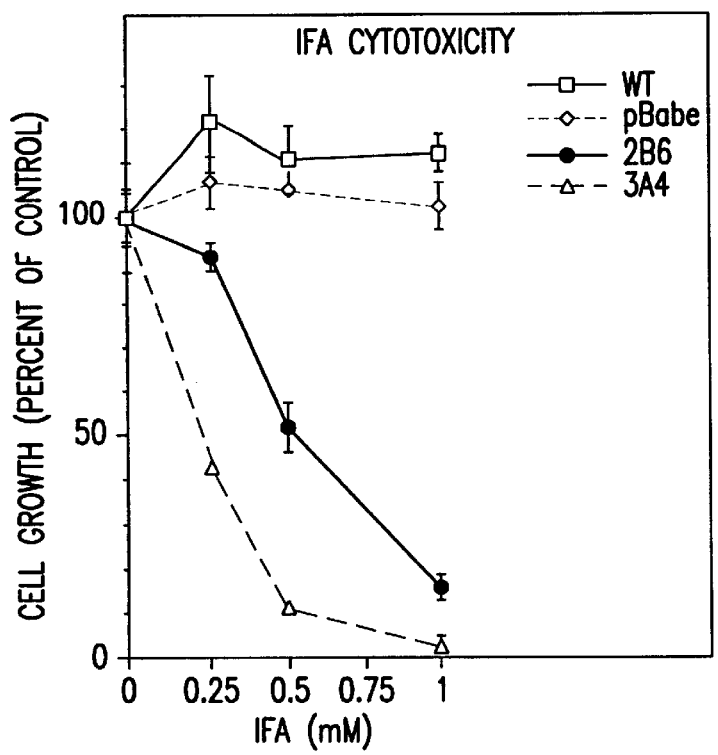
Figure 13D:
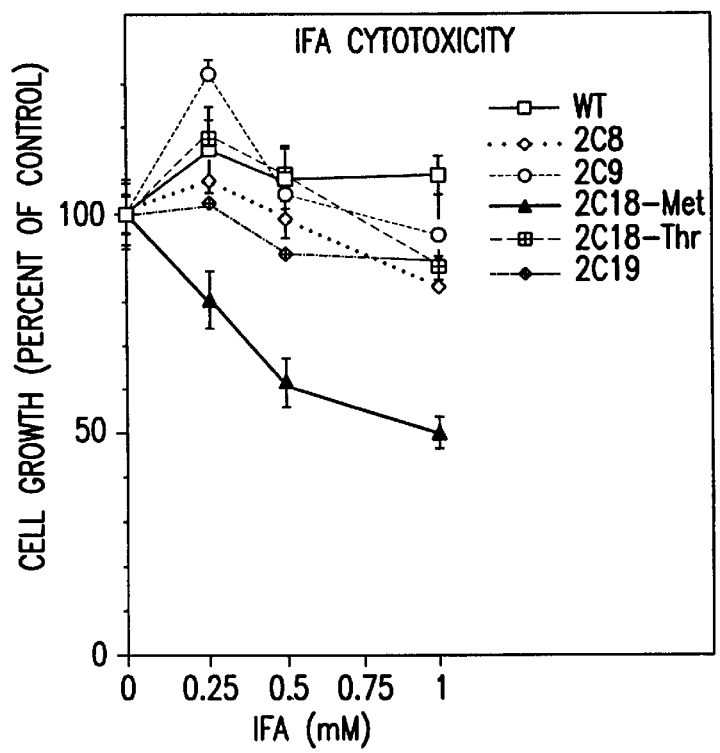

FIGS. 13A–13D depict the results of a growth inhibition assay to assess chemosensitization to CPA (FIGS. 13A and 13B) and IFA (FIGS. 13C and 13D) in 9L/P450 cells. Cells were seeded at 500 cells/well in 48-well plates and were treated with the indicated concentrations of CPA or IFA for 4 days. Control cells for each cell line received no drug treatment. Relative cell number at the end of the experiment was determined by crystal violet staining as described below in "Material and Methods" of Example 2. Data (mean±SD, n=3) are based on the crystal violet absorbance in drug-treated plates as a percent of the corresponding drug-free controls. Data for the P450-deficient control cell lines (9L/wt and 9L/pBabe) shown in FIGS. 13A and 13C are the same as shown in FIGS. 13B and 13D.

Figure 14:
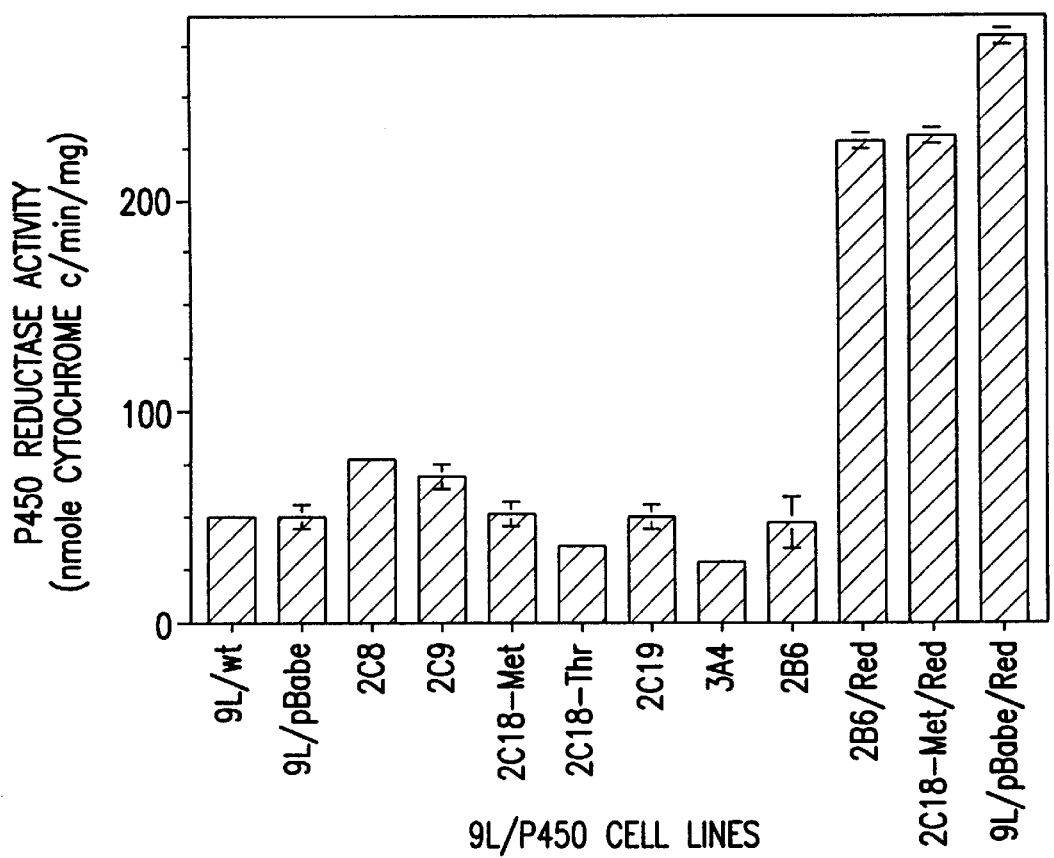

FIG. 14 is a bar graph depicting P450 reductase activity in 9L tumor/P450 cell lines. Microsomes prepared from each of the indicated cell lines were assayed for P450 reductase activity (cytochrome C reduction) as described below in the "Materials and Methods" section of Example 2. Cell lines transduced with P450 reductase are designated "Red". Data shown are mean±SD, based on n=3 determinations.

Figure 15A:
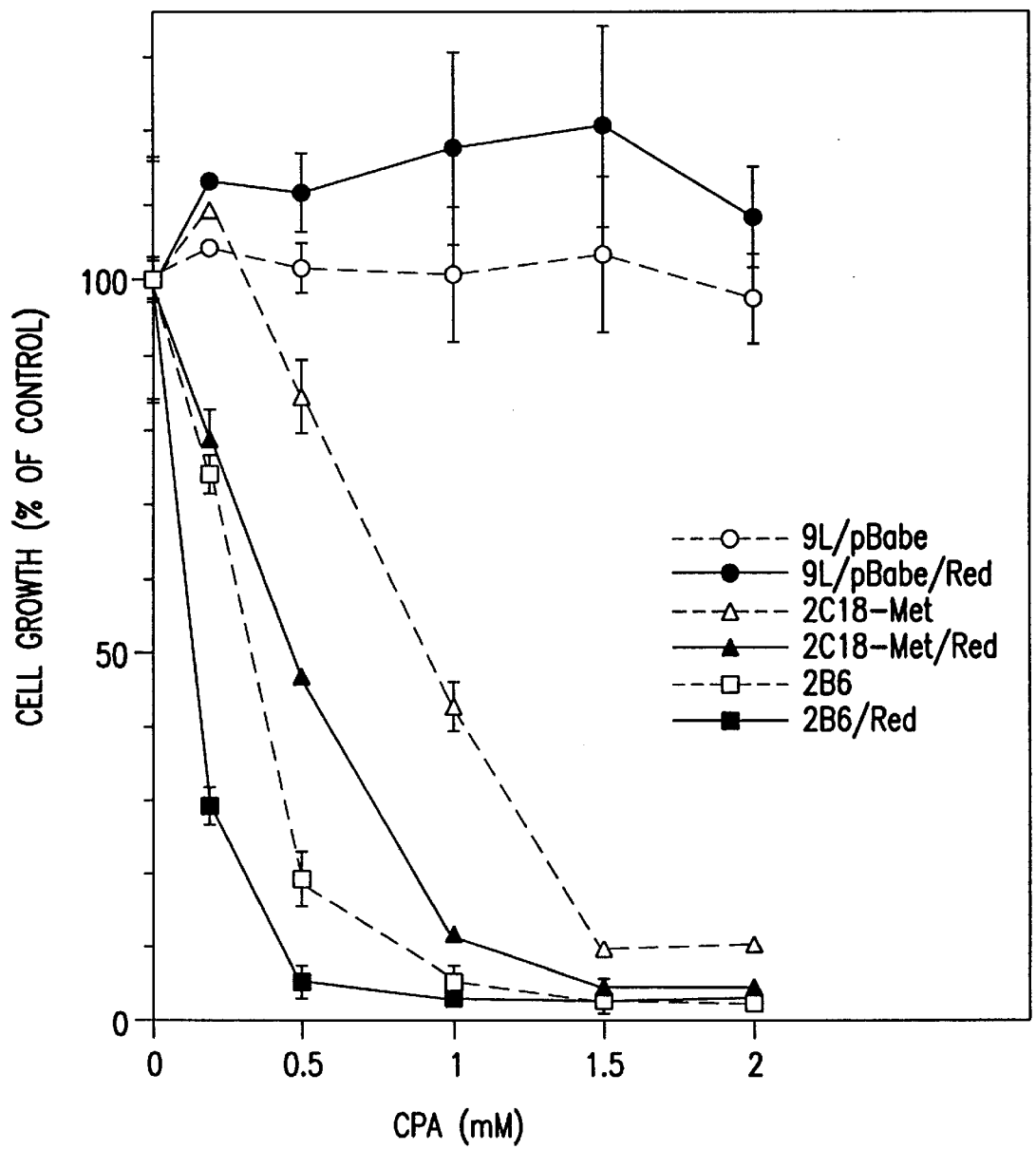
Figure 15B:
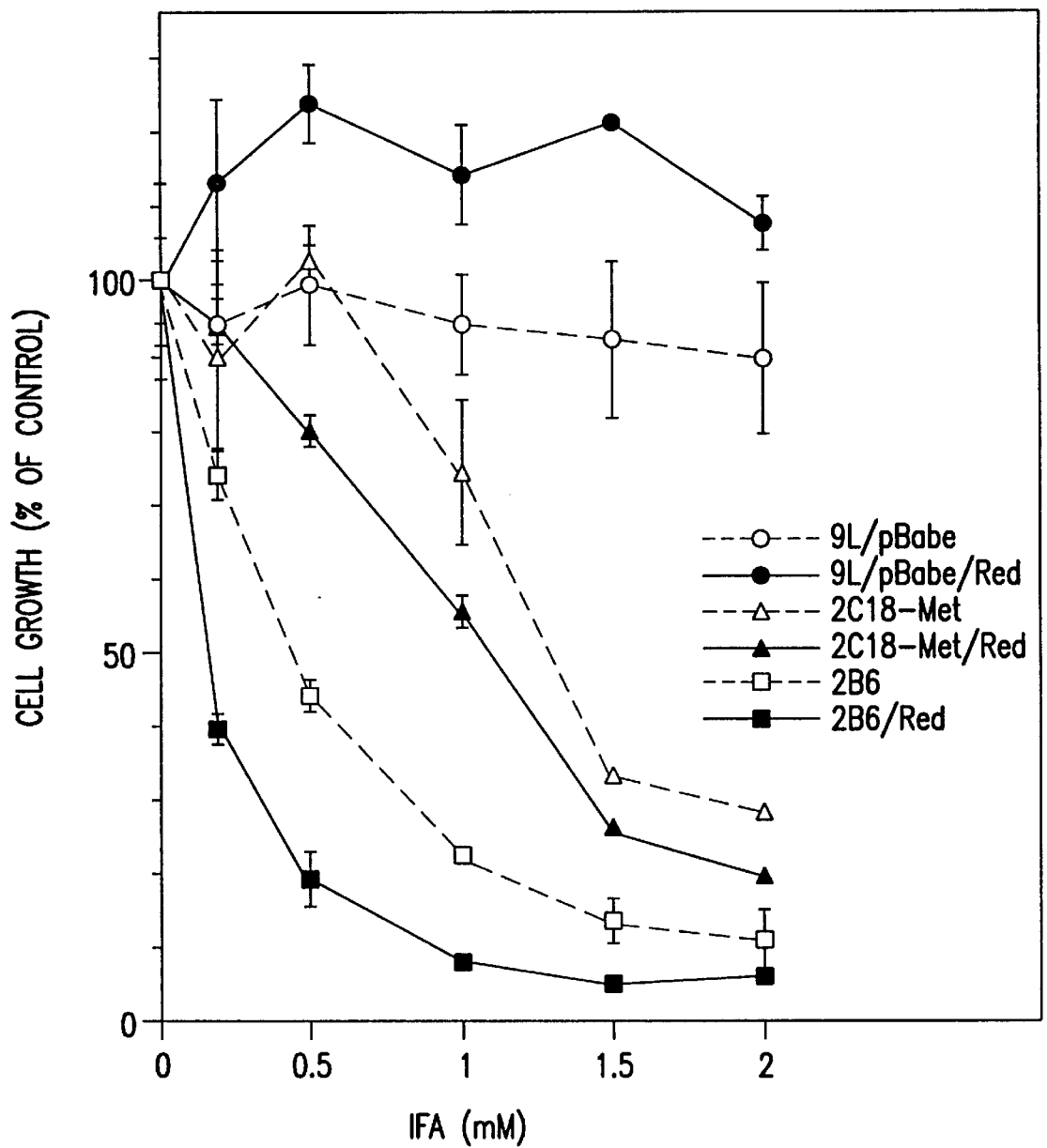

FIGS. 15A and 15B are graphs depicting that retroviral transduction of the P450 reductase gene enhances P450-mediated CPA and IFA cytotoxicity. 9L/pBabe cells and 9L cells transduced with P450 and /or P450 reductase ("Red") were seeded at 4000 cells/well in 48-well plates and treated with increasing concentrations of CPA (FIG. 15A) or IFA (FIG. 15B) for 4 days. Cell growth in comparison to drug-free controls was determined by crystal violet staining and is presented as mean±SD for n=3 replicates.

Figure 16:
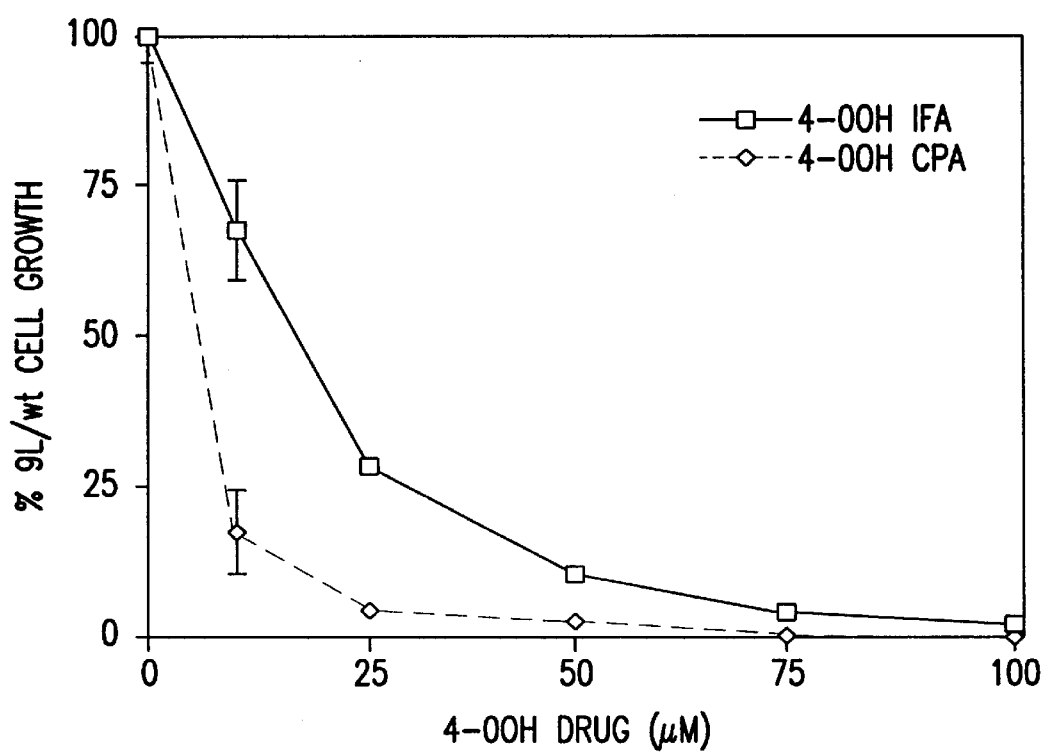

FIG. 16 is a graph depicting the intrinsic chemosensitivity of 9L/wt cells to chemically activated CPA and IFA. 9L/wt cells seeded at 2000 cells/ well in 48-well plates were treated for 3–4 hours with increasing concentrations of 4-hydroperoxy-CPA or 4-hydroxyperoxy-IFA (0 to 100 $\mu$M). Cells were then incubated in fresh drug-free media and allowed to grow for 4 days. Cell growth as a percent of drug-free controls was then determined by crystal violet staining. Data shown are mean±range for duplicate samples.

Figure 17:
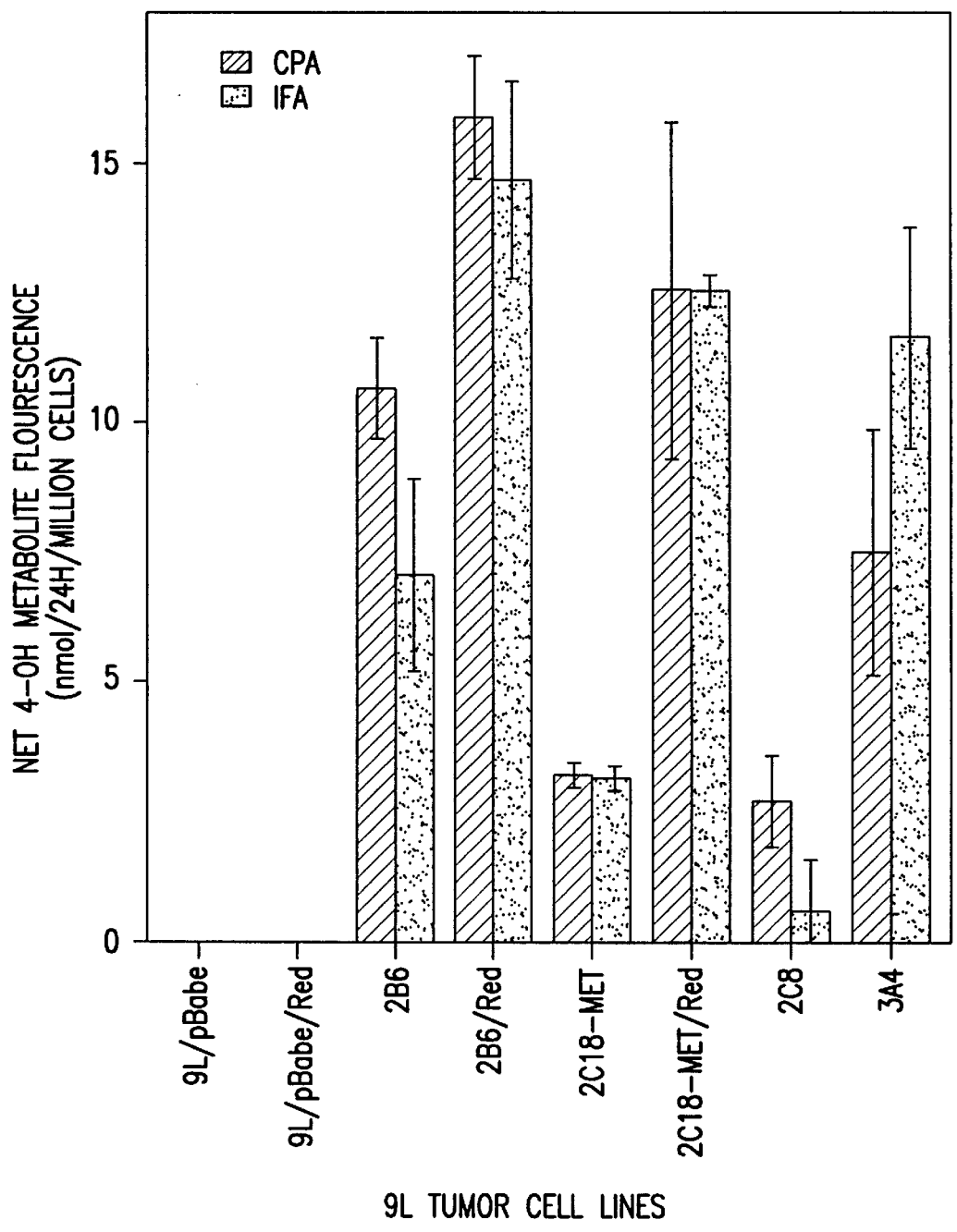

FIG. 17 is a bar graph depicting semicarbazide trapping/ fluorescence assay for 4-hydroxy metabolites in cell culture. Each of the indicated 9L cell lines was seeded on a 48-well plate in duplicate at $2\times10^4$ cells/well. 24 hours later, 2 mM CPA (hatched bars) or 2 mM IFA (solid bars) was added to the cells together with 5 mM semicarbazide (final concentration) in a volume of 1 ml. The culture media was analyzed for 4-hydroxy-CPA or 4-hydroxy-IFA 24 hours after drug addition. Data shown is normalized to the total cell number in each well, as described in the "Material and Methods" section of Example 2. Background fluorescence observed in 9L/Babe cells was subtracted from each sample.

Figure 18A:
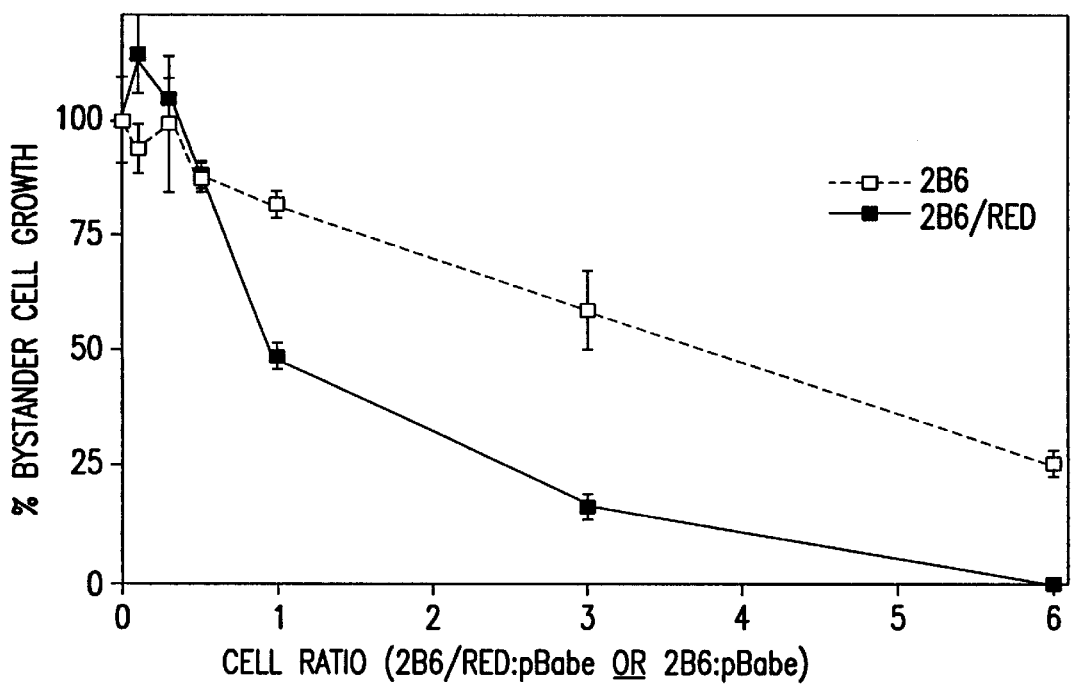
Figure 18B:
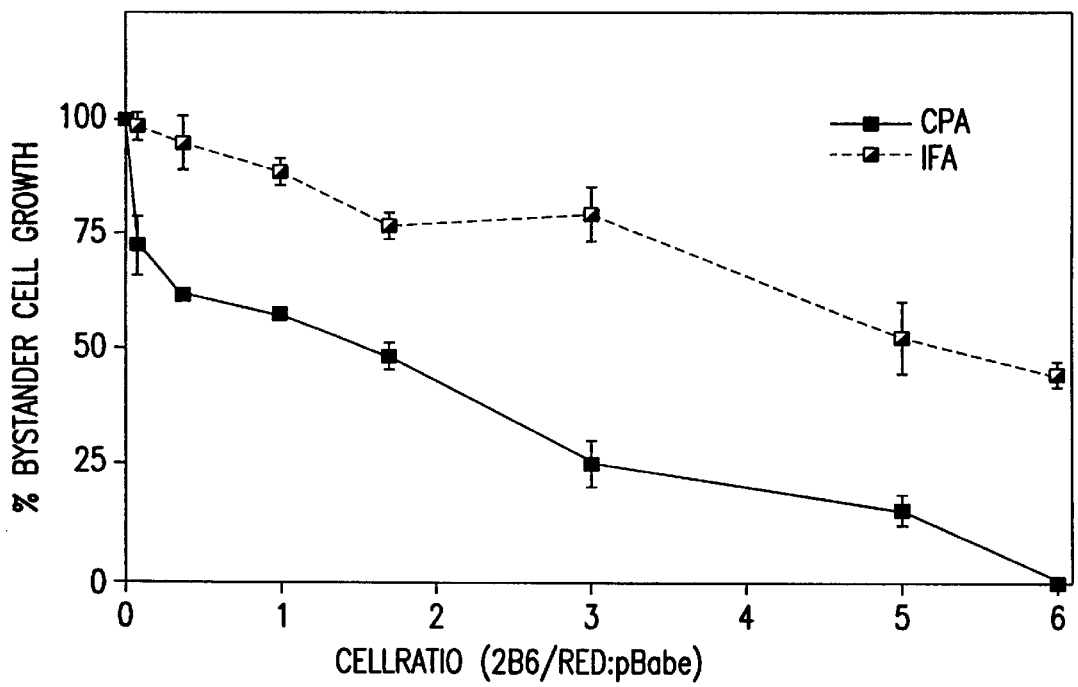

FIGS. 18A and 18B are graphs depicting the bystander cytotoxicity of 9L/2B6/reductase and 9L/2B6 cells. In FIG. 18A, bystander cytotoxicity of 9L/2B6/reductase cells is compared to that of 9L/2B6 cells. In both cases, 9L/pBabe served as the bystander cells. 9L/pBabe cells were plated in duplicate at $10^5$ cells/well of a 6-well plate (lower chamber). 9L/2B6/reductase cells or 9L/2B6 cells were plated in 25 mm cell culture inserts (upper chamber) at concentrations ranging from $10^4$ to $6\times10^5$ cells, corresponding to ratios of 0.1 to 6 relative to the bystander 9L/pBabe cells growing in the lower chamber, as shown on the x-axis. Cells were incubated in a total volume of 3 ml Dulbecco's minimal essential medium (DMEM), 10% FBS, containing 1 mM CPA, final CPA concentration.

FIG. 18B depicts a comparison of the bystander cytotoxicity of 9L/2B6/reductase cells to 9L/pBabe cells using either CPA or IFA as prodrug. The experimental design was the same as in FIG. 18A, except that the final drug concentration was 0.67 mM. Data shown for both panels correspond to the survival of 9L/pBabe bystander cells in the lower chamber.

FIGS. 19A–19D are graphs depicting the results of a tumor growth delay assay in severe combined immunodeficiency (scid) mice bearing 9L/pBabe, 9L/2B6/reductase, and 9L/2C18-Met/reductase solid tumors. Shown are the effects of CPA treatment on growth of 9L/pBabe tumors growing on the left flank of scid mice that also bear either a 9L/2B6/reductase tumor (FIG. 19A) or a 9L/2C18-Met/ reductase tumor ((FIG. 19C)) on the right flank. Also shown are the effects of CPA on growth of 9L/2B6/reductase (FIG. 19B) or 9L/2C18-Met/reductasetumors ((FIG. 19D)) in these same mice. Tumor areas were measured twice a week with Vernier calipers. The arrows above the x-axis in each panel indicate the days on which CPA was given by intraperitoneal (i.p.) injection at 150 mg/kg, as described in the "Materials and Methods" section of Example 2. Data shown is mean tumor area (mm$^2$)±SEM for n=4 tumors per treatment group. Mice not treated with CPA died earlier than the CPA-treated mice, as indicated by the earlier decrease in number of remaining mice from n =4 (initial number of mice/group) to n=3, 2, or 1. Open circles indicate CPA-treated mice; closed circles indicate saline controls.

Figure 20A:
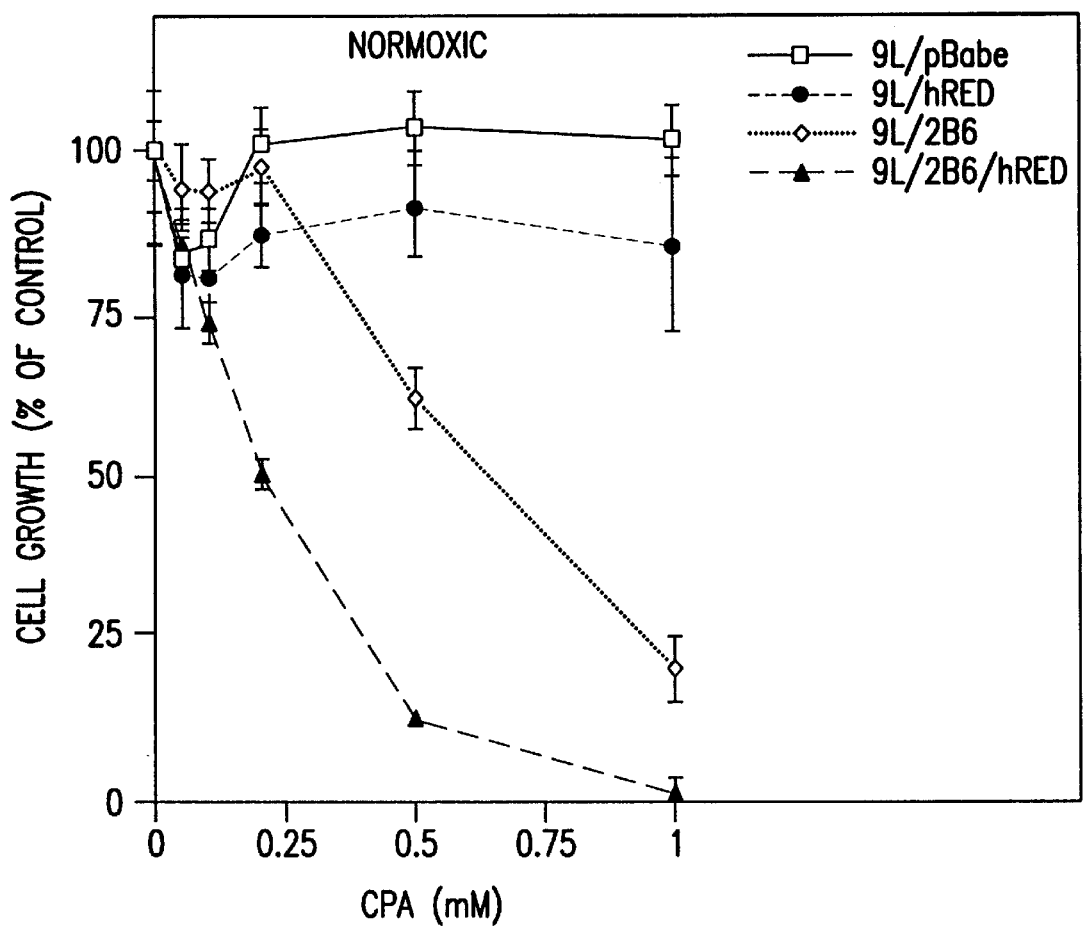
Figure 20B:
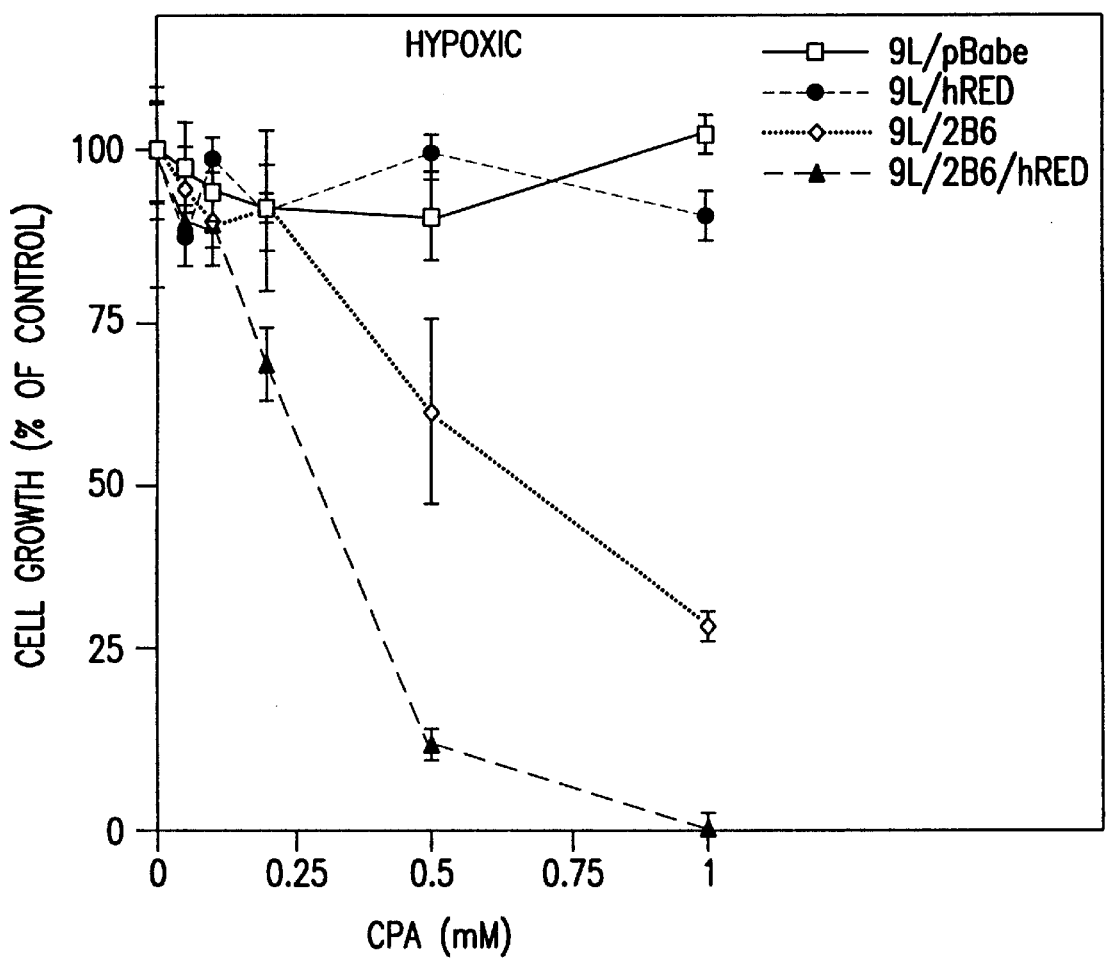

FIGS. 20A and 20B are graphs depicting that retroviral transduction of the human P450 reductase gene (HRED) enhances the cytotoxicity of CPA to cultured 9L gliosarcoma cells transduced with the P450 2B6 gene, both under normoxic culture conditions (FIG. 20A) and hypoxic culture conditions (FIG. 20B). Cells were seeded at 4000 cells/well in 48-well plates and treated with increasing concentrations of CPA for 4 days. Cell growth in comparison to drug-free controls was determined by crystal violet staining and is presented as mean±SD for n=3 replicates.

Figure 21:
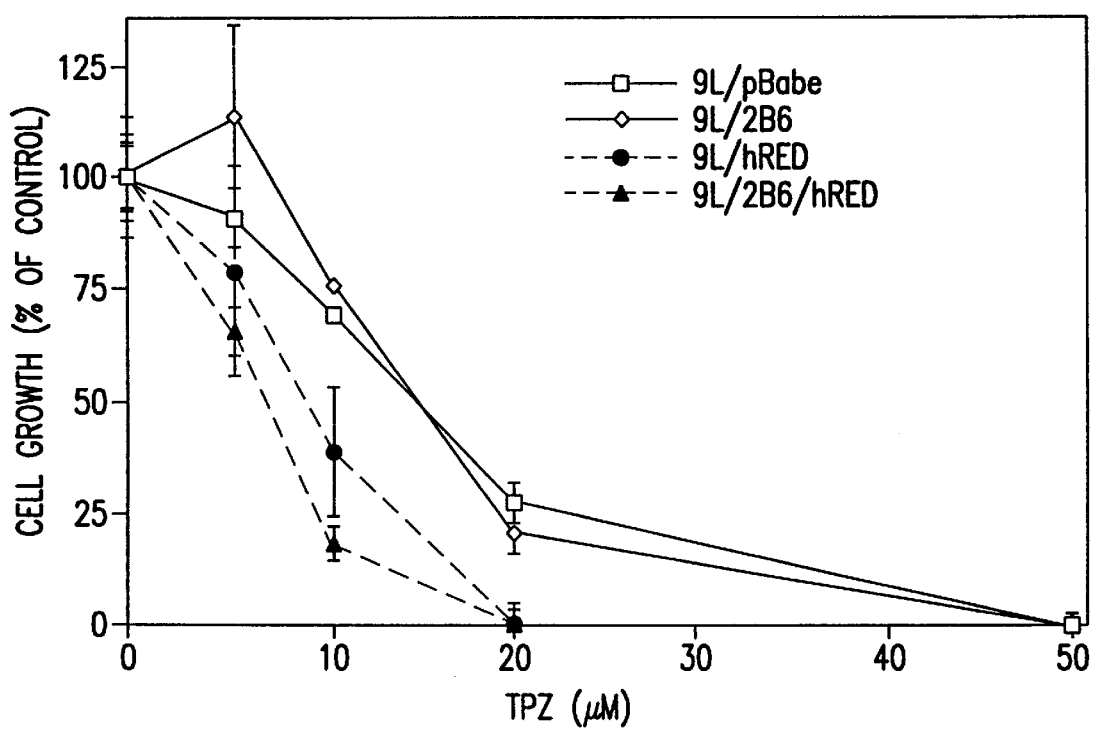

FIG. 21 is a graph depicting the cytotoxic effects of the bioreductive drug TPZ toward 9L/pBabe control cells and 9L cells transduced with retroviruses encoding human RED and/or P450 2B6 under normoxic culture conditions. Cells were seeded at 4000 cells/well in 48-well plates and treated with increasing concentrations of TPZ for 4 days. Cell growth in comparison to drug-free controls was determined by crystal violet staining and is presented as mean±SD for n=3 replicates.

Figure 22:
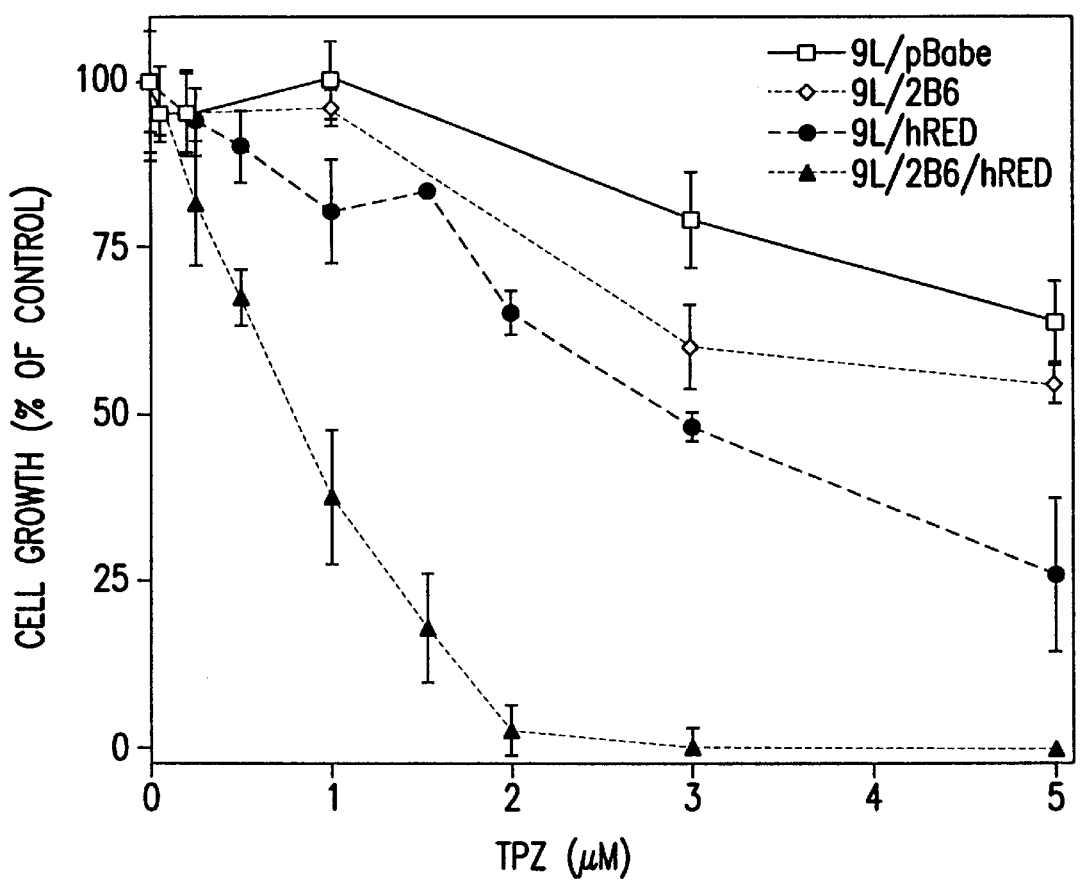

FIG. 22 is a graph depicting the cytotoxicity of increasing concentrations of TPZ under hypoxic conditions (1% $O_2$) toward 9L tumor cells transduced with retroviruses encoding P450 2B6 and/or human RED. 9L/pBabe cells served as controls. Cells were seeded at 4000 cells/well in 48-well plates and treated with increasing concentrations of TPZ for 4 days. Cell growth in comparison to drug-free controls was determined by crystal violet staining and is presented as mean±SD for n=3 replicates.

Figure 23:
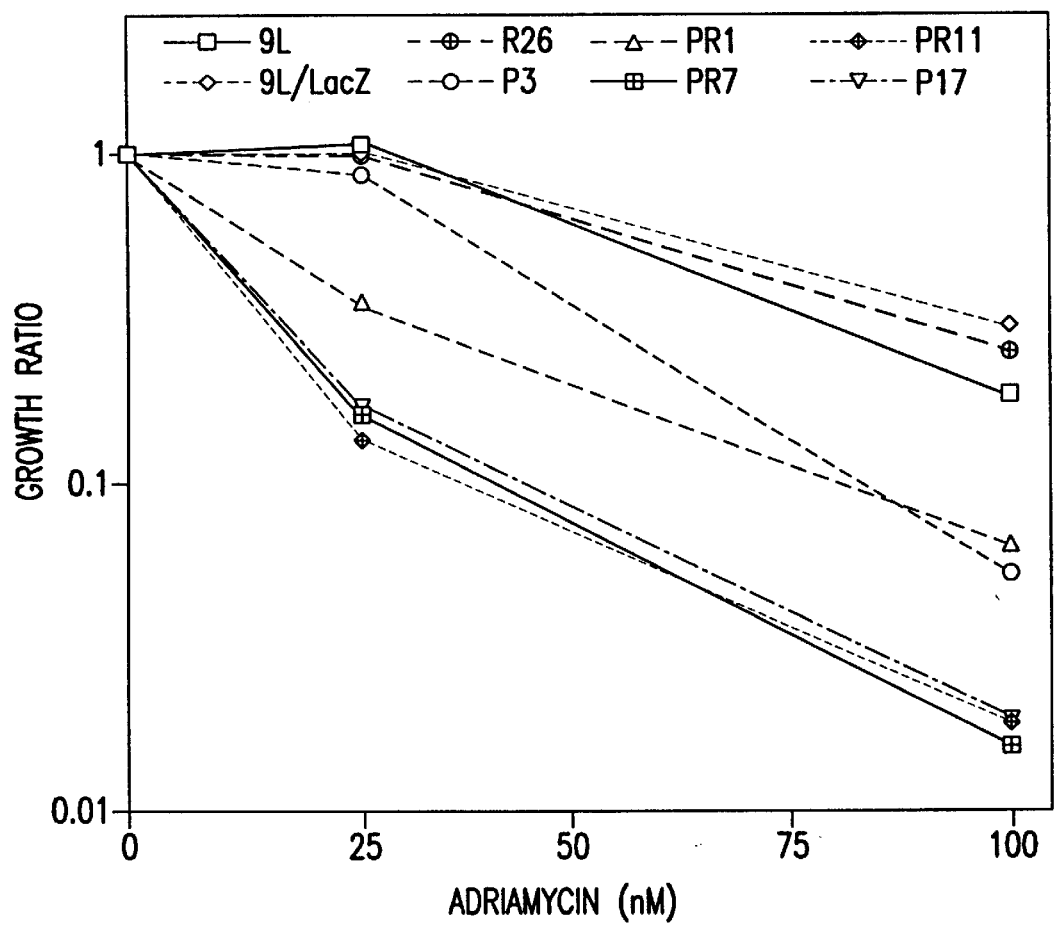

FIG. 23 depicts a graph showing the enhanced cytotoxicity of Adriamycin to 9L tumor cells expressing P450 2B1 in combination with rat RED.

The indicated 9L, 9L/2B1 and 9L/2B1/RED clonal cell lines, described in Example 1, were treated with Adriamycin for 2 days at the indicated drug concentrations. Cytotoxicity was measured after 5 days continuous culture using a growth inhibition assay, as described under FIG. 2B of Example 1. Enhanced cytotoxicity was seen in two independent cell lines which over-express RED approximately 5-fold (lines PR11 and PR7; see Table 1) in combination with P450 expression. A more modest chemosensitization is seen in the case of the cell line PR1, where the extent of RED overexpression is only approximately 2-fold (Table 1). Data shown are averages of duplicates.

Figure 24A:
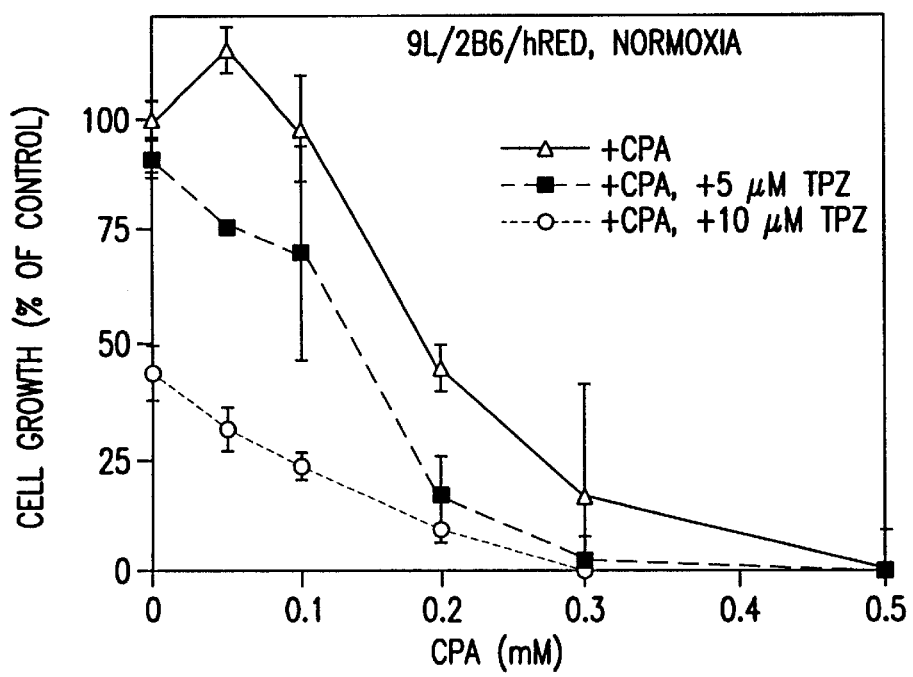
Figure 24B:
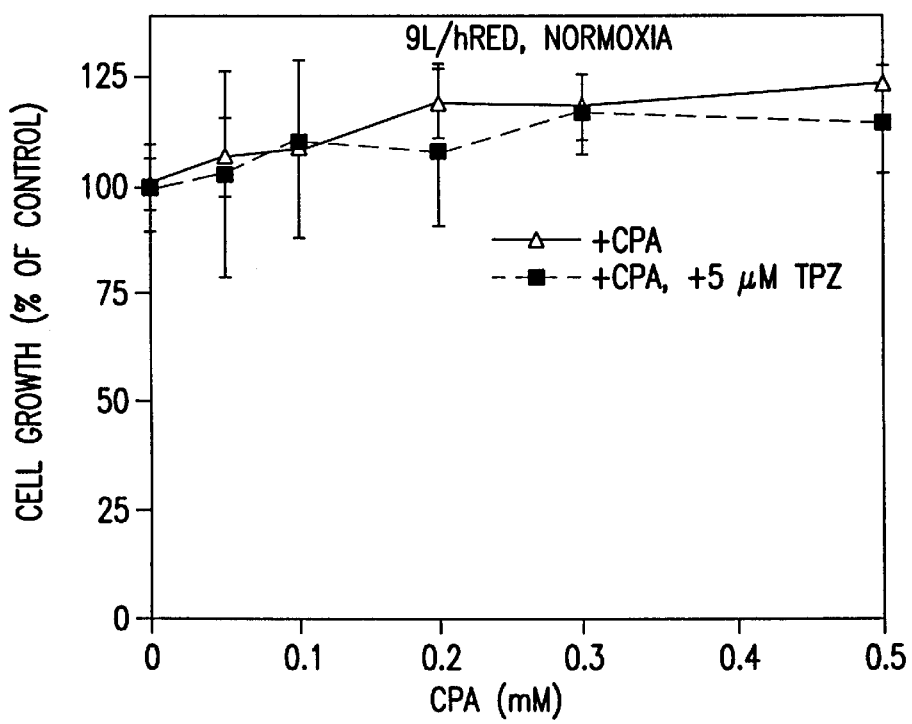
Figure 24C:
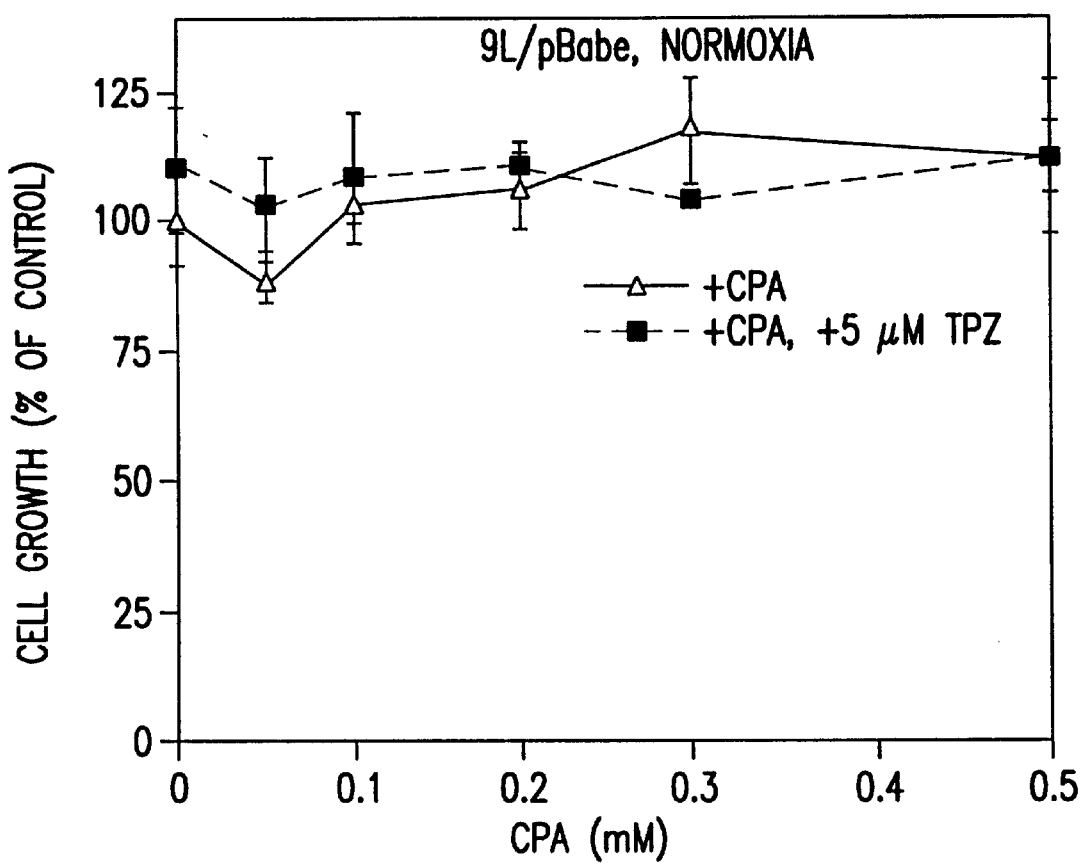

FIGS. 24A, 24B and 24C are graphs depicting the cytotoxic effects of TPZ (5 or 10 µM, as indicated) in combination with increasing concentrations of CPA under normoxic culture conditions (19.6% $O_2$, 5% $CO_2$). The data shown were obtained using 9L/2B6/hRED cells (FIG. 24A), 9L/hRED cells (FIG. 24B) and 9L/pBabe (control) cells (FIG. 24C). Data were compared to the cytotoxicity of increasing concentrations of CPA alone (i. e., in the absence of TPZ) measured using the same pools of tumor cells. Cells were seeded at 4000 cells/well in 48-well plates and then treated with the indicated drug concentrations for 4 days. Cell growth in comparison to drug-free controls (i.e., in the absence of CPA and TPZ) was determined by crystal violet staining and is presented as mean±SD for n=3 replicates.

Figure 25A:
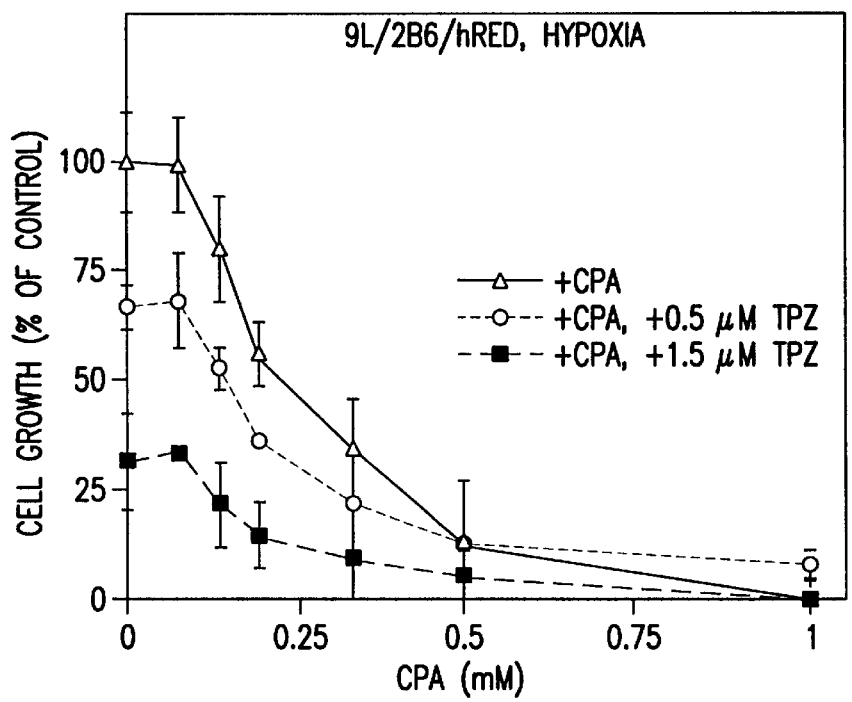
Figure 25B:
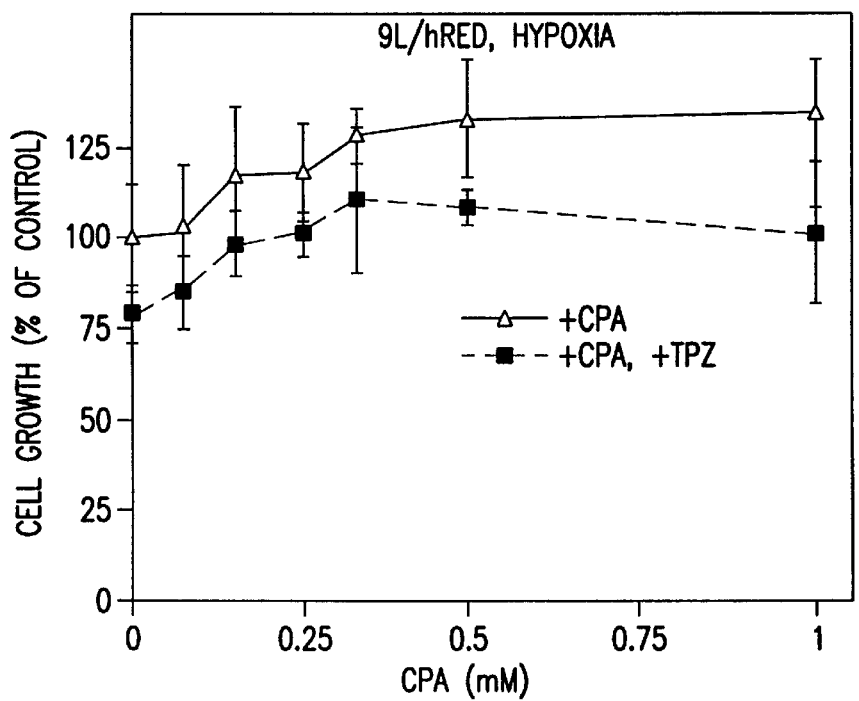
Figure 25C:
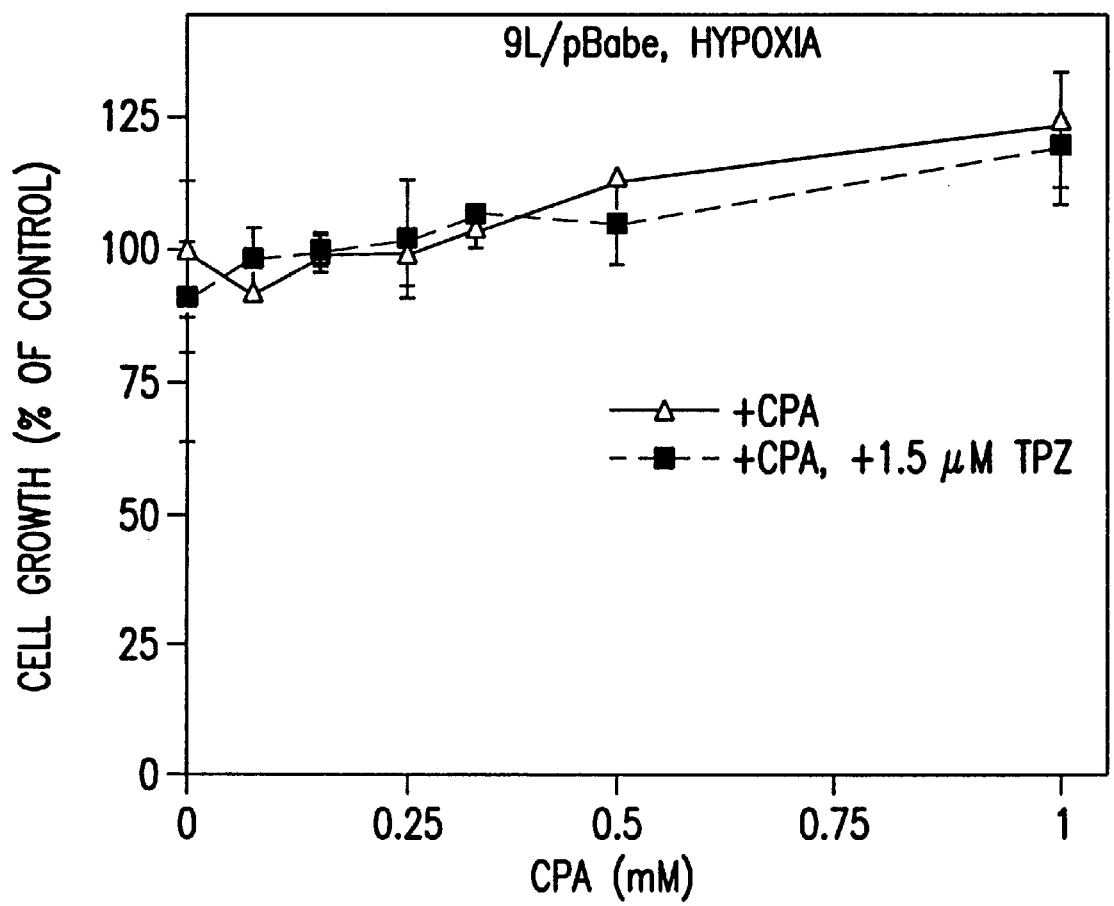

FIGS. 25A, 25B and 25C are graphs depicting the cytotoxic effects of TPZ (0.5 or 1.5 µM, as indicated) in combination with increasing concentrations of CPA under hypoxic culture conditions (1% $O_2$, 5% $CO_2$). The data shown were obtained using 9L/2B6/hRED cells (FIG. 25A), 9L/hRED cells (FIG. 25B) and 9L/pBabe (control) cells (FIG. 25C). Data were compared to the cytotoxicity of increasing concentrations of CPA alone (i.e., in the absence of TPZ) measured using the same pools of tumor cells. Cells were seeded at 4000 cells/well in 48-well plates and then treated with the indicated drug concentrations for 4 days. Cell growth in comparison to drug-free controls (i.e., in the absence of CPA and TPZ) was determined by crystal violet staining and is presented as mean±SD for n=3 replicates.

DETAILED DESCRIPTION OF THE PREFERRED EMBODIMENTS

The present invention is directed to the killing of neoplastic cells using cytochrome P450-based gene therapy in combination with gene transfer of the cytochrome P450 reductase (RED) enzyme. The present invention is also directed to the transfer of the cytochrome P450 and RED gene products to neoplastic cells.

By "neoplastic cells" is intended cells whose normal growth control mechanisms are disrupted (typically by accumulated genetic mutations), thereby providing the potential for uncontrolled proliferation. The term is intended to include both benign and malignant neoplastic cells in both the central nervous system and the periphery. As used herein, the term "periphery" is intended to mean all other parts of the body outside of the brain or spinal cord.

For purposes of the invention, neoplastic cells include cells of tumors, neoplasms, carcinomas, sarcomas, papillomas, leukemias, lymphomas, and the like. Of particular interest are solid tumors that may arise in any organ or tissue of the mammalian body.

By "cytochrome P450 gene" (alternatively referred to as "CYP" or "P450") is intended a gene encoding any member of the cytochrome P450 superfamily of enzymes (Nelson, D. R., et al., *Pharmacogenetics* 6:1–42 (1996)) that is capable of activating an anti-cancer drug (LeBlanc, G. A. and Waxman, D. J., *Drug. Metab. Rev.* 20:395–439 (1989); Kivisto, K. T., et al., *Br. J. Clin. Pharmacol.* 40:523–530 (1995)). By "activating or bioactivating an anti-cancer drug" is intended any metabolic reaction that increases the cytotoxic or cytostatic activity or otherwise increases the therapeutic efficacy of an anti-cancer drug; or that confers on the drug an additional mechanism of action beyond that which the drug exhibits in the absence of the metabolic reaction.

Exemplary P450 genes include mammalian genes P450 1A1, 1A2, 1B1, 2B1, 2B2, 2B4, 2B5, 2B6, 2B11, 2A6, 2C6, 2C8, 2C9, 2C11, 2C18, 2C19, 2D6, 2E1, 3A4, 3A5, 3A7, or 4B1, as well as members of corresponding P450 gene families and subfamilies in other species, whose cDNA sequences are known (Nelson, D. R., et al., *Pharmacogenetics* 6:1–42 (1996)), or any other P450 gene, including their allelic variants, site-specific mutants, and chimeric constructs (e.g., Chang, T. K. H., et al., *Pharmacogenetics* 7:211–221 (1997); Szklarz, G. D., et al., Biochemistry 34:14312–14322 (1995); He, Y. A., et al., *Biochemistry* 36:8831–8839 (1997)). Mammalian cytochrome P450 genes are preferred. The rat cytochrome P450 2B1 gene and the human cytochrome P450 2B6, 2C18, and 3A4 genes are particularly preferred.

The cytochrome P450 system consists of two protein components: the heme-containing P450 protein and the flavoprotein NADPH-cytochrome P450 reductase (alternatively known as "RED"). Both proteins are embedded in the phospholipid bilayer of the endoplasmic reticulum. RED is an FAD- and FMN-containing flavoenzyme that is encoded by a single gene (Porter, T. D., et al., *Biochemistry* 29:9814–9818 (1990); O'Leary, K. A., et al., *Arch. Biochem. Biophys.* 310:452–459 (1994)), and catalyzes the transfer of electrons required for all microsomal P450-dependent enzyme reactions, including drug activation (Porter, T. D., *Trends in Biochemical Sciences* 16:154–158 (1991); Strobel, H. W., et al., "*NADPH Cytochrome P450 Reductase and Its Structural and Functional Domains*" in: *Cytochrome P450: Structure, Mechanism, and Biochemistry,* P. R. Ortiz de Montellano, ed., Plenum Press, New York, Second Edition, pages 225–244 (1995)). Detailed studies of the electron transfer mechanism have established that a total of two electrons from NADPH are transferred, first to FAD and then to FMN, before being transferred one at a time to the P450 hemeprotein (Vermilion, J. L., et al.,*J. Biol. Chem.* 256:266–277 (1981)). Cytochrome P450, in turn, utilizes these reducing equivalents for various monooxygenase reactions, including the hydroxylation reactions associated with the activation of CPA and other anti-cancer drugs. In some cases, particularly under hypoxic conditions where cellular oxygen concentrations are low, cytochrome P450 enzymes catalyze the transfer of electrons directly to drugs and other foreign chemicals, rather than to oxygen. This xenobiotic reductase activity of cytochrome P450 can lead to the activation of a number of anticancer agents (Goeptar, A. R., et al., *Crit. Rev. Toxicol.* 25:25–65 (1995)).

By "gene encoding RED" is intended a gene encoding the enzyme NADPH-cytochrome P450 reductase. The RED gene may be from any species. RED cDNA from many species are known to those skilled in the art, and their nucleotide sequences can be obtained from the GenBank Sequence Database. Representative examples from GenBank include accession numbers S90469 (human), GPICYPOR (guinea pig), RATCYPRM (rat), and CRUNADPH (hamster).

The term "gene product" or "product of a particular gene" broadly refers to polypeptides or proteins encoded by a particular gene, but may also include transcription products of the particular gene.

By "chemotherapeutic agent that is activated by the product of said cytochrome P450 gene" is meant a pharmaceutical agent that can be used in the treatment of neoplasms, and that is capable of being activated by cytochrome P450. By "activating" or "bioactivating" achemotherapeutic agent is intended any metabolic reaction that increases the cytotoxic or cytostatic activity or otherwise increases the therapeutic efficacy of the agent; or that confers on the agent an additional mechanism of action beyond that which the agent exhibits in the absence of the metabolic reaction. By "cytotoxic" or "cytostatic" is intended causing or leading to cell death or slower tumor cell growth. Examples of P450-activated chemotherapeutic agents are cyclophosphamide, ifosfamide, dacarbazine, procarbazine, thio-TEPA, etoposide (VP-16), 4-ipomeanol, 2-aminoanthracene, or tamoxifen. Other P450-activated chemotherapeutic agents known to those skilled in the art can also be used in the present invention.

By "treating said neoplastic cells with a chemotherapeutic agent" is intended to include both the local delivery of the prodrug into or near the site of the tumor by, e.g., slow-release pellets, as well as the systemic administration of the chemotherapeutic agent, i.e., through intraperitoneal, intravenous, parenteral, or intramuscular routes. Localized delivery of the drug is expected to increase the fraction of the drug activated within the tumor, and thus increase drug efficacy.

Dosages of a particular chemotherapeutic agent may be administered according to current standard clinical practice. See, e.g., Hubbard, S. M. and Jenkins, J. F., "Chemotherapy Administration: Practical Guidelines" in *Cancer Chemotherapy: Principles and Practice,* Chabner and Collins, eds., J. B. Lippincott Company, Philadelphia, Pa. (1990), pages 449–463. For example, standard clinical dosages for CPA in adults range from approximately 600–1000 mg/meter$^2$ (m$^2$) (Struck, R. F., et al., *Cancer Research* 47:2723–2726 (1987); standard daily dosages for IFA range from approximately 1 to 3 grams/m$^2$ (Kurowski, V. and Wagner, T., *Cancer Chemother. Pharmacol.* 33:36–42 (1993)). Standard clinical practice may involve body surface area (BSA)-based dose calculations, as well as individualization of dosages based on pharmacokinetic optimization using plasma drug and metabolite concentrations ("therapeutic drug monitoring" or TDM). Such concentrations may be obtained using limited sampling or other pharmacokinetic sampling and modeling techniques (van Warmerdam, L. J., et al., *Neth J. Med.* 51:30–35 (1997); Desoize, B. and Robert, J., *Eur. J. Cancer* 30A:844–851 (1994); Gurney, H., *J. Clin. Oncol.* 14:2590–2611 (1996)). Other factors, known to those skilled in the art, such as the clinical status and age of the patient, will also contribute to dosage adjustment.

The invention also provides preferred embodiments of the foregoing methods wherein the cytochrome P450 gene is P450 2B1, P450 2B6, or P450 2C18 and the chemotherapeutic agent is CPA; and wherein the cytochrome P450 gene is P450 2B1 or P450 3A4 and the chemotherapeutic agent is ifosfamide.

Another embodiment of the present invention relates to cytochrome P450/RED gene therapy with treatment regimens utilizing chemotherapeutic agents that are activated by P450 (e.g., CPA, IFA), in further combination with bioreductive drugs, which are activated through reductive metabolism catalyzed by P450 and/or RED. Thus, in a representative example of this embodiment, following cytochrome P450/RED gene therapy, a chemotherapeutic agent, such as CPA, is administered along with a bioreductive drug, such as tirapazamine. The order of the administration of the two drugs is not critical. Alternatively, the bioreductive drug can be used alone (i.e., without CPA).

As used herein, "bioreductive drugs" are drugs that undergo metabolic reduction, catalyzed by P450 reductase ("RED") and/or cytochrome P450, to generate cytotoxic or cytostatic metabolites under either hypoxic or normoxic conditions. Examples of bioreductive drugs include Adriamycin, porfiromycin, mitomycin C, tirapazamine (TPZ or SR 4233), indoloquinone E09, aziridinylnitroimidazoles RSU 1069 or RB6145 (prodrug for RSU 1069), dinitrophenylaziridine (CB1954), 2,3,5,6-tetramethylbenzoquinone (TMQ), diaziquone (AZQ), the intercalator amine N-oxide AQ4N, the bioreducible DNA alkylators NSC646394 and NSC658926, or any other agent that undergoes RED-catalyzed and/or P450-catalyzed bioreductive activation, including various nitroimidazoles, nitroaromatics, quinones, aliphatic, aromatic, or heterocyclic N-oxides, and bioreducible DNA alkylators (Boyer et al., *Oncol. Res.* 9:391–395 (1997); Patterson, A. V., et al., *Br. J. Cancer* 72:1144–1150 (1995); Workman, P., et al., *Cancer Metastasis Rev.* 12:73–82 (1993); Belinsky et al., *Cancer Metastasis Rev* 12:103–117 (June 1993); Patterson, L. H., et al., *Cancer Metastasis Rev.* 12:119–134 (1993); Rauth, A. M., et al., *Cancer Metastasis Rev.* 12:153–164 (1993); Bremner, J. C., et al., *Cancer Metastasis Rev.* 12:177–193 (1993); Goeptar, A. R., et al., *Crit. Rev. Toxicol.* 25:25–65 (1995)). Since several bioreductive drugs undergo enhanced cytochrome P450 and/or RED-catalyzed activation under conditions of tumor hypoxia, a preferred use of bioreductive drugs in the present invention involves the targeting of P450 and RED genes to hypoxic tumor regions using hypoxia response elements (Dachs, G. U., et al., *Nature Med.* 3:515–520 (1997); O'Rourke, J. F., et al., *Oncol. Res.* 9: 327–332 (1997)).

By "treating said neoplastic cells with a bioreductive drug" is intended to include local delivery of the drug into or near the site of the tumor, as well as the systemic administration of the bioreductive drug, i.e., through intraperitoneal, intravenous, parenteral, or intramuscular routes. Dosages of a particular bioreductive drug may be administered according to current standard clinical practice. See, e.g., Hubbard, S. M. and Jenkins, J. F., "Chemotherapy Administration: Practical Guidelines" in *Cancer Chemotherapy: Principles and Practice,* Chabner and Collins, eds., J. B. Lippincott Company, Philadelphia, Pa. (1990), pages 449–463; Graham, M. A., et al., *Cancer Chemother. Pharmacol.* 40:1–10 (1997)). Standard clinical practice may involve body surface area (BSA)-based dose calculations, as well as individualization of dosages based on pharmacokinetic optimization using plasma drug and metabolite concentrations ("therapeutic drug monitoring" or TDM). Such concentrations may be obtained using limited sampling or other pharmacokinetic sampling and modeling techniques (van Warnerdam, L. J., et al., *Neth J. Med.* 51:30–35 (1997); Desoize, B. and Robert, J., *Eur. J. Cancer* 30A:844–851 (1994); Gurney, H., *J. Clin. Oncol.* 14:2590–2611 (1996)). Other factors known to those skilled in the art, such as the clinical status and age of the patient, will also contribute to dosage adjustment.

The cytochrome P450 gene and the RED gene may be delivered to neoplastic cells using a viral vector, preferably one whose use for gene therapy is well known in the art. Techniques for the formation of vectors or virions are generally described in "Working Toward Human Gene Therapy," Chapter 28 in *Recombinant DNA, 2nd Ed.,* Watson, J. D. et al., eds., New York: Scientific American Books, pp. 567–581 (1992). An overview of suitable viral vectors or virions is provided in Wilson, J. M., *Clin. Exp. Immunol.* 107(Suppl. 1):31–32 (1997), as well as Nakanishi, M., *Crit. Rev. Therapeu. Drug Carrier Systems* 12:263–310 (1995); Robbins, P. D., et al., *Trends Biotechnol.* 16:35–40 (1998); Zhang, J., et al., *Cancer Metastasis Rev.* 15:385–401 (1996); and Kramm, C. M., et al., *Brain Pathology* 5:345–381 (1995). Such vectors may be derived from viruses that contain RNA (Vile, R. G., et al., *Br. Med Bull.* 51:12–30 (1995)) or DNA (Ali M., et al., *Gene Ther.* 1:367–384 (1994)).

Examples of viral vector systems utilized in the gene therapy art include the following: retroviruses (Vile, R. G., supra; U.S. Pat. Nos. 5,741,486 and 5,763,242); adenoviruses (Brody, S. L., et al., *Ann. N.Y. Acad. Sci.* 716: 90–101 (1994); Heise, C. et al., *Nat. Med.* 3:639–645 (1997)); adenoviral/retroviral chimeras (Bilbao, G., et al., *FASEB J.* 11:624–634 (1997); Feng, M., et al., *Nat. Biotechnol.* 15:866–870 (1997)); adeno-associated viruses (Flotte, T. R. and Carter, B. J., *Gene Ther.* 2:357–362 (1995); U.S. Pat. No. 5,756,283); herpes simplex virus I or II (Latchman, D. S., *Mol. Biotechnol.* 2:179–195 (1994); U.S. Pat. No. 5,763, 217; Chase, M., et al., *Nature Biotechnol.* 16:444–448 (1998)); parvovirus (Shaughnessy, E., et al., *Semin Oncol.* 23:159–171 (1996)); reticuloendotheliosis virus (Donburg, R., *Gene Therap.* 2:301–310 (1995)). Also of interest in the art, is the development of extrachromosomal replicating vectors for gene therapy (Calos, M. P., *Trends Genet.* 12:463–466 (1996)). Other viruses that can be used as vectors for gene delivery include poliovirus, papillomavirus, vaccinia virus, lentivirus, as well as hybrid or chimeric vectors incorporating favorable aspects of two or more viruses (Nakanishi, M., *Crit. Rev. Therapeu. Drug Carrier Systems* 12:263–310 (1995); Zhang, J., et al., *Cancer Metastasis Rev.* 15:385–401 (1996); Jacoby, D. R., et al., *Gene Therapy* 4:1281–1283 (1997)). Retroviruses and adenoviruses are the preferred viral vectors for gene delivery. Other suitable viral vectors will be readily apparent to the skilled artisan.

The vector will include one or more promoters or enhancers, the selection of which will be known to those skilled in the art. Suitable promoters include, but are not limited to, the retroviral long terminal repeat (LTR), the SV40 promoter, the human cytomegalovirus (CMV)

promoter, and other viral and eukaryotic cellular promoters known to the skilled artisan. Examples of enhancers include the tumor tissue-specific enhancers, described below.

Guidance in the construction of gene therapy vectors and the introduction thereof into affected animals for therapeutic purposes may be obtained in the above-referenced publications, as well as U.S. Pat. Nos. 5,631,236, 5,688,773, 5,691,177, 5,670,488, 5,529,774, 5,601,818, and WO 95/06486.

Generally, methods are known in the art for viral infection of the cells of interest. The virus can be injected into a patient bearing a neoplasm, either at, into, or near the site of neoplastic growth. Preferentially, the treatment will be by direct intraneoplastic inoculation. For tumors in the brain, magnetic resonance imaging (MRI), computerized tomography (CT), or other imaging guided stereotactic technique may be used to direct inoculation of the vector. The tumor may also be resected prior to treatment with the vectors of the invention.

The pharmaceutical compositions of the present invention would be advantageously administered in the form of injectable compositions. A typical composition for such purpose would comprise a pharmaceutically acceptable vehicle. Other pharmaceutically acceptable carriers include aqueous solutions, non-toxic excipients, including salts, preservatives, buffers and the like. See, *Remington's Pharmaceutical Sciences* (18th ed.), Mack Publishing Co. (1990). Examples of non-aqueous solvents are propylene glycol, polyethylene glycol, vegetable oil and injectable organic esters such as ethyloleate. Aqueous carriers include water, aqueous solutions, saline solutions, parenteral vehicles such as sodium chloride, Ringer's dextrose, etc. Intravenous vehicles include fluid and nutrient replenishers. The pH and exact concentration of the various components of the pharmaceutical composition are adjusted according to routine skills in the art (Goodman and Gilman, *The Pharmacological Basis for Therapeutics* (8th ed.) Pergamon Press (1990)).

Typically, the vector would be prepared as an injectable, either as liquid solutions or suspensions; solid forms suitable for solution in, or suspension in, liquid prior to injection may also be prepared. The preparation also may be emulsified. The active immunogenic ingredient is often mixed with an excipient which is pharmaceutically-acceptable and compatible with the active ingredient. Suitable excipients are, for example, water, saline, dextrose, glycerol, ethanol, or the like and combinations thereof. In addition, if desired, the preparation may contain minor amounts of auxiliary substances such as wetting or emulsifying agents, pH-buffering agents, adjuvants or immunopotentiators.

In general, the virus is provided in a therapeutically effective amount to infect and kill target cells. The quantity of the vector to be administered, both according to number of treatments and amount, will also depend on factors such as the clinical status, age, and weight of the subject to be treated, the capacity of the subject's immune system to synthesize antibodies, and available volume. Precise amounts of active ingredient required to be administered depend on the judgment of the gene therapist and will be particular to each individual patient. Generally, the viral vector is administered in titers ranging from about $1\times10^5$ to about $1\times10^9$ colony forming units (cfu) per ml, although ranges may vary. Preferred titers will range from about $1\times10^6$ to about $1\times10^8$ cfu/ml.

In one embodiment, a packaging cell line is transduced with a retroviral vector carrying the P450 and/or RED gene to form a producer cell line. The packaging cells may be transduced by any means known in the art, including, e.g., electroporation, $CaPO_4$ precipitation, or the use of liposomes. Examples of packaging cells that may be transfected include, but are not limited to, BOSC23, Bing, PE501, PA317, Ψ-2, Ψ-AM, PA12, T19-14X, VT-19-17-H2, Ψ-CRE, Ψ-CRIP, GP+E86, GP+envAm12, and DAN cell lines. Guidance on retroviral producing packaging cells and how to construct them can be found in Short et al., *J. Neurosci. Res.* 27:427–433 (1990); Miller, A. D., *Human Gene Ther.* 1:5–14 (1990); Danos, O, "Construction of Retroviral Packaging Cell Lines," in Methods in Molecular Biology (M. Collins, ed.), Vol. 8, The Humana Press Inc., Clifton, N.J., 17–26 (1991); Murdoch, B., et al., *Gene Therapy* 4:744–749 (1997); and U.S. Pat. Nos. 5,529,774, which issued on Jun. 25, 1996 and 5,591,624, which issued on Jan. 7, 1997.

Retroviral vectors have also been successfully packaged with a vesicular stomatitis virus (VSV) envelope glycoprotein G ("pseudotyping"). These vectors are more stable and can be concentrated to $10^9$ cfu/ml, allowing them to be injected directly (Burns, J. C., et al., *Proc. Natl. Acad. Sci. USA* 90:8033–8037 (1993)).

The producer cells can then be grafted near or into the tumor in an amount effective to inhibit or kill the neoplastic cells. Direct injection of high titer retroviral producer cells (Murdoch, B., et al., *Gene Ther.* 4:744–749 (1997); Onodera, M., et al., *Hum Gene Ther.* 8:1189–1194 (1997)) should allow for efficient in situ infection with the retroviral sequences (Rainov, N. G., et al., *Cancer Gene Ther.* 3:99–106 (1996); Ram, Z., et al., *Cancer Res.* 53:83–88 (1993)). Producer cells injected intratumorally do not generally migrate from the site of injection. Moreover, although they may be rejected by the host, this does not occur for 5–10 days, by which time retroviral infection of nearby tumor cells will have occurred (Ram, Z., et al., *J. Neurosurg.* 79:400–407 (1993)). In general, vector producer cell (VPC) dosages range from about $2.5\times10^8$ VPCs to about $1\times10^9$ VPCs. The exact amount of producer cells will ultimately be determined by the skilled artisan based on numerous factors, including, but not limited to, the available injectable volume, clinical status of the patient, and tumor type and size.

Preferably, the viral genomes of the viral vectors used in the invention should be modified to remove or limit their ability to replicate, however, replication conditional viruses will also be useful in the present invention, as will replicating vectors that are capable of targeting certain cells. See, e.g., Zhang, J., et al., *Cancer Metastasis Rev.* 15:385–401 (1996). Chase, M., et al. (*Nature Biotechnol.* 16:444–448 (1998)) used a herpes virus with an inactivated viral ribonucleotide reductase gene that selectively delivered P450 2B1 to tumor cells that overexpress the mammalian ribonucleotide reductase enzyme, which is required for this modified virus to replicate.

In one embodiment, a single viral vector is used to carry both the P450 and the RED genes. In another embodiment, two viral vectors are used; one carrying the P450 gene and the other carrying the RED gene. If two viral vectors are used, they can be derived from the same or a different type of virus, and can be administered simultaneously or sequentially (i.e., without regard for a specific order).

The P450 gene and the RED gene can also be delivered using non-viral methods for gene transfer, preferably those whose use in gene therapy is known in the art (Nakanishi, M., *Crit. Rev. Therapeu. Drug Carrier Systems* 12:263–310 (1995); Abdallah, B., et al., *Biol Cell* 85:1–7 (1995); Zhang, J., et al., *Cancer Metastasis Rev.* 15:385–401 (1996); Philips, S. C., *Biologicals* 23:13–16 (1995); Lee, R. J. and Huang, L., *Crit. Rev. Ther. Drug Carrier Syst.* 14:173–206 (1997)). Examples of such non-viral vectors for gene delivery include prokaryotic vectors, such as tumor targeted bacterial vectors (Pawelek, J. M., et al., *Cancer Res.* 57:4537–4544 (1997)), cationic liposomes, DNA-protein complexes, non-viral T7 autogene vectors (Chen, X., et al., *Hum. Gene Ther.* 9:729–736 (1998)), fusogenic liposomes, direct injection of nucleic acid ("naked DNA"), particle or receptor-mediated gene transfer, hybrid vectors such as DNA-adenovirus conjugates or other molecular conjugates involving a non-viral and viral component, starburstpolyamidoamine dendrimers (Kukowska-Latallo, J. F., et al., *Proc Natl Acad Sci USA* 93:4897–4902 (1996); Tang, M. X., et al., *Bioconjug. Chem.* 7:703–714 (1996)), cationic peptides (Wyman, T. B., et al., *Biochemistry* 36:3008–3017 (1997)), and mammalian artificial chromosomes (Ascenzioni, F., et al., *Cancer Lett.* 118:135–142 (1997)).

In addition, the present invention provides an embodiment of the foregoing methods wherein the P450 gene and the RED gene are delivered using any cellular vector, preferably one whose use for gene therapy is well-established for those skilled in the art. Examples of such cellular vectors for gene therapy include endothelial cells (Rancourt, C., et al., *Clin. Cancer Res.* 4:265–270 (1998); Qjeifo, J. O., et al., *Cytokines Mol. Ther.* 2:89–101 (1996)) and macrophages including tumor-infiltrating macrophages (Zufferey, R., et al., *Nat. Biotechnol.* 15:871–875 (1997); Naldini, L., et al., *Science* 272:263–267 (1996)), each of which may be modified using viral or non-viral vectors to carry the P450 gene and/or the RED gene, and thus express the P450 and RED gene products. Other suitable non-viral vectors will be readily apparent to the skilled artisan.

If a single vector is used, the P450 gene and the RED gene can be delivered as a fusion gene which encodes a P450-RED fusion protein. The construction of such a fusion gene is well-established for those skilled in the art (Fisher, C. W., et al., *Methods Enzymol.* 272:15–25 (1996); Shet, M. S., et al., *Proc. Natl. Acad. Sci. USA* 90:11748–11752 (1993); Fisher, C. W., et al., *Proc. Natl. Acad. Sci. USA* 89:10817–10821 (1992); Yabusaki, Y., *Biochimie* 77:594–603 (1995)), and may allow for highly efficient expression of P450 and RED activity.

Alternatively, gene delivery can be enhanced by including an internal ribosome entry site (IRES) sequence to achieve coordinate expression of the P450 gene and the RED gene on a bicistronic message. IRESs are sequences containing 500–600 bp that are typical of the 5' nontransduced regions of picornaviruses, including the polio- and encephalomyocarditis viruses (EMCV). See, e.g., Ghattas, I. R., et al., *Molecular and Cellular Biology* 11:5848–5859 (1991); Morgan, R. A., et al., *Nucleic Acids Research* 20:1293–1299 (1992). This approach has been used for efficient retroviral coexpression of the two subunits of interleukin-12 (Tahara, H., et al., *J. Immunol.* 154:6466–6474 (1995)). Another alternative is for the vector to contain both the P450 gene and the RED gene under the control of distinct promoters.

In another embodiment of the invention, the P450 and RED based drug activation system is combined with established gene/prodrug activation systems, including ganciclovir/HSV-TK and 5-fluorocytosine/CD (Moolten, F. L., *Cancer Gene Therapy* 1:279–287 (1994)). This can be accomplished either by separate transfer of both suicide genes (Aghi, M., et al., *J. Natl. Cancer Inst.* 90:370–380 (1998); Uckert, W., et al., *Human Gene Therapy* 9:855–865 (1998)), or by transfer of a fusion gene encoding both drug activation enzymes (Rogulski, K. R., et al., *Human Gene Therapy* 8:73–85 (1997)). P450/RED gene therapy may also be combined with other established cancer therapeutic genes, including tumor suppressor genes, such as p53 (Roth, J. A., et al., *Nature Med.* 2:985–991 (1996); Harris, M. P., et al., *Cancer Gene Therap.* 3:121–130 (1996)); apoptotic factors, such as bax (Bargou, R. C., et al., *J. Clin. Invest.* 97:2651–2659 (1996)), tumor necrosis factor alpha (Gillio, T. A., et al., *Blood* 87:2486–2495 (1996)), and caspases (Kondo, S., et al., *Cancer Research* 58:962–967 (1998); Yu, J. S., et al., *Cancer Research* 56:5423–5427 (1996)); and cytokines, such as interleukin 2 (Clary, B. M., et al., *Cancer Gene Ther.* 4:97–104 (1997); O'Malley, B. W., et al., *Ann. N.Y Acad. Sci.* 842:163–170 (1998)), interleukin 4 (Benedetti, S., et al., *Human Gene Therapy* 8:1345–1353 (1997)), and interleukin 12 (Chen, L., et al., *Immunol.* 159:351–359 (1997)).

In an additional embodiment, the targetting specificity for P450 and RED gene delivery may be facilitated by targeted delivery or targeted expression ("transcriptional targeting"), including the use of tumor-specific or tumor-selective DNA enhancer sequences to selectively activate expression of the transduced gene in the tumor cell at either the primary tumor site or its metastases (Miller, N. and Whelan, J., *Hum. Gene Ther.* 8:803–815 (1997); Walther, W. and Stein, U., *J. Mol. Med.* 74:379–392 (1996); Schnierle, B. S. and Groner, B., *Gene Therapy* 3:1069–1073 (1996); Lan, K -H., et al., *Cancer Res.* 57:4279–4284 (1997)); Dachs, G. U., et al., *Oncol. Res.* 9:313–325 (1997)). Examples of this approach include those DNA enhancers that have been derived from genes that encode tyrosinase (allowing for targeting to melanoma), ERBB2 (targeting to pancreatic cancer), carcinoembryonic antigen (targeting to lung and gastrointestinal malignancies, including colon, pancreatic and gastric cancer), DF3/MUC1 (targeting to breast cancer), and alpha-fetoprotein (targeting to hepatoma). The use of synthetic gene regulation systems, which allow for transcriptional control and other forms of regulated expression of the P450 and/or RED genes, may also be used (Miller, N. and Whelan, J., *Hum. Gene Ther.* 8:803–815 (1997); Vile, R. G., *Semin. Cancer Biol.* 5:429–436 (1994); Hwang, J. J., et al., *J. Virol.* 70:8138–8141 (1996); Massie, B., et al., *J. Virol.* 72:2289–2296 (1998)).

Another possibility is the use of DNA regulatory elements that are controlled by tumor-specific conditions and factors. For example, one unique aspect of solid tumors is their localized hypoxic environment (Brown, J. M. and Giaccia, A. J., *Cancer Res.* 58:1408–1416 (1998)). This characteristic can be exploited to induce the expression of genes that are controlled by hypoxia (hypoxia response elements or "HRE") (Dachs, G. U., et al., *Nature Med.* 3:515–520 (1997); O'Rourke, J. F., et al., *Oncol. Res.* 9: 327–332 (1997)). Thus, in an additional embodiment, HRE sequences can be used for the transcriptional targeting of cytochrome P450 and/or RED genes to hypoxic neoplastic cells.

Inhibition of liver P450-catalyzed drug activation may provide an approach to increasing the fraction of a given chemotherapeutic drug that is activated within the tumor. Thus, in another embodiment of the invention, delivery of the P450 and RED genes to the tumor is combined with systemic administration of inhibitors of liver P450 activity in order to increase the specificity of intratumoral drug activation. Such inhibitors of liver P450 activity include various chemicals and other small molecule P450 inhibitors directed at the specific P450 enzymes that catalyze drug activation in the liver, including sulfaphenazole, a P450 2C9-selective inhibitor (Bourrie, M., et al., *J. Pharmacol*

*Exp Ther.* 277:321–332 (1996); Newton, D. J., et al., *Drug Metab Dispos.* 23:154–158 (1995)) that inhibits P450 2C9-catalyzed human liver CPA activation (Ren, S., et al., *Cancer Res.* 57:4229–4235 (1997)) and the P450 3A4-specific inhibitors ketoconazole and troleandomycin (TAO), directed at P450 3A4-catalyzed human liver IFA activation (Chang, T. K. H., et al., *Cancer Res.* 53:5629–5637 (1993); Walker, D., et al., *Biochem Pharmacol.* 47:1157–1163 (1994)). Other useful inhibitors include general inhibitors of liver P450 metabolism, such as cimetidine, chloramphenicol, and aminobenzotriazole (Halpert, J. R., et al., *Toxicol Appl Pharmacol.* 125:163–175 (1994); Meschter, C. L., et al., *Fundam Appl Toxicol.* 22:369–381 (1994)). Many of these P450 inhibitors are clinically useful drugs that can safely be administered to humans, and in several cases have been shown to inhibit CPA activation in cancer patients (Faber, O. K., et al., *Br J. Clin Pharmacol.* 2:281–285 (1975); Graham, M. A., et al., *Pharmacol Ther.* 51:275–289 (1991)). Alternatively, antithyroid drugs such as methimazole and propylthiouracil may be used to selectively decrease the expression of hepatic P450 reductase, and thereby inhibit liver P450 activity (Ram, P. A. and Waxman, D. J., *J. Biol Chem.* 267:3294–3301 (1992); Waxman, D. J., et al., *Mol Pharmacol.* 35:519–525 (1989)). This is supported by the finding that methimazole-induced hypothyroidism has no effect on RED activity in 9L gliosarcoma grown subcutaneously as solid tumors in rats [19±4 (control rats) vs. 23±5 nmol/minute/mg 9L microsomal protein (methimazole-treated rats) (n=6 tumors/group)] under conditions where liver RED activity is decreased to approximately 25% of control [300±80 (control livers) vs. 76±19 nmol/minute/mg (methimazole livers) (n=3 livers/group)].

In another embodiment, rather than delivering the P450 or RED genes, the P450 gene product and/or the RED gene product may be delivered using streptavidin-biotin-based or other protein delivery methods which are well-established for those skilled in the art (Ohno, K. and Meruelo, D., *DNA Cell. Biol.* 15:401–406 (1996); Ohno, K., et al., *Biochem. Mol. Med* 58:227–233 (1996)).

Up-regulation of endogenous RED activity and/or endogenous P450 activity in cancer cells by hormones or drug inducers provides an additional approach to rendering tumor cells hypersensitive to the anticancer drug-activating P450 genes. Thus, the invention provides methods for killing neoplastic cells wherein endogenous levels of either cytochrome P450 or RED are increased in the neoplastic cells, and gene transfer is carried out with the gene whose product is not endogenously increased.

In one such embodiment, the invention provides a method for killing neoplastic cells, the method comprising: (a) administering an agent that will increase the activity or expression level of endogenous RED in the neoplastic cells; (b) infecting the neoplastic cells with a vector, the vector comprising a cytochrome P450 gene; (c) treating the neoplastic cells with a chemotherapeutic agent that is activated by the gene product of the cytochrome P450 gene; and (d) killing the neoplastic cells. In a preferred embodiment of this method, the cytochrome P450 gene is a mammalian gene, such as P450 1A1, 1A2, 1B1, 2B1, 2B2, 2B4, 2B5, 2B6, 2B1 1, 2A6, 2C6, 2C8, 2C9, 2C1 1, 2C18, 2C19, 2D6, 2E1, 3A4, 3A5, 3A7, or 4B1, or members of corresponding P450 gene families and subfamilies in other species whose cDNA sequences are known (Nelson, D. R., et al., *Pharmacogenetics* 6:1–42 (1996)), or any other P450 gene, including their allelic variants, site-specific mutants, and chimeric constructs (e.g., Chang, T. K. H., et al., *Pharmacogenetics* 7:211–221 (1997); Szklarz, G. D., et al., *Biochemistry* 34:14312–14322 (1995); He, Y. A., et al., *Biochemistry* 36:8831–8839 (1997)). The rat cytochrome P450 gene 2B1 and the human cytochrome P450 genes 2B6, 2C18, and 3A4 are particularly preferred.

In another such embodiment, the invention provides a method for killing neoplastic cells, the method comprising: (a) administering an agent that will increase the activity or expression level of endogenous cytochrome P450 in the neoplastic cells; (b) infecting the neoplastic cells with a vector, the vector comprising a RED gene; (c) treating the neoplastic cells with a chemotherapeutic agent that is activated by the product of the cytochrome P450 gene; and (d) killing the neoplastic cells.

The invention also provides preferred embodiments of the foregoing methods, wherein the agent that will increase the activity or expression level of endogenous RED in the neoplastic cells is thyroid hormone or phenobarbital, and the agent that will increase the activity or expression level of endogenous P450 in the neoplastic cells is dexamethasone, rifampin, 1,4-bis-2-(3,5-dichloropyridyloxybenzene) (TCPOBOP), or phenobarbital. TCPOBOP has been identified as a profound inducer of human cytochrome P450s in colon and breast tumors (Smith, G., et al., *Br. J. Cancer* 68:57–63 (1993)).

In addition, the invention also provides a preferred embodiment of the foregoing methods, wherein the chemotherapeutic agent is cyclophosphamide, ifosfamide, dacarbazine, procarbazine, thio-TEPA, etoposide (VP-16), 4-ipomeanol, 2-aminoanthracene, or tamoxifen.

The present invention also provides an additional embodiment of the foregoing methods, wherein the neoplastic cells are also treated with a bioreductive drug (i.e., the bioreductive drug is administered in addition to treatment with the P450-activated chemotherapeutic agent described above). Alternatively, the bioreductive drug may be used on its own (i.e., in place of the P450-activated chemotherapeutic agent). In a preferred embodiment, the bioreductive drug is a nitroimidazole, a nitroaromatic, a quinone, an aliphatic, aromatic, or heterocyclic N-oxide, or a bioreducible DNA alkylator that is capable of undergoing RED-catalyzed or P450-catalyzed bioreductive activation. In a particularly preferred embodiment, the bioreductive drug is Adriamycin, porfiromycin, mitomycin C, tirapazamine (TPZ or SR 4233), indoloquinone E09, aziridinylnitroimidazoles RSU1069 or RB6145, dinitrophenylaziridine (CB1954), diaziquone (AZQ), the intercalator amine N-oxide AQ4N, and the bioreducible DNA alkylators NSC646394 and NSC658926. Since several bioreductive drugs undergo enhanced cytochrome P450 and/or RED-catalyzed activation under conditions of tumor hypoxia, a preferred use of bioreductive drugs in the present invention involves the targeting of P450 and RED genes to hypoxic tumor regions using hypoxia response elements (Dachs, G. U., et al., *Nature Med.* 3:515–520 (1997); O'Rourke, J. F., et al., *Oncol. Res.* 9: 327–332 (1997)).

Exemplary candidates for treatment according to the present invention include, but are not limited to humans, other mammals, or non-mammal animals suffering from neoplasms, and in particular, solid malignant tumors.

The invention also provides another embodiment of the invention, whereby the levels of endogenous RED and/or cytochrome P450 are assayed in biopsies prepared from a given tumor, in order to predict responsiveness to P450-activated chemotherapeutic drugs, such as, e.g., CPA and IFA, or to bioreductive drugs that may be activated by RED and/or P450, such as, e.g., Adriamycin, mitomycin C, or tirapazamine (TPZ).

By "assaying the expression level of endogenous cytochrome P450" is intended qualitatively or quantitatively measuring or estimating the level of individual cytochromes P450 or the level of the mRNAs encoding individual cytochromes P450 in a tumor sample, using analytical methods well-established for those skilled in the art, including immunohistochemistry and Western blot analysis with P450 form-selective antibodies, enzymatic analysis using P450 form-selective substrates, and in situ hybridization using P450 gene-specific DNA or RNA probes (Waxman, D. J., *Methods in Enzymology* 206:249–267 (1991)). For example, endogenous cytochrome P450 levels in the range of 1 to 20 pmol/mg microsomal protein, as determined by Western blot analysis, would be indicative of responsiveness to drugs such as CPA or ifosfamide (see, e.g., Table 2 of Example 2, below).

Tumors in certain tissues in mammals express significantly varied levels of RED. Thus, in another embodiment, levels of endogenous RED are assayed in a given human tumor as a prognostic indicator of P450-based gene therapy (in the absence of cotransfected RED), and to aid the practitioner in determining if RED would be particularly useful to incorporate into a P450-based gene therapy strategy. That is, tumor cells with moderate levels (20–60 nmol cytochrome C reduced/minute/mg microsomal protein, assayed under standard conditions (see Example 1)), or low levels (<20 nmol/minute/mg) of RED activity would be prime candidates for incorporating the RED gene into any P450-based gene therapy paradigm. Tumor cells with a high endogenous level of RED activity (>60 nmol/minute/mg) may be predictive of effective P450-based cancer gene therapy, without co-transfer of RED.

By "assaying the expression level of endogenous RED" is intended qualitatively or quantitatively measuring or estimating the level of RED or the level of the mRNA encoding RED in a tumor sample. RED levels in a tumor sample may be assayed by cytochrome C reduction (Phillips, A. H., et al., *J. Biol Chem.* 23 7:2652–2660 (1962)) or by Western blotting or immunohistochemistry (Grant, R., and Ironside, J. W., *J. Neurooncol.* 25:1–7 (1995); Foster, J. R., et al., *J Pathol.* 169:457–463 (1993)). RED mRNA may be assayed by in situ hybridization or by using the RNase protection assay described in Shephard, E. A., et al., *Archives of Biochemistry and Biophysics* 294: 168–172 (1992).

A further embodiment of the present invention relates to using P450/RED-based prodrug activation gene therapy for treatment of diseases other than neoplastic disease in cases where localized generation of activated metabolites is desirable, or in cases where prodrug activation is efficiently catalyzed by a P450 gene that is not normally expressed at high levels in the patient.

As a result of the enhanced production of cytotoxic drug metabolites that occurs when a RED gene is transferred to tumor cells in combination with a drug-activating P450 gene, the method of the invention allows for greater localized tumor toxicity at a given drug concentration, leading to an enhanced chemotherapeutic response. It may also allow for lower doses of the drug to be given, thereby reducing toxic effects to the patient by decreasing exposure of normal cells to cytotoxic metabolites.

Having generally described the invention, the same will be more readily understood by reference to the following examples, which are provided by way of illustration and are not intended to limit the invention.

EXAMPLE 1

P450 Reductase (RED) Enhancement of Cytochrome P450 Gene Therapy

This Example demonstrates the utility of combining RED gene transfer with P450-based drug activation cancer gene therapy. Rat 9L gliosarcoma cells stably expressing either basal or elevated (up to 10-fold increased) levels of rat RED, in the presence or absence of P450 2B1, were shown to have substantially increased sensitivity to the cytotoxic effects of the anticancer drug cyclophosphamide (CPA). An enhanced cytotoxic response was also obtained when recombinant adenovirus encoding P450 2B1 was used to deliver the P450 gene to RED-overexpressing tumor cells. CPA cytotoxicity was substantially decreased by the RED inhibitor diphenyleneiodonium chloride or by the P450 inhibitor metyrapone, evidencing its dependence on the catalytic contributions of both protein components of the P450 metabolic pathway. Conditioned media from P450 2B1-expressing and RED-overexpressing tumor cells treated with CPA exhibited increased formation of the primary 4-hydroxy metabolite and greater cell contact-independent bystander cytotoxic potential compared to tumor cells containing P450 2B1 and basal levels of RED. Evaluation of the impact of P450+RED combination gene therapy using a subcutaneous solid tumor model/tumor excision assay revealed a dramatic 50–100-fold increase in tumor cell kill in Yivo over that provided by liver drug activation alone. These findings establish the importance of endogenous RED levels as a determinant of the sensitivity of tumor cells to P450-based gene therapy and demonstrate the striking therapeutic effectiveness of an anti-cancer prodrug activation strategy based on the combination of a P450 gene with the gene encoding RED.

Materials and Methods

Chemicals: CPA, ifosfamide and 3-aminopyridine adenine dinucleotide (AADP) were obtained from Sigma Chemical Co. (St. Louis, Mo.). 4-hydroperoxy-CPA was obtained from Nova Pharmaceutical Corporation (Baltimore, Md.). Metyrapone and diphenyleneiodonium chloride (DPI) were purchased from Aldrich Chemical Co. (Milwaukee, Wis.).

Cell lines: Rat 9L gliosarcoma parental cells (Barker, M., et al., *Cancer Res.* 33:976–986 (1973)), 9L transfectants P3 and P17, which stably express the P450 gene CYP2B1, and the 9L transfectant 9L-lacZ, which stably expresses the *E. coli* β-galactosidase gene (Chen, L. and Waxman, D. J., *Cancer Research* 55:581–589 (1995)), were grown in DMEM containing 10% fetal bovine serum (FBS), 2 mM L-glutamine, 50 units/ml penicillin, 50 μg/ml streptomycin and 3.79 g/L $NaHCO_3$, with the pH adjusted to 7.2. Cells were maintained in a humidified atmosphere of 5% $CO_2$/95% air. The parental 9L and CYP2B1-expressing cells were co-transfected with a rat RED expression plasmid (p450-Red-CMV, kindly provided by Dr. Gregorio Gil, University of Massachusetts) (Chang, T. K., et al., *Biochem. J.* 291 (pt2):429–433 (1993)) and plasmid pREP[4] (Invitrogen, CA) in a molar ratio of 10:1 using Lipofectin (GIBCO/BRL, Inc.) according to the manufacturer's instructions. The plasmid pREP4 contains a hygromycin resistance gene. Cell clones resistant to hygromycin B (300 μg/ml) were cloned, propagated, and evaluated.

In vitro cytotoxicity assay: (A) Colony formation assay—Cells ranging from 200 to 20,000 per well were plated in duplicate in 30 mm tissue culture plates and treated with CPA at the indicated drug concentrations. Seven days later, plates were stained with crystal violet and the number of colonies with >50 cells was counted. The survival fraction was expressed as the number of colonies in each treated group compared to the untreated control. (B) Growth inhibition assay—Cells (1000/well) seeded in 96 well plates were treated with the indicated concentrations of CPA for 4–5 days. Corresponding controls received no drug treatment. Cell survival was determined by an XTT colorimetric assay, a cell proliferation assay that measures mitochondrial dehydrogenase activity of viable cells (Scudiero, D. A., et al., Cancer Res. 48:4827–4833 (1988)).

Assay of activated CPA and ifosfamide metabolites in culture medium from chemotherapeutic drug-treated tumor cells: Cells were plated at $1.5 \times 10^6$ cells/30 mm dish and then incubated for 24 hours with 2 mM CPA or 2 mM ifosfamide in the presence of 5 mM semicarbazide (stock solution prepared in culture media, pH 7.4), which traps and stabilizes the initial 4-hydroxy metabolite. In control experiments, semicarbazide at this concentration had no detectable effect on cell viability when incubated with the cells for up to 48 hours. The drug-conditioned media from each cell line was harvested at 24 hours and 0.3 ml of media was used to assay 4-hydroxy-CPA or 4-hydroxy-ifosfamide by a fluorometric assay (Chang, T. K. H., et al., Cancer Res. 53:5629–5637 (1993)).

Limited dilution assay to evaluate bystander killing effect: 9L cells were seeded in 6-well plates at $1.5 \times 10^6$ cells/well for 12 hours, and treated with 2 mM CPA for 48 hours. The conditioned media from each well was collected, diluted 5–50% into fresh media as indicated for each experiment, and added into wells of a second set of 6-well plates pre-seeded with parental 9L cells ($10^4$ cells/well). Cultures were maintained for 5–7 days and colonies were scored as described for the clonogenic assay.

In vivo cytotoxicity assay: Tumor cells were grown subcutaneously as solid tumors in female Fischer 344 rats (120–150g). Each rat was inoculated by subcutaneous injection of one tumor cell line at the right thigh and a second tumor cell line at the left thigh at $2 \times 10^6$ cells/site. Rats were randomized and divided into three groups. One group was injected with saline as a control. The other two groups were treated with CPA at 50 mg/kg or 100 mg/kg body weight given as a single intraperitoneal injection 2 weeks after tumor implantation. At 24 hours after CPA injection, the rats were sacrificed and soaked briefly in 75% ethanol. The tumors were excised, suspended in DMEM, and minced under sterile conditions. The tumor tissue was then incubated for 15 minutes at 37° C. with shaking in a solution of 500 units/ml of collagenase (Sigma) containing 0.2 mg/ml of DNase (Sigma). The samples were filtered through a Cell Strainer (Fisher Scientific), washed twice with DMEM, and then suspended in DMEM supplemented with 10% fetal calf serum. The single cell suspensions were counted and plated at densities of 200, $2 \times 10^3$ and $2 \times 10^4$ cells/well of a 6-well plate, in duplicate, to determine cell viability by a colony formation assay. Cell cultures were changed to fresh medium after overnight incubation. Cells were grown for 7 days and colonies (>50 cells) were then stained with crystal violet and counted. Results are expressed as the surviving fractions SEM of cells from drug treated groups compared to untreated controls. The untreated tumor cell suspension had a plating efficiency (colony forming activity) ranging from 3.0 to 12.2% in individual experiments.

Adenovirus-mediated CYP2B1 gene transduction: A recombinant adenovirus, Ad.CMV-2B1, carrying the CYP2B1 gene was constructed as described in Chen, L., et al., Cancer Res. 56:1331–1340 (1996). Large scale production of recombinant adenovirus was performed by growth in 293 cells followed by purification by double cesium gradient ultracentrifugation (Graham, F. L. and Prevec, L., "Manipulation of Adenovirus Vectors" in Methods in Molecular Biology:Gene Transfer and Expression Protocols, volume 7, E. J. Murray (ed.), The Human Press, Inc., Clifton, N.J., pages 109–127 (1991)). The titer of purified adenovirus was determined in a spectrophotometer at 260 nm and by plaque assays. Ad.CMV-2B1 was added to the cells plated on 30 mm diameter tissue culture plates at multiplicities of infection (MOI) as indicated in the figure legends. Twenty four hours after viral infection, the infected cells were trypsinized and replated at 500 cells/well onto 96 well tissue culture plates and treated with CPA. Four to seven days after CPA treatment, the number of surviving cells was determined using the XTT assay described above.

Western blot and RED enzymatic analysis: Microsomal proteins or cell lysates prepared from cultured cells by differential centrifugation were electrophoresed through 10% sodium dodecyl sulfate/polyacrylamide gels (20 µg protein/lane), transferred to nitrocellulose and then probed (Waxman, D. J., Methods Enzymol. 206:249–267 (1991)), with polyclonal rabbit anti-CYP2B1 antibodies or with rabbit anti-rat P450 reductase antibodies (Waxman, D. J. and Walsh, C., J. Biol. Chem. 257:10446–10457 (1982); Ram, P. A. and Waxman, D. J., J. Biol. Chem. 267:3294–3301 (1992)). Phenobarbital-induced rat liver microsomes (1 µg) were used as a positive control for CYP2B1. RED activity was assayed in cell homogenates by the NADPH-dependent reduction of cytochrome C at 550 nm (E=21 $mM^{-1}$ $cm^{-1}$) in 0.3M KPi buffer, pH 7.7 at 30° C. (Waxman, D. J. and Walsh, C., J. Biol. Chem. 257:10446–10457 (1982)).

Results

Figure 1A:
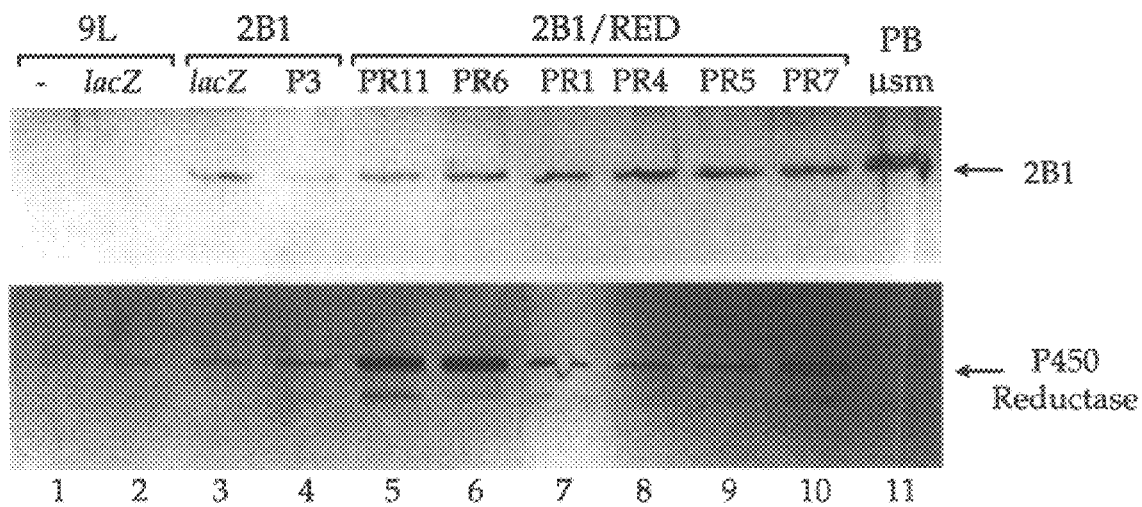
FIG. 1A is a photograph of an immunoblot depicting CYP2B1 protein levels (top panel) and P450 reductase (RED) protein levels (bottom panel) in individual 9L tumor cell lines transduced with the P450 2B1, RED and/or a lacZ marker gene according to the present invention. Microsomal proteins prepared from individual clonal cell lines (20 μg protein/lane) were analyzed on a Western blot probed with polyclonal rabbit anti-CYP2B1 antibodies (top) or anti-RED antibodies (bottom). Individual stable cell lines were prepared by stable transfection of CYP2B1 and/or RED, as indicated. Phenobarbital-induced rat liver microsomes (1 μg containing approximately 0.9 pmol CYP2B1) were used as a positive control for CYP2B1 (lower band of doublet in lane 11, top panel). Sample in lane 2 is a 9L cell line stably transfected to express the lacZ gene, while a 9L/2B1/lacZ line is shown in lane 3 (Chen, L. and Waxman, D. J., *Cancer Research* 55:581–589 (1995)). Line PR6, derived from P3, expressed RED at a level similar to PR11 (lane 6). Lines PR1, PR4 and PR5, all derived from P17, expressed RED protein (lanes 7–9) and enzyme activity (data not shown) at a 1.5 to 2-fold higher level than 9L wild-type cells and were not characterized further. RED protein was not detectable in lane 11 owing to the low loading of liver microsomal protein. CYP2B1 specific contents of 7–10 pmol P450 2B1/mg microsomes (P3 and PR11) and 15–20 pmol P450 2B1/mg (P17 and PR7) were determined by comparison to the CYP2B1 standard.
Figure 1B:
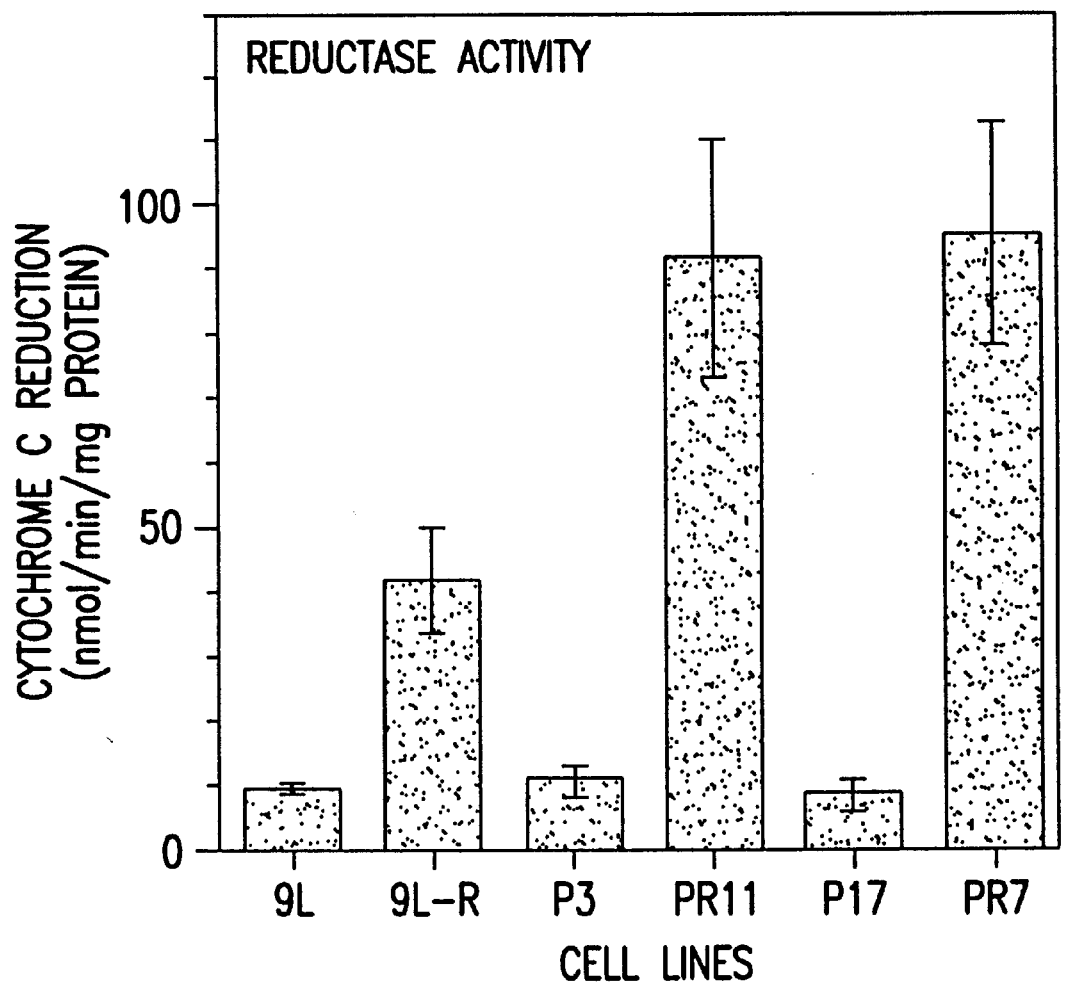
FIG. 1B is a bar graph depicting RED enzyme activity (rate of cytochrome C reduction) in cell homogenates prepared from 9L tumor cell lines. Cell lines overexpressing RED were designated with an "R" (9L-R, PR-11, PR-7), those expressing CYP2B1 were designated by a "P" (P3, P17), and those expressing both RED and CYP2B1 were designated by "PR" (PR11, PR7). Lines 9L-R, P3, and P17 were derived from parental 9L cells, line PR11 was derived from P3, and line PR7 was derived from P17.

Establishment of tumor cell lines overexpressing RED: Parental rat 9L gliosacoma cells and CYP2B1-expressing 9L cells were co-transfected with an expression plasmid encoding rat RED and a plasmid containing a hygromycin resistance gene. Cell lines resistant to hygromycin B were selected and cloned. Western blot analysis of cell lysates using a rabbit polyclonal antibody specific to RED showed the overexpression of a single protein band of approximately 80 kD, corresponding to the molecular mass of purified RED, in samples prepared from the clonal cell lines (FIG. 1A). Cell line 9L-R (FIG. 1B) was derived from CYP2B1$^-$ parental 9L cells. Line PR11 was derived from the CYP2B1$^+$ cell line P3, and line PR7 was derived from CYP2B1$^+$ cell line P 17 and exhibited CYP2B1 protein contents of 7–10 pmol CYP2B1/mg microsomal protein (P3 and PR11) and 15–20 pmol CYP2B1/mg (P17 and PR7) (FIG. 1A and data not shown). Analysis of RED enzyme activities indicated that the RED activities are 4–10 fold higher in the RED-transfectants than in the corresponding parental cell line controls (FIG. 1B). Overexpression of RED did not significantly alter the growth rate of these cells (data not shown). The clonal cell lines 9L, 9L-R, P3, PR11, P17, and PR7 were used for further studies.

Effect of RED overexpression on CPA sensitivity of CYP2B1-positive and CYP2B1-negative tumor cells: The inventors tested whether the overpression of RED sensitizes tumor cells to CPA. Multiple RED-overexpressing cell lines derived from CYP2B1$^-$ and CYP2B1$^+$ cell lines were assayed for their sensitivity to CPA cytotoxicity. As shown in FIG. 2, although the overexpression of RED alone did not sensitize 9L tumor cells to CPA (line 9L-R), overexpression of RED in CYP2B1$^+$ cells significantly enhanced the cytotoxic response (lines PR11, PR7 compared to lines P3, P17). This enhanced cytotoxicity was evident both in a colony formation assay (FIG. 2A) and in a growth inhibition assay (FIG. 2B). Overexpression of RED in CYP2B1$^+$ cells (9L/2B1/RED) also enhanced the chemosensitivity of the cells to ifosfamide, an isomer of CPA that also undergoes P450-catalyzed drug activation (FIG. 2C). Each of the cell lines showed a similar intrinsic sensitivity to activated CPA when chemically activated drug was presented to the cells in the form of 4-hydroperoxy-CPA.

Effects of P450 and RED enzyme inhibition on CPA sensitivity in RED-overexpressing tumor cells: In previous studies, a CYP2B1-selective enzyme inhibitor, metyrapone was used to verify that the overexpression of CYP2B1 per se is responsible for the chemosensitivity of CYP2B1-positive tumor cells to CPA and ifosfamide (Chen, L. and Waxman, D. J., *Cancer Research* 55:581–589 (1995)). In further support of those findings, metyrapone at 10 $\mu$M and higher concentrations significantly blocked the cytotoxic effects of CPA toward CYP2B1$^+$ cells (FIG. 3; P3 and P17 cell lines). By contrast, in RED-overexpressing CYP2B1$^+$ cells, metyrapone at a concentration of 10 $\mu$M only slightly inhibited the cytotoxic effect of CPA. Significant blocking of CPA cytotoxicity required a much higher concentration of metyrapone, both in colony formation assays (FIG. 3A) and in growth inhibition assays (FIG. 3B). In order to verify that the overexpression of RED is, in fact, the cause of the enhanced chemosensitization of the CYP2B1$^+$RED$^{+++}$ cells, we examined the effects of two RED inhibitors: AADP, a competitive inhibitor of RED (Lemaire, P. and Livingstone, D. R., *J. Biochem. Toxicology* 9:87–95 (1994)), and DPI, a mechanism-based inhibitor of RED activity (Tew, D. G., *Biochemistry* 32:10209–10215 (1993); McGuire, J. J., et al., *J. Pharmacol. Exper. Therap.* 271:708–714 (1994)). In control experiments carried out in the absence of CPA, AADP at 0.5 mM showed no toxicity to the cells, while DPI at 5 $\mu$M showed about 20% growth inhibition. AADP and DPI partially rescued the CYP2B1$^+$ and CYP2B1$^+$RED$^{+++}$ cells from CPA toxicity, with the extent of this protection effect more prominent in the case of the CYP2B1$^+$RED$^{+++}$ cells (FIG. 4). Overall, the cell survival ratio was increased by 2–3-fold (AADP) and by 3–5-fold (DPI) in CYP2B1$^+$RED$^{+++}$ cells. Thus, the enhanced chemosensitivity of CYP2B1$^+$RED$^{+++}$ cells to CPA is dependent on the overexpression of RED enzyme activity.

Bystander killing potential of RED-expressing tumor cells: CPA-treated CYP2B1$^+$ cells mediate a bystander killing of co-cultured CYP2B1 cells that does not require direct cell-cell contact (Chen, L. and Waxman, D. J., *Cancer Res.* 55:581–589 (1995)). Based on this observation, a limited dilution assay was carried out to evaluate the cytotoxic potency of conditioned media obtained from each of the 9L tumor cell lines incubated with CPA. Conditioned media from the CYP2B1$^+$R$^{+++}$ cell lines PR11 and PR7 was substantially more cytotoxic than conditioned media prepared from the CYP2B1$^+$ cells P3 and P17 (FIG. 5). This increased formation of cytotoxic metabolites by the RED-overexpressing cells resulted in a greater bystander cytotoxicity of these cells toward co-cultured 9L cells that do not express CYP2B1. As shown in FIG. 6, CPA treatment resulted in a substantial, albeit incomplete, bystander cytotoxicity of CYP2B1$^+$9L cells toward CYP2B1$^-$9L cells, which were marked in this experiment with the lacZ gene and visualized by X-gal staining (FIG. 6B vs. FIG. 6A). However, co-culture with CYP2B1$^+$RED$^{+++}$ cells resulted in a near complete killing of the 9L/lacZ cells (FIG. 6D vs. FIG. 6C). CPA treatment essentially eliminated both the CYP2B1$^+$ cells and the CYP2B1$^+$RED$^{+++}$ cells in the experiment shown (unstained cells, FIGS. 6B and 6D).

Enhancement of P450 metabolic activity is dependent on the level of overexpression of RED: To determine whether there is a direct relationship between the extent of RED overexpression and the P450 metabolic activity of neoplastic cells, a series of independent, clonal 9L/2B1/RED stable co-transfectants were selected and then characterized. RED enzyme activity and P450 2B1 metabolic activity were measured in isolated microsomal fractions. Table 1 shows that in a series of 6 independent 9L/2B1/RED transfectants, designated R1–R11, RED enzyme activity ranged from 1.2 to 5.4-fold higher than the RED activity measured in parental 9L/2B1 cells. The P450 metabolic activity measured in these cell lines was increased in rank order and a manner that is roughly proportional to the RED level of each cell line (Table 1, last column). Thus, the enhanced sensitivity of 9L/2B1 cell lines to drug cytotoxicity following RED gene transfer is associated with increased P450 metabolic activity which is directly dependent on the extent of increase in RED expression. Moreover, this effect was obtained, despite the fact that the parental 9L and 9L/2B1 cells already exhibited a level of RED expression (18±3 pmol RED/mg) (Table 1) that was greater than or equimolar with the cells' CYP2B1 protein content (7–10 pmol 2B1/mg for P3 and PR11 cells; 15–20 pmol 2B1/mg for P17 and PR7 cells, FIG. 1).

TABLE 1

P450 reductase overexpressing 9L cell lines
(cell lines designated PR1–PR11)

| 9L Cell Line | P450 Reductase activity$^a$ | fold-increase | P450 activity$^b$ | Relative P450 activity$^c$ |
|---|---|---|---|---|
| 9L | 57 ± 10$^e$ | =1.0 | <5 | |
| 9L/2B1 | 59 ± 9 | 1.0 | 29 | =1.0 |
| 9L/2B1/PR5$^d$ | 70 ± 6 | 1.2 | 42 | 1.4 |
| 9L/2B1/PR4 | 83 ± 5 | 1.5 | 37 | 1.3 |
| 9L/2B1/PR1 | 130 ± 5 | 2.3 | 49 | 1.7 |
| 9L/2B1/PR6 | 248 ± 12 | 4.4 | 81 | 2.8 |
| 9L/2B1/PR11 | 295 ± 10 | 5.2 | 73 | 2.5 |
| 9L/2B1/PR7 | 309 ± 10 | 5.4 | 92 | 3.2 |

$^a$nmol cytochrome c reduced/minute/mg microsomal protein assayed at 30° C.
$^b$pmol per minute/mg microsomal protein; P450 activity measured using 7-ethoxycoumarin as substrate.
$^c$fold increase in P450 activity parallels the P450 reductase content of each cell line.
$^d$"R" designates cell lines that over-express P450 reductase.
$^e$Activity corresponds to 18 ± 3 pmol P450 reductase protein/mg microsomes, based on a measured P450 reductase specific activity of 40 $\mu$mol cytochrome C reduced/minute/mg purified reductase [M$_r$ = 78,000] under the same assay conditions.

Metabolism of CPA to 4-hydroxy-CPA by RED overexpressing tumor cells: To ascertain whether the increased CPA sensitivity of CYP2B1$^+$RED$^{+++}$ cells was associated with an increase in the conversion of CPA to its activated metabolites, culture medium was collected from the tumor cell lines 24 hours after incubation with CPA in the presence of 5 mM semicarbazide, which stabilizes the primary metabolite 4-hydroxy-CPA. Analysis of the fluorescent product obtained after derivatization with 3-aminophenol revealed up to 3-fold higher levels of 4-hydroxy-CPA formed by the CYP2B1$^+$RED$^{+++}$ cell lines compared to the corresponding parental CYP2B1$^+$ controls (FIG. 7). The low level of apparent 4-hydroxylated metabolites seen in the case of 9L parental cells corresponds to the limit of detection in the fluorescent assay.

Adenovirus-mediated transfer of CYP2B1 gene to tumor cells with and without RED overexpression: The studies described above were performed in isolated clonal cell lines. To further establish the relationship of RED overexpression to the enhanced chemosensitivity of CYP2B1$^+$ tumor cells, replication-defective recombinant adenovirus carrying the CYP2B1 gene (Ad.CMV-2B1) was used to infect parental 9L and 9L-R at multiplicities of infection ranging from 50 to 800. As shown in FIG. 8, cells infected with Ad.CMV-2B1 acquired CPA sensitivity, with the effect most striking in the case of the RED overexpressing tumor cells (FIG. 8B). In control experiments, infection of 9L cells with an adenovirus carrying the lacZ gene (encoding bacterial P-galactosidase) did not sensitize the cells to CPA.

Chemosensitivity of RED-overexpressing 9L/2B1 tumors treated with CPA in vivo: In order to determine whether RED overexpression in CYP2B1+tumor cells translates into a therapeutic advantage in vivo, a tumor excision assay was employed to quantitate drug toxicity induced in vivo over a 24 hour period following CPA treatment. $CYP2B1^+$ and $CYP2B1^+RED^{+++}$ 9L tumors and parental $CYP2B1^-9L$ tumors were grown subcutaneously in female Fischer 344 rats and then were treated with CPA. Twenty four hours after CPA treatment, the tumors were excised from the animals, dispersed to give a single cell suspension and then plated on culture dishes. The number of surviving tumor cells that form colonies was then determined. As shown in FIG. 9, CPA at a dose of 100 mg/kg body weight induced up to 10-fold greater killing of the $CYP2B1^+$ tumors compared to wild type 9L tumors. The cytotoxicity of CPA toward parental 9L tumors, readily apparent in this in vivo study but not detectable in cell culture (c.f., FIGS. 2, 3, and 8), is a reflection of drug activation that occurs in the liver. Most strikingly, however, an additional approximately 10-fold tumor cell killing was achieved in the $CYP2B1^+RED^{+++}$ tumors. Thus, the combination of intratumoral CYP2B1 gene expression with RED gene transfer yielded a dramatic 50 to 100-fold overall increase in tumor cell kill in vivo over that provided by hepatic P450-catalyzed drug activation alone.

RED enzyme levels in human tumor cells: The experiments described above establish that RED overexpression leads to a substantial enhancement of P450-dependent drug activation in 9L gliosarcoma cells, both in vitro and in vivo, and that this enhancement can be achieved both in the case of rodent P450s and human P450s. Moreover, the data shown in Table 1 further establish that enhanced P450 metabolic activity is obtained in direct relation to the extent of RED enzyme expression, at least up to a level of RED activity corresponding to approximately 300 nmol cytochrome C reduced/minute/mg of microsomal protein. The basal, endogenous level of RED activity present in the 9L gliosarcoma cells used in these studies is approximately 50–60 nmol cytochrome C reduced/minute/mg of microsomal protein (cf., Table 1).

To ascertain whether this activity is comparable to that seen in human tumor cells, RED enzyme activity was measured in a panel of 60 individual human tumor cell lines (Boyd, M. R. and Paull, K. D., *Drug Develop Res.* 34:91–109 (1995)), belonging to nine distinct classes of human cancer (breast, central nervous system, colon, leukemia, lung, melanoma, ovarian, prostate and renal cancer). FIG. 10 shows that in 40 of the 60 human tumor cell lines present in this panel, representing each of nine human tumor cell types, RED enzyme activity is equal to or lower than the level present in 9L tumor cells, when corresponding cell microsome fractions are assayed. A similar general conclusion can be reached on the basis of the RED activities in human tumor cell line extracts ("S9 fraction") reported by Fitzsimmons, S. A., et al., *J Natl Cancer Inst* 88:259–269 (1996).

Thus, for each of these tumor cells, RED gene transfer combined with P450 gene transfer is expected to lead to enhanced P450- and RED-dependent activation of chemotherapeutic drugs. Moreover, even in the human tumor cell lines that express higher levels of RED activity, RED gene transfer is also expected to augment drug metabolic activity, since even at the highest RED activity present in these human tumor cells (285 nmol cytochrome C reduced/ minute/mg, in the case of one of the ovarian cell lines), increased RED expression led to a further increase in P450 metabolic activity (Table 1). Thus, the presently described method for increasing intratumoral drug metabolic activity and cancer chemotherapeutic activity by cotransfer of RED together with P450 to tumor cells is applicable to a broad range of human tumor cell types.

Discussion

It is known to those skilled in the art that transduction of a mammalian cytochrome P450 gene, such as CYP2B1, into either rodent or human tumor cells, renders these cells highly sensitive to the cytotoxic effects of anti-cancer drugs, such as CPA and IFA (Chen, L. and Waxman, D. J., *Cancer Res.* 55:581–589 (1995); Wei, M. X., et al., *Hum. Gene Ther.* 5:969–978 (1994); Chen, L., et al., *Cancer Res.* 56:1331–1340 (1996)). This Example shows that the therapeutic efficacy of this anti-cancer drug/P450 gene therapy system can be significantly enhanced by incorporation of a second gene, i.e., that encoding RED. RED mediates the transfer of electrons from NADPH to cytochrome P450 and participates in all microsomal P450-catalyzed enzyme reactions. RED is widely expressed in many cell types, including a wide range of tumor cells, and this widespread endogenous expression of RED in tumor cells establishes an important underlying basis for P450-based cancer gene therapy. Despite the fact that RED is already expressed endogenously in tumor cells at a level that is at least equal to the expressed P450 protein level, this Example shows that RED gene transfer substantially augments the drug sensitivity of target tumor cells transduced with a P450 gene and thus provides for a more efficacious anti-cancer drug activation system. This further sensitization is not only seen with CYP2B1, a rat P450 gene, but as shown below in Example 2, is also seen with two human P450 genes, CYP2B6 and CYP2C18, both of which are known to catalyze activation of CPA and IFA (Chang, T. K. H., et al., *Cancer Res.* 53:5629–5637 (1993); Chang, T. K. H., et al., *Pharmacogenetics* 7:211–221 (1997)). Moreover, as shown below in Example 3, it is also seen when using the human RED gene, both under conditions of normoxia, as well as under conditions of hypoxia, which characterize many solid tumors.

The further chemosensitization of P450-expressing tumor cells by RED gene transfer has several important implications for P450-based cancer gene therapy. First, the level of RED activity in a given tumor target will likely be an important determinant of the effectiveness of P450-based gene therapy in the absence of cotransfected RED. Second, tumor cells that have moderate or low levels of RED activity ($\leq 60$ nmol cytochrome C reduced/minute/mg) (c.f., FIG. 10) are prime targets for incorporating RED into any P450-based gene therapy strategy. Some therapeutic enhancement may also be anticipated in tumor cells with higher levels of endogenous RED expression, as indicated by the data presented in Table 1. Although under specialized circumstances (e.g., ablation of pituitary hormones leading to hypothyroidism) RED can be potentially rate-limiting for P450-catalyzed oxidative metabolism in liver cells as a consequence of the large molar excess of P450 over RED (Waxman, D. J., et al., *Mol. Pharmacol.*, 35:519–525 (1989)), the present study demonstrates that even in P450-transfected tumor cells where only a low level of P450 protein expression is achieved (Chen, L. and Waxman, D. J., *Cancer Res.* 55:581–589 (1995); Chen, L., et al., *Cancer Res.* 56:1331–1340 (1996)), and the ratio of RED to P450 is already equimolar or greater than equimolar, a significant enhancement of P450 metabolic activity can nevertheless be achieved through elevated expression of RED. Thus, the production of cytotoxic drug metabolites was significantly elevated in P450-expressing tumor cells that overexpress RED, as evidenced by the increased formation of 4-hydroxylated drug metabolites and by the enhanced bystander killing of co-cultured parental 9L tumor cells. This bystander effect, associated with a localized increase in activated drug metabolites, may lead to more efficient tumor cell killing even when only a small subset of tumor cells is transduced with the P450 gene. Overexpression of RED may greatly facilitate electron transfer from cellular NADPH to cytochrome P450. This is supported by the inventors' observation that the P450 inhibitor, metyrapone, was less effective in blocking drug toxicity in CYP2B1$^+$RED$^{+++}$ cells than in CYP2B1 +cells. Conversely, the RED inhibitors, AADP and DPI, despite their inherent toxicity to cells, effected greater reversal of CPA cytotoxicity in CYP2B1$^+$RED$^{+++}$ cells compared to CYP2B1$^+$ cells. This is the first demonstration, in an intact cell system, that RED inhibitors can protect cells from P450 gene transfer-mediated chemotherapeutic drug cytotoxicity, and suggests that these or other RED inhibitors may find use in the protection of host cells that become transduced with an anti-cancer drug-activating P450 gene.

The inventors have demonstrated that despite the well-established finding that an equal mole level of RED with P450 is sufficient to achieve maximal P450 monooxygenase activity, both in intact cells (Yamano, S., et al., *Mol. Pharmacol.* 36:83–88 (1989)) and in in vitro reconstituted systems (Miwa, G. T., et al., *J. Biol. Chem.* 253:1921–1929 (1978)), leading to the expectation that endogenous tumor cell RED levels would be more than sufficient to provide for rapid electron transfer to the comparatively low level of P450 protein that can be achieved by either viral or non-viral gene transfer methods, a substantial increase in chemotherapeutic drug activation and in tumor cell chemosensitivity can, in fact, be achieved by cotransfer of RED with P450. Thus, the level of cellular RED activity is critical to the effectiveness of P450 mediated anti-cancer drug activation, and the basal RED activity level may not be sufficient in the case of many tumors to catalyze maximal electron transfer to P450. Indeed, while RED activity is widely expressed in human tumor cells, large variations in the level of enzyme expression are found in individual tumor cells. The importance of endogenous RED activity was underscored by the inventor's experiment infecting 9L tumor cells with increasing amounts of Ad.CMV-2B1 in parental and RED-overexpressing 9L cells. RED overexpressing 9L cells were more sensitive to CPA than parental 9L cells when infected with same amount of Ad.CMV-2B1. Moreover, the drug cytotoxicity in Ad.CMV-2B1 -infected parental 9L cells was not further enhanced at multiplicities of infection above 200. In contrast, drug cytotoxicity in RED-overexpressing 9L cells was further enhanced at higher viral multiplicities. Accordingly, RED gene transfer will lead to an even greater increase in anticancer activity when using more efficient vectors that provide for a higher level of P450 gene transfer.

Given the significance of RED activity level as a factor in determining the sensitivity of tumor cells to P450-dependent chemotherapeutic drug activation, it is also apparent from the inventor's findings that factors which regulate endogenous levels of RED enzyme activity and RED gene expression are important modulators of P450-mediated drug activation. These include thyroid hormone, which is essential for full expression of P450 reductase in several tissues (Waxman, D. J., et al., *Mol. Pharmacol.* 35:519–525 (1989); Ram, P. A. and Waxman, D. J., *J. Biol. Chem.* 267:3294–3301 (1992)), as well as various drugs, such as phenobarbital and other xenobiotics that increase RED enzyme levels (Gonzalez, F. J. and Kasper, C. B., *Biochemistry* 20:2292–2298 (1981); Waxman, D. J., et al., *Biochemistry* 24:4409–4417 (1985)). In the case of P450-based cancer gene therapy applications, where the goal is to achieve maximal intratumoral chemotherapeutic drug activation with minimal systemic toxicity, the present invention adds an additional approach to down-regulating hepatic bioactivation of chemotherapeutic drugs, through the modulation of RED protein levels and RED enzyme activities.

EXAMPLE 2

Use of Human P450 Genes for P450/RED-Based Gene Therapy

CPA and IFA are widely used anticancer prodrugs that are bioactivated in the liver by specific cytochrome P450 (CYP) enzymes, with electron input from the flavoenzyme NADPH P450 reductase (RED). The therapeutic activity of these antitumor agents can be compromised by a low therapeutic index that is, in part, due to the systemic distribution of activated drug metabolites.

In this Example, recombinant retroviruses were used to deliver the following six different CPA- or IFA-metabolizing human CYP genes to 9L gliosarcoma cells: 2B6, 2C8, 2C9, 2C18 (Met$^{385}$ and Thr$^{385}$ alleles), 2C19, and 3A4. The impact of human CYP gene transfer, both alone and in combination with P450 reductase gene transfer (Chen, L., et al., *Cancer Res.* 57:4830–4837 (1997)), on the responsiveness to oxazaphosphorine therapy was evaluated both in vitro and in an in vivo tumor model system.

As discussed below, intratumoral P450 expression conferred substantial sensitivity to CPA cytotoxicity, with the most dramatic effects seen with CYP2B6. Strong CPA chemosensitivity was also seen following transduction of CYP2C18-Met, in spite of a very low level of CYP protein expression (>20-fold lower than 2B6).

In contrast to CPA, the cytotoxicity of IFA was greatest toward tumor cells transduced with CYP3A4, followed by CYPs 2B6 and 2C18-Met. A substantial further increase in chemosensitivity was achieved upon transduction of 2B6 or 2C18 -Met-expressing tumor cells with P450 reductase, which provided for more efficient intratumoral drug activation and cytotoxicity at lower drug concentrations. With 2B6 and RED-transduced tumor cells, CPA, but not IFA, conferred a strong cell contact-independent bystander cytotoxic effect on non-P450-expressing 9L cells. CPA treatment of 9L/2B6/RED and 9L/2C18-Met/RED tumors grown subcutaneously in immunodeficient scid mice resulted in a large enhancement of the liver P450-dependent antitumor effect seen with control 9L tumors, with no apparent increase in host toxicity (growth delay >25–50 days in RED tumors vs. approximately 5–6 days without P450). CYP2B6 and RED or CYP2C18-Met and RED are thus excellent gene combinations for use with CPA in P450/chemotherapeutic drug activation-based cancer gene therapy.

Materials and Methods

Abbreviations used: 9L/wt, wild-type 9L gliosarcoma cells; 9L/pBabe cells, pool of 9L cells infected with pBabe-puro control vector retrovirus; 9L/P450, 9L cells transduced with a human P450 gene; 9L/2B6/reductase and 9L/2C18-Met/reductase, 9L cells transduced with the indicated P450 cDNA and with P450 reductase.

Chemicals: CPA and IFA were obtained from the Drug Synthesis and Chemistry Branch of the National Cancer Institute (Bethesda, Md.). The chemically activated derivatives of CPA and IFA, 4-hydroxyperoxy-CPA and 4-hydroperoxy-IFA, were obtained from Nova Pharmaceutical Corp. (Bethesda, Md.). Puromycin hydrochloride was purchased from Sigma, and hygromycin was from Aldrich.

Construction of recombinant retroviruses: cDNAs encoding three human CYP 2C genes (Goldstein, J. A. and de Morais, S. M., Pharmacogenetics 4.285–299 (1994)), CYP2C8 (clone 7b), CYP2C18-Met$^{385}$ allele (clone 6b; GenBank HUM2C18), CYP2C18-Thr$^{385}$ allele (clone 29c; GenBank HUMCYP2C18), and CYP2C19 (clone 11a; GenBank HUMCYP2C19), each cloned in the EcoRI site of pBluescript-SK$^{+/-}$, were provided by Dr. J. Goldstein, National Institutes of Environmental Health Sciences. The human CYP cDNAs 2C9 (plasmid 217; Cys 144 variant, cloned in the EcoRI site of pUV1; GenBank HUMCYP2C9A), 2B6 (plasmid 328; cloned in the EcoRI site of pUC9; GenBank HUMCYP2BB), and 3A4 (plasmid 359; cloned in the EcoRI site of pGEM7zf+; GenBank HUMCYPNOA), were obtained from Dr. F. Gonzalez, National Cancer Institute. Rat P450 reductase cDNA (GenBank RATCYPRM) was provided by Dr. G. Gil, Univ. of Mass., Worcester (Chang, T. K. H., et al., Biochem. J. 291 (pt2):429–433 (1993)). Retroviral vectors of the pBabe series (Morgenstern, J. P. and Land, H., Nucleic Acids Res. 18.3587–3596 (1990)) which encode genes that confer resistance to either puromycin (pBabe-puro) or (pBabe-hygro) and are transcribed from an internal SV40 early promoter, were obtained from Dr. B. Speigelman, Dana Farber Cancer Institute. P450 cDNAs were cloned into the pBabe-puro multiple cloning site, which provides for transcription of the P450 gene from the retroviral LTR promoter. Rat P450 reductase cDNA (EcoRI-XhoI fragment encompassing the full-length cDNA) was subcloned into pBabe-hygro cut with EcoRI-SalI. In the final retroviral constructs, each of the human CYP cDNA retained the following lengths of 5'- and 3'-untranslated region (UTR) sequence: 2C8, 78 and 359 bp; 2C9, 11 and 369 bp; 2C18-Met$^{385}$, 43 and 341 bp; 2C18-Thr$^{385}$, 200 and 333 bp; 2C19, 6 and 268 bp; 3A4, 30 and 457 bp; and 2B6, 7and1563bp.

Construction of stable 9L gliosarcoma cell lines by retroviral infection: The ecotropic packaging cell line BOSC23 (Pear, W. S., et al., Proc. Natl. Acad. Sci. USA. 90:8392–8396 (1993)) ($2.5 \times 10^6$ cells in a 60 mm dish), obtained from Dr. J. Aster (Brigham and Women's Hospital, Boston), was cultured in 3 ml of DMEM containing 10% heat-inactivated fetal bovine serum, 584 g/L of L-glutamine, 100 units/ml penicillin, and 100 μg/ml streptomycin. Prior to transfection, the cells were changed to fresh media containing 25 μM chloroquine. Three hours later, 24 μg of each pBabe-based plasmid was transfected into the cells using calcium phosphate. Plasmid DNA was suspended in 0.5 ml of 0.25 M CaCl$_2$, then added drop-wise with shaking in a Falcon tube containing 0.5 ml of 2× Hepes-buffered saline solution (84 mM Hepes pH 7.1, 547 mM NaCl, 19.8 mM KCl, 0.7 mM Na$_2$HPO$_4$.2H$_2$O and 5.54 mM glucose). The mixture was added immediately to the cells and left for 5 hours before changing the medium. The total supernatant (3 ml) containing released viral particles was removed 48 hours later and used to infect 9L rat gliosarcoma cells ($0.5 \times 10^6$ cells in a 100 mm dish) in the presence of 4 μg/ml polybrene. Three hours later the medium was adjusted to 10 ml by addition of fresh DMEM. The cells were trypsinized 48 hours later and split into four 100 mm dishes. Selection for puromycin- or hygromycin-resistant 9L cells was carried out with 2 μg/ml puromycin and/or 250 μg/ml hygromycin for 2–3 days. Drug-resistant cells were propagated and then evaluated for CYP or P450 reductase enzyme activities and protein expression (see below). Coexpression of P450 enzymes and P450 reductase was achieved by infecting cells with retrovirus encoding a P450 gene, puromycin-selection of a pool of 9L cells expressing a specific P450 gene (9LIP450 cells), clonal selection of cells with elevated P450 levels (see below), followed by infection of the clonal 9L/P450 cell line with retrovirus encoding RED. Hygromycin selection for two days was then carried out to obtain pools of 9L/P450 cells that overexpress RED.

Clonal selection of 9LIP450 cell lines: Cells from each pool of puromycin-resistant, P450-expressing 9L cells were trypsinized and diluted to approximately 1 cell/50 μl, and then plated at calculated densities of 1, 3, and 5 cells/ well in a 96 well tissue culture plate. Wells containing single colonies were identified at confluency (approximately 15 days later) using a light microscope, then trypsinized and split into two wells of a 48 well tissue culture plate. One well of each clone was untreated and kept as a control, while the second well was treated with either 2 mM CPA, for 9L/2B6, 9L/2C8, 9L/2C9, 9L/2C18 and 9L/2C19 cells, or with 2 mM IFA for 9L/3A4 cells. Clones that exhibited an enhanced sensitivity to CPA or IFA toxicity were typically detected by day 2 or day 3 of drug treatment, that is approximately 2 days earlier than seen for the others; these clones were then propagated and further evaluated for P450 protein levels and enzyme activities. The yield of clones showing enhanced drug-sensitivity was 27 out of 36 for 9L/2B6, 20 out of 34 for 9L/3A4 and 4–5 out of 34 for the others. In the case of CYP3A4, each of the isolated clones grew more slowly than the original 9L13A4 pool or the 9L/wt or 9L/pBabe controls.

Slow-growing clones were occasionally seen for some of the 9L/2C isolates, but these were not selected for subsequent studies.

Western blot analysis: Microsomes were prepared from near confluent 100 mm dishes of each P450-expressing 9L cell line. Cells were washed with ice cold 50 mM KPi 1 mM EDTA, pH 7.4, and then scraped into 2 ml of the same buffer and sonicated sufficient time for cell lysis (approximately 20 seconds) in 15 ml Corex tubes. The homogenate was centrifuged at 12,000 rpm and 4° C. for 20 minutes, and the resultant supernatant then ultracentrifuged for 60 minutes at 45,000 rpm and 4° C. The microsomal pellet was resuspended by sonication in 50 mM KPi 1 mM EDTA, 20% glycerol, pH 7.4. Microsomal protein (60 μg/well) was electrophoresed through a 10% SDS-polyacrylamide gel then transferred to nitrocellulose, and further probed with rabbit polyclonal anti-CYP2B6, anti-CYP3A4, and anti-CYP2C antibodies prepared against short COOH-terminal synthetic peptides (Edwards, R. J., et al., Biochem Pharmacol. 49:39–47 (1995)), and provided by Dr. R. Edwards (Royal Postgraduate Medical School, London). Lymphoblast-expressed CYP2B6 and CYP3A4 (Gentest Corp., Woburn, Mass.) and yeast-expressed CYPs 2C8, 2C9, 2C18, 2C1 9 (provided by Dr. J. Goldstein, NIEHS) (Chang, T. K., et al., Pharmacogenetics 7:211–221 (1997)), were electrophoresed at 0.3–1.2 pmol P450/well, and used as standards to quantitate P450 levels in the 9L cells.

BROD and P450 reductase assays: BROD activity was assayed using 70 μg of microsomal protein in 1 ml containing 0.1 M KPi, pH 7.4, 0.1 mM EDTA and 4 μM BROD (Molecular Probes, Inc., Junction City, Oreg.). Reactions were started by adding 1 mM NADPH (final concentration), and the release of the fluorescent metabolite resorufin was measured over an 8 minute time period at 20–25° C. using a Shimadzu RF-1501 fluorescence spectrophotometer. Fluorescence was read at 550 nm (excitation) and 586 nm (emission). Activity values were quantitated using resorufin standard. P450 reductase activity was assayed in 0.3 M KPi buffer, pH 7.7 using 20 μg microsomal protein by monitoring the NADPH-dependent reduction of cytochrome C at 550 nm at 30° C. (E=21 mM$^{-1}$ cm$^{-1}$).

RT-PCR analysis of CYP2C18 expression: Total RNA from 9L/P450 or 9L/pBabe cells prepared from confluent 100 mm dishes (Chirgwin, J. M., et al., *Biochemistry* 18:5294–5299 (1979)) was treated with RQ1 DNASE (DNASE free) (Promega). Five μg of treated RNA was then heated at 70° C. for 10 minutes in 11 μl of DEPC-treated H$_2$O containing 10 pmol of a reverse transcriptase (RT) primer. Two μl of 10× RT buffer (Promega), 2 μl of 0.1 M DTT, 40 Units RNasin and 100 Units of MMLV reverse transcriptase were then added in a final volume of 20 μl. Samples were incubated at 45° C. for 1 hour, followed by heat inactivation at 60° C. for 2 minutes. RT-PCR was carried out using 1 μl of the reverse transcription reaction. Negative controls for RT-PCR consisted of mock reverse transcription mixtures, containing all components except for reverse transcriptase.

Cytotoxicity assays: To evaluate the chemosensitivity of the P450-expressing 9L tumor cells, cells were plated in triplicate at 500–2000 cells/well of a 48-well plate 18–24 hours prior to drug treatment, unless indicated otherwise. Cells were typically treated with 0–2 mM CPA or IFA continuously for 4 days. Cells remaining after this time were quantitated using a crystal violet/alcohol-extraction assay. Briefly, culture dishes were washed once with phosphate buffered saline (PBS), stained for 10 minutes with crystal violet (1.25 g crystal violet (Sigma) dissolved in 500 ml containing 50 ml of 37% formaldehyde and 450 ml methanol), and then washed with PBS, twice for 20 minutes per wash. Absorbance values were measured in an SLT Spectra microtiter plate reader using a 595 nm filter. Background absorbance determined from wells containing culture media alone was subtracted from each value. Data are presented as cell number relative to drug-free controls, mean±SD values for triplicate samples, unless indicated otherwise. Error bars not seen in the individual figures are too small to be visible.

Bystander cytotoxicity/co-culture experiments: 9L/pBabe cells were plated in duplicate at 10$^5$ cells/well in the lower chamber of a 6-well Falcon co-culture plate (30 mm diameter wells) (Falcon 3046). 9L/2B6/reductase cells were plated in 25 mm cell culture inserts (0.4 μm pore size; Falcon 3090), at dilutions ranging from 0. 1 to 6 times the number of 9L/pBabe cells plated in the lower chamber. 24 hours after plating the cells, culture medium was aspirated from both compartments, and then replaced with 2 ml of fresh DMEM medium in the lower wells and 1 ml containing 2 or 3 mM CPA or IFA in the upper cell culture insert (final drug concentration, 0.67 or 1 mM, as indicated in each experiment). Relative cell numbers were quantitated 4 days later by crystal violet staining.

Semicarbazide trapping/fluorescence assay for 4-hydroxy metabolites: 9L/P450 cells were seeded on a 48 well plate in duplicate at 2×10$^4$ cells/ well. 24 hours later, 2 mM CPA or 2 mM IFA was added to the cells together with 5 mM semicarbazide (final concentration) in 1 ml of DMEM, pH 7.4, to trap and stabilize the initial 4-hydroxy metabolite. Cells were counted 24 hours after drug addition, and the culture medium was analyzed for 4-hydroxy-CPA or 4-hydroxy-IFA according to Chen, L., et al., *Cancer Res.* 57:4830–4837 (1997), as follows. Culture media, 400 μl, was removed and then treated with 160 μl of ice cold 5.5% (w/v) ZnSO$_4$, 160 μl ice cold saturated Ba(OH)$_2$, and 80 μl ice cold 0.01 M HCl. The mixture was vortexed and then centrifuged at 16,000 g for 15 minutes. 300 μl of the supernatant was transferred under dim light to a clean tube containing 540 μl of water and 160 μl of freshly prepared fluorescent reagent (60 mg 3-aminophenol and 60 mg hydroxylamine-HCl per 10 ml of 1 M HCl). The tubes were vortexed and heated at 90° C. for 20 minutes. Fluorescent readings were obtained at 350 nm (excitation), and 515 nm (emission) using 800 μl of each sample. Fluorescent values were converted to nmol 4-hydroxy metabolite/ml of original culture media based on standard curves generated using 4-hydroperoxy-CPA and then normalized to units of nmol 4-hydroxy metabolite formed per 24 hours per 10$^6$ cells.

Tumor Growth Delay Assay: Six week old male ICR/Fox Chase/outbred immunodeficient scid mice (Paine-Murrieta, G. D., et al., *Cancer Chemother Pharmacol.* 40:209–214 (1997)) (Taconic Farms, Germantown, N.Y.) weighing 26–31g were given subcutaneous tumor cell injections to form solid tumors. Tumor cells were grown in culture to approximately 75% confluency, harvested by trypsin digestion, washed in PBS, resuspended in fetal bovine serum-free DMEM at a concentration of 8×10$^6$ cells/ml and kept on ice. Mice were shaved on both hind flanks, and then were injected subcutaneously on the left flank with 4×10$^6$ 9L/pBabe tumor cells, and on the right flank with 4×10$^6$ of either 9L/2B6/reductase or 9L/2C18-Met/reductase tumor cells (8 mice/group). Tumor cell injections were in a volume of 0.5 ml of serum-free DMEM using a ½ inch 27 g needle and 1 ml syringe. Tumor growth was monitored twice a week using Vernier calipers (Manostat Corp., Switzerland) to measure tumor area. On days 26 and 27 after tumor cell inoculation, 4 animals from each group (four 9L/pBabe:9L/2B6/reductase mice and four 9L/pBabe:9L/2C18-Met/reductase mice) received daily intraperitoneal injections of CPA at 150 mg/kg dissolved in 0.3 ml of 0.9% NaCl. The remaining animals received saline injections. Average tumor areas ranged from 80–145 mm$^2$ at the time of CPA injection. Mice were given a second course of CPA treatment (150 mg/kg×2 daily injections) beginning 24–29 days after the first CPA injection, as indicated in each experiment.

Results

Retroviral expression of human P450s in 9L gliosarcoma cells: 9L cells were infected with pBabe-based retroviral particles (Morgenstern, J. P., and Land, H., *Nucleic Acids Res.* 18:3587–3596 (1990)) produced in the packaging cell line BOSC23, and engineered to code for each of the following six human P450 genes: CYPs 2B6, 2C8, 2C9, 2C18, 2C19 and 3A4. These six P450s have each been shown to activate CPA or IFA in a heterologous cDNA expression system (Chang, T. K. H, et al., *Pharmacogenetics* 7:211–221 (1997); Chang, T. K. H., et al., *Cancer Res.* 53:5629–5637 (1993)). Included in these studies were 2C18-Met$^{385}$ and 2C18-Thr$^{385}$, two allelic variants of CYP2C18 which display differences in their oxazphosphorine metabolism activities (Chang, T. K. H, et al., *Pharmacogenetics* 7:211–221 (1997)). This retroviral approach to stable transfection is rapid and yields a pool of cells containing many thousands of independent clones, each of which expresses the P450 gene at a random integration site. In each case, ≧60–70% of the infected 9L tumor cells acquired resistance to puromycin, indicating a high efficiency for retroviral gene delivery. P450 protein expression was readily detectable in the pools of CYP2B6 and 2C9 cells, as shown by Western blot analysis of isolated cellular microsomes (FIG. 11A). In the other cases, the level of P450 protein expression in the pool of puromycin-resistant cells was low (2C8, 2C19) or not detectable (CYP3A4, and both CYP2C18 alleles) using our analytical methods.

Clonal selection was carried out to obtain individual 9L/P450 clones with higher levels of P450 protein expression. Clones showing enhanced sensitivity to CPA or IFA (see, Methods) were propagated and analyzed by Western blotting. In each case, the 9L/P450 clones selected on the basis of increased sensitivity to CPA or IFA had a higher specific P450 protein content (FIG. 11) and higher P450 enzyme activity (see, FIG. 12). The microsomal P450 content of the selected clones, determined by Western blotting using lymphoblast-expressed or yeast-expressed human P450s as standards, is presented in Table 2. The highest levels of expression were observed with 9L/2B6 (20–25 pmol P450/mg microsomal protein) and 9L/2C9 (10–15 pmol/mg) cells, while 2C18-Met was the lowest ($\leq 0.3$ pmol/mg). 9L/2C8, 9L/2C18-Thr, 9L/2C19 and 9L/3A4 cells exhibited intermediate levels of P450 expression (0.5–3 pmol/mg). Expression of both 2C18 transcripts was confirmed by RT-PCR. These expressed P450 protein levels can be compared to an endogenous RED protein level in the 9L cells of 18 ±3 pmol/mg (see Table 1 of Example 1 and FIG. 14).

TABLE 2

P450 protein content in 9L/P450 clonal cell lines

| 9L/P450 Clonal Cell Lines | Clone Number | Specific P450 Content (pmol P450/mg microsomal protein) |
| --- | --- | --- |
| 2B6 | 1 | 20–25 |
| 2C8 | 2 | 0.5–1 |
| 2C9 | 1 | 10–15 |
| 2C18-Met | 3 | $\leq 0.3$ |
| 2C18-Thr | 2 | 0.5–1 |
| 2C19 | 2 | 1.5–3 |
| 3A4 | 3 | 1–2 |

Individual P450 clones were selected from pools of puromycin-resistant 9L/P450 cells on the basis of their enhanced sensitivity to CPA (or to IFA, in the case of 9L/3A4) as described under Methods. Microsomes prepared from the indicated clones were analyzed on Western blots (as in FIG.11) for P450 protein content in comparison to a standard curve based on 0.2–1 pmol of the corresponding cDNA-expressed P450 protein standard using either a lymphoblast cDNA-expression system (CYPs 2B6, 3A4; Gentest Corp.(Woburn, MA)) or a yeast expression system (Chang, T.K.H., et al, Pharmacogenetics. 7:211–221 (1997)). Data are shown as a range of values from two or three separate experiments.

BROD activity of the tumor cell-expressed P450genes: P450-dependent BROD activity, which is catalyzed by many human P450 enzymes at various rates, was used to monitor the enzymatic activity of the transfected P450 genes. FIG. 12 shows that all of the P450-expressing cell lines exhibited higher BROD activity than parental (wild-type), 9L cells (9L/wt), or 9L/pBabe controls. Moreover, the isolated 9L/P450 clones each expressed higher BROD activity than the original 9L/P450 retroviral pools. 9L/P450 clonal cell lines chosen for further study (marked by arrows in FIG. 12) were selected on the basis of their level of P450 expression (Western blotting and BROD activity) and their CPA or IFA sensitivity.

Cytotoxicity of CPA and IFA toward P450-expressing 9L tumor cells: growth inhibition assays: To evaluate the impact of retroviral P450 transduction on 9L chemosensitivity, cells were cultured in the presence of various concentrations of CPA or IFA, and cytotoxicity was evaluated by a growth inhibition assay scored 4 days later. 9L/wt and 9L/pBabe cell lines, used as P450-negative controls, were insensitive to millimolar concentrations of both CPA (FIG. 13A) and IFA (FIG. 13C). By contrast, all of the P450-expressing 9L cells showed a concentration-dependent growth inhibition by CPA. 9L/2B6 cells were the most susceptible to CPA cytotoxicity (>95% growth inhibition at 1 mM CPA), consistent with the high catalytic activity of CYP2B6 with respect to CPA activation (Chang, T. K. H., et al., Cancer Res. 53:5629–5637 (1993); Roy et al., 1998, manuscript in preparation) and the comparatively high level of CYP2B6 protein expression achieved using this retroviral expression system (Table 2). Each of the other tumor cell lines, except 9L/2C8, also showed significant acquired drug sensitivity: at 1 mM CPA, approximately 60% growth inhibition was observed for 9L/2C9 and 9L/2C18-Thr cells, 75–85% inhibition was obtained for 9L/2C19 and 9L/2C18-Met (FIG. 13B) and approximately 90% growth inhibition for 9L/3A4 (FIG. 13A). The cytotoxicity of CPA toward 9L/2C18-Met cells is especially remarkable, given the very low level of CYP2C18-Met protein expression in these tumor cells (Table 2). This effect is likely due to the low Km and high catalytic efficiency CYP2C18-Met for CPA (Chang, T. K. H., et al., Pharmacogenetics 7:211–221 (1997)).

In contrast to the moderate to high sensitivity of many of the 9L/P450 cell lines to CPA, only 3 of the 9L/P450 cell lines showed significant sensitivity toward IFA when tested at concentrations up to 1 mM. 9L/3A4 cells were, by far, the most sensitive to IFA, although significant IFA growth inhibition was also achieved in 9L/2B6 and 9L/2C18-Met cells (FIGS. 13C, 13D). The other P450-expressing cell lines were resistant to IFA under these conditions (FIG. 13D).

P450 reductase transduction further enhances cytotoxic responses: The inventors next investigated whether the endogenous level of RED in 9L tumor cells was sufficient to maximally support CPA and IFA activation catalyzed by the transduced human P450 genes. RED activities measured in microsomes prepared from the 9L/P450 cell lines were not substantially different from 9L/wt and 9L/pBabe controls (FIG. 14). An approximately 5-fold increase in P450 reductase activity was, however, obtained following retroviral transduction of the 9L/2B6 and 9L/2C18-Met cells with P450 reductase (FIG. 14). This overexpression of P450 reductase markedly increased the cytotoxicity of both CPA (FIG. 15A) and IFA (FIG. 15B) toward the 9L/2B6 and 9L/2C18-Met cells, particularly at lower drug concentrations. This effect was achieved even though endogenous RED levels in these cells (18±3 pmol/mg) are comparable to (9L/2B6) or in vast molar excess of (9L/2C18-Met) the expressed P450 protein levels (cf., Table 2). In control experiments, RED transduction alone, in the absence of P450, also increased P450 reductase activity approximately 5-fold, but did not confer CPA or IFA cytotoxicity (FIG. 15). Thus, RED gene transfer not only increases tumor cell cytotoxicity at a given drug concentration, but may provide the opportunity to achieve significant antitumor activity with a reduction in drug dosage. It is also apparent from these studies that 9L growth inhibition required higher concentrations of IFA than CPA, for both CYP2B6 and CYP2C18-Met (FIG. 15B vs. 15A). This is, in part, a reflection of the greater intrinsic sensitivity of 9L tumor cells to activated CPA, as compared to activated IFA, as determined in cytotoxicity assays using the corresponding chemically activated 4-hydroperoxy compounds (FIG. 16). In this light, the substantially greater sensitivity of 9L/3A4 cells to IFA compared to CPA (FIG. 13C vs. 13A) must, indeed, reflect the higher rate of prodrug activation catalyzed by CYP3A4 with IFA compared to CPA (Chang, T. K. H., et al., Cancer Res. 53:5629–5637 (1993); Roy et al., 1998, manuscript in preparation).

RED-enhanced metabolic activation of CPA and IFA in transduced tumor cells: To investigate whether the RED-enhanced cytotoxicity of CPA and IFA toward 9L/2B6 and 9L/2C18-Met tumor cells was due to increased prodrug activation, the levels of P450-generated 4-hydroxy metabolites in culture supernatants from each cell line were measured (FIG. 17). RED transduction stimulated a significant increase in cytotoxic metabolites accumulating in the culture medium, both for CYP2B6 and CYP2C18-Met cells. By contrast, transduction of RED in 9L parental cells did not stimulate drug activation. These studies also showed that in 9L/3A4 cells, IFA 4-hydroxylation was greater than CPA 4-hydroxylation, consistent with their preferential sensitivity to IFA (FIGS. 13, 15), while 9L/2C8 cells showed IFA metabolite levels just above the 9L/pBabe background (FIG. 17).

Impact of RED on bystander killing effect: CPA treatment of tumor cells transduced with rat P450 gene CYP2B1 is associated with a significant bystander cytotoxic effect, whereby neighboring tumor cells that do not express the P450 drug susceptibility gene also become sensitized to the prodrug (Chen, L. and Waxman, D. J., *Cancer Research.* 55:581–589 (1995); Chen, L., et al., *Cancer Res.* 56:1331–1340 (1996)). Since 9L12B6/reductase cells were themselves more readily killed by CPA and IFA than 9L/2B6 cells (FIG. 15), the inventors' investigated whether bystander tumor cells were also more chemosensitive when cultured with P450 reductase-transduced 9L12B6 cells. Bystander cytotoxicity was evaluated by using cell culture inserts to physically separate the drug-activating 9L/2B6/reductase (or 9L/2B6) tumor cells from the P450-deficient bystander 9L/pBabe cells. FIG. 18A demonstrates that 9L/2B6/reductase cells exposed to CPA confer a approximately 3-fold stronger bystander killing of 9L/pBabe cells than do 9L/2B6 cells, as judged from the 9L/P450 to 9L/pBabe cell ratio required to effect 50% bystander cytotoxicity. Follow-up experiments demonstrated that IFA does not display the strong bystander cytotoxicity seen with CPA: CPA treatment of 9L/2B6/reductase cells results in approximately 40% bystander toxicity toward non-P450 tumor cells when the ratio of P450: non-P450 cells is approximately 0.5–1, and ≧80% toxicity toward the non-P450 cells as the cell ratio is increased to >3 (FIG. 18B). In contrast, IFA exerted only a modest bystander cytotoxicity to the non-P450-expressing pBabe controls (c.f., up to approximately 25% bystander cytotoxicity at cell ratios up to 3: 1, and a maximum of approximately 50% bystander cytotoxicity at a cell ratio of 6: 1) (FIG. 18B). This observation, together with the greater intrinsic potency of activated CPA compared to activated IFA in the 9L gliosarcoma model (FIG. 16) demonstrates that CPA is a superior choice compared to IFA for use in conjunction with CYP2B6 and RED gene therapy.

Evaluation of human P450/P450 reductase-based gene therapy in a scid mouse model: The impact of human P450 gene transfer on 9L gliosarcoma chemosensitivity was evaluated in vivo using the immunodeficient scid mouse solid tumor model (Paine-Murrieta, G. D., et al., *Cancer Chemother. Pharmacol.* 40:209–214 (1997)). The scid mouse model is free from the complications associated with immunogenic responses toward 9L tumors expressing human P450 genes, and it eliminates any contributions from immunological components to bystander cytotoxicity (Gagandeep, S., et al., *Cancer Gene Ther.* 3:83–88 (1996)).

Figure 19A:
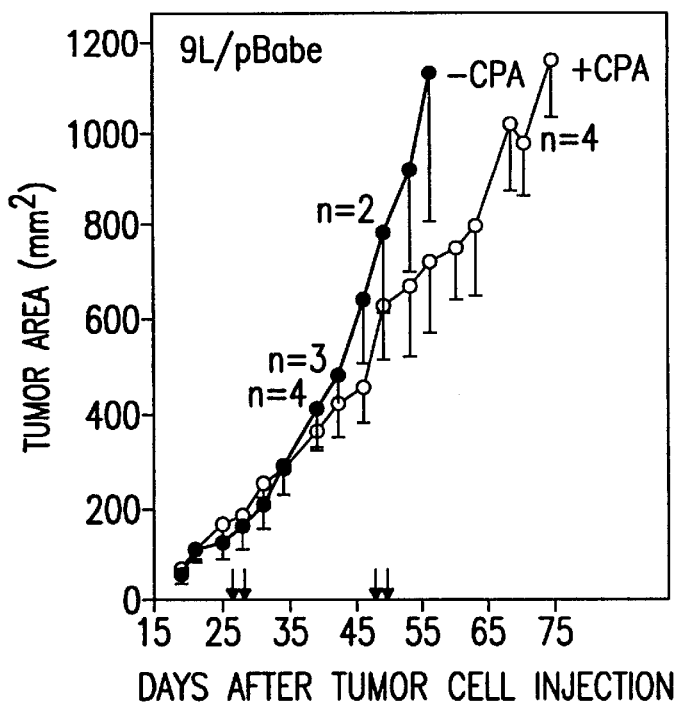
Figure 19B:
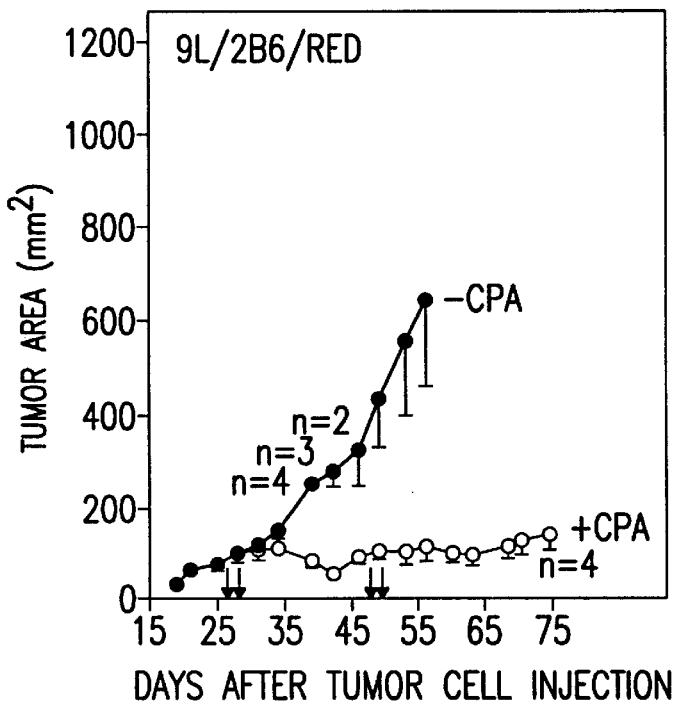

Scid mice were inoculated subcutaneously with 9L/pBabe tumors on the left flank and with 9L/2B6/reductase tumors on the right flank. This experimental design enabled us to control for any systemic effects that the P450-expressing tumor might have on liver P450 metabolism. In the absence of drug treatment, 9L/2B6/reductase tumors grew at a somewhat slower rate than 9L/pBabe tumors, as had been observed for the cells in culture (FIG. 19B vs. 19A). Mice were treated with CPA given as two daily intraperitoneal injections at 150 mg/kg body weight on days 26 and 27 after tumor implantation, at which time the tumors were well-established in all the mice. This initial round of drug treatment resulted in no growth delay for the 9L/pBabe tumors compared to saline-treated controls (FIG. 19A, –CPA vs. +CPA). By contrast, growth of the 9L/2B6/reductase tumors in the same mice was fully blocked by CPA treatment (FIG. 19B). Administration of a second cycle of CPA treatment approximately 3.5 weeks after the first cycle (marked by vertical arrows along x-axis; FIG. 19) effected a modest growth delay effect against 9L/pBabe control tumors, while it prolonged the strong anti-tumor effect seen in the case of 9L/2B6/reductase tumors until at least day 75 after tumor inoculation.

Figure 19C:
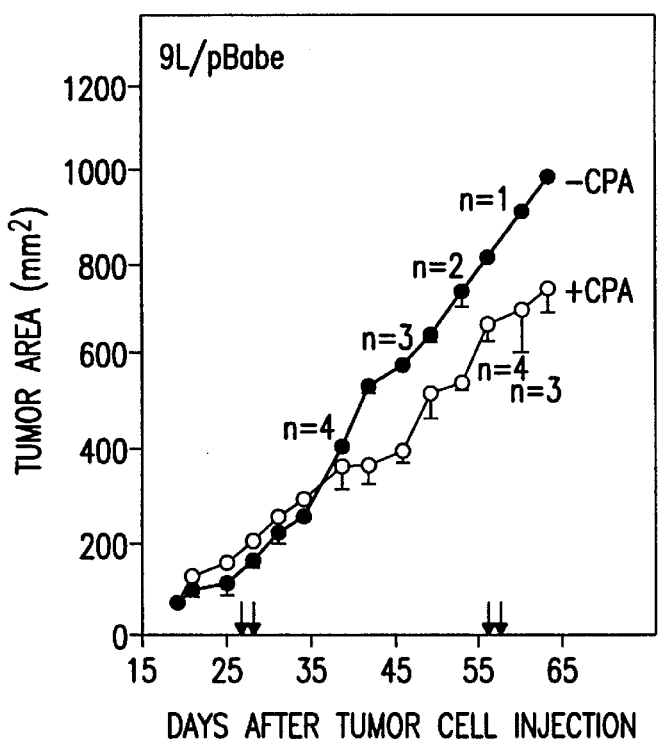
Figure 19D:
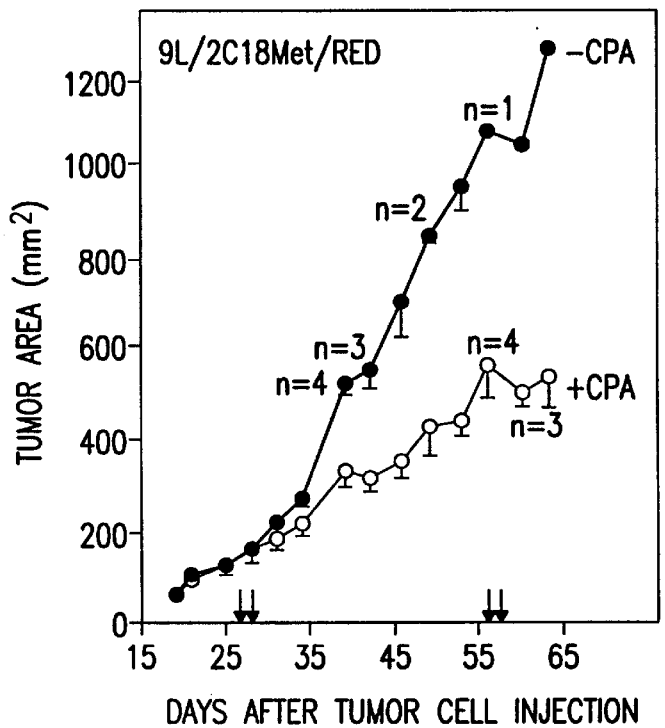

In an experiment designed to evaluate the impact of CYP2C18-Met gene therapy, CPA treatment effected a modest growth delay effect (approximately 5–6 days) toward the 9L/pBabe control tumors, which likely is a consequence of liver P450-catalyzed drug activation (FIG. 19C). By contrast, a significant, albeit incomplete growth inhibition of the 9L/2C18-Met/reductase tumors was observed (growth delay of at least 25 days) (FIG. 19D). This effect is especially striking when taken in the context of the very low level of P450 protein expression in the 9L/2C18-Met tumor cells (Table 2).

Discussion

The primary goals of the study presented in this Example were: 1) to extend earlier preclinical cancer gene therapy studies based on the rat CYP2B1 gene; 2) to identify human P450 genes that serve as suitable candidates for P450 and RED-based prodrug activation/cancer gene therapy; 3) to assess the extent to which an improvement in the efficiency of intratumoral drug activation catalyzed by human P450s can be achieved by cotransfer of the RED gene; and 4) to determine whether CPA and IFA both exhibit bystander cytotoxic effects when activated within tumor cells by human P450 enzymes in combination with RED.

Transduction of the rat gliosarcoma cell line 9L with replication-defective retroviral particles encoding each of six human P450 genes was found to chemosensitize the tumor cells to the cytotoxic effects of CPA, albeit with different apparent efficiencies (2B6>2C18-Met~3A4>others). In the case of IFA, CYP3A4 was the most effective in chemosensitizing the target tumor cells, followed by CYPs 2B6 and 2C18-Met. A substantial further improvement in chemosensitivity toward CPA and IFA was obtained by transduction of P450-expressing tumor cells with the P450 reductase gene. This led to a striking growth delay (>50 days) following CPA treatment of 2B6 and P450 reductase-transduced tumors grown in vivo in scid mice, where complications associated with immune rejection (Tapscott, S. J., et al., *Proc Natl Acad Sci USA.* 91:8185–8189 (1994)) and immunological contributions to bystander cytotoxicity (Gagandeep, S. et al., *Cancer Gene Ther.* 3:83–88 (1996)) are avoided. A significant, albeit less dramatic, CPA growth delay (>25 days) was seen with 9L/2C18-Met/reductase tumors, despite their very low P450 expression level. The human CYP genes 2B6 and 2C18-Met are thus strong candidates for use in CPA-based P450 gene therapy.

The six human CYP genes investigated in this study were expressed in the transduced clonal 9L tumor cell lines at widely different protein levels (≦0.3 to 20–25 pmol P450 protein/mg microsomal protein). Although P450 protein levels and CPA cytotoxicity were somewhat lower in the corresponding initial pools of transduced tumor cells, the rank order of P450 protein expression level was similar (2B6>2C9>2C8~2C19>2C18, 3A4). This indicates that the large differences in P450 protein levels in the isolated clonal cell lines do not primarily reflect differences in the site of retroviral integration. Rather, since all six P450 genes were transcribed from the same long terminal repeat (LTR) retroviral promoter, the observed differences in P450 protein expression levels are more likely to be due to differences in the stabilities of the individual P450 proteins and their mRNAs. CYP2B6 was expressed at the highest level, and correspondingly, CYP2B6 conferred on the 9L tumor cells the greatest CPA sensitivity. CYP2B6 is thus the gene of choice for CPA-based cancer gene therapy, both in terms of its apparent greater protein/mRNA stability suggested by the current study, and for its high inherent catalytic activity for CPA 4-hydroxylation and its low rate of CPA deactivation by N-dechloroethylation (Roy et al., 1998, manuscript in preparation). However, CYP2C18-Met is also a useful candidate for CPA-based cancer gene therapy, given the high chemosensitization achieved in CYP2C18-Met-expressing cells in the context of very low expressed P450 protein levels. Higher levels of CYP2C18 protein expression may be achievable using improved retroviral or other vectors, including non-viral vectors for gene delivery presently being developed (Kim, V. N., et al., *J. Virol.* 72:811–816 (1998); Nakanishi, M., *Critical Rev Ther Drug Carrier Systems.* 12:263–310 (1995); Pawelek, J. M., et al., *Cancer Res.* 57:4537–4544 (1997); Robbins, P. D., et al., *Trends Biotechnol.* 16:35–40 (1998)).

In contrast to the effective intratumoral activation of CPA by a broad range of P450s, intratumoral IFA activation was catalyzed by a more restricted subset of the human P450 genes investigated. As anticipated from studies using expressed P450 cDNAs and human liver microsomes (Chang, T. K. H., et al., *Pharmacogenetics* 7:211–221 (1997); Chang, T. K. H., et al., *Cancer Res.* 53:5629–5637 (1993)), CYP3A4 was the most potent activator of IFA, followed by CYP2B6 and CYP2C18-Met. The chemosensitization to IFA conferred by CYP3A4 (FIG. 13C) is striking, given the much lower level of expression of this P450 gene compared to CYP2B6 (Table 2), and given the intrinsic lower cytotoxicity of activated IFA toward 9L tumor cells compared to activated CPA (FIG. 16). In the case of CYP3A4, the lower level of tumor cell P450 protein may, in part, reflect toxicity of the CYP3A4 gene to the 9L cells, as suggested by the slower growth rate that was repeatedly obtained upon retroviral transduction with CYP3A4, both in retroviral pools and in individual clones, as noted above. This apparent toxicity of CYP3A4 could, on its own, lead to an enhanced chemotherapeutic effect. On the other hand, if this property is not desirable, it can be circumvented by use of an inducible promoter (Hofmann, A., et al., *Proc. Natl. Acad. Sci. USA.* 93:5185–5190 (1996); Massie, B., et al., *J Virol.* 72:2289–2296 (1998)), thereby augmenting intratumoral expression of CYP3A4 in the context of IFA-based gene therapy. However, CYP3A4 is not likely to exhibit toxicity toward all tumor cells, since slower cell growth has not been described in other mammalian CYP3A4 expression systems (Schneider, A., et al., *Arch Biochem Biophys.* 332:295–304 (1996)).

Although 4-hydroxy-CPA and 4-hydroxy-IFA yield distinct DNA-crosslinks (five vs. seven atoms in the crosslink, respectively), the two drugs act via similar mechanisms in eliciting apoptosis. Nevertheless, 9L gliosarcoma cells were found to be approximately 3-fold more sensitive to activated CPA compared to activated IFA. This differential cytotoxic effect was most evident at lower drug concentrations, which may be particularly relevant to the clinical situation. IFA is known to be activated by hepatic P450s less efficiently than CPA, and is also more extensively deactivated by the N-dechloroethylation pathway (Chang, T. K. H, et al., *Cancer Res.* 53:5629–5637 (1993); Fleming, R. A., *Pharmacotherapy* 17:146S–154S (1997); Kaijser, G. P., et al., *Anti-cancer Res.* 13:1311–1324 (1993)) Although the N-dechloroethylation by-product chloroacet aldehyde is generally not considered to be an active, chemotherapeutic metabolite when generated via hepatic P450 metabolism, it may nevertheless contribute to IFA cytotoxicity when it is generated within the target tumor cell in situ, in the context of P450-based cancer gene therapy. This possibility is suggested for CYP2B6-expressing tumor cells, which were sensitized to both CPA and IFA cytotoxicity, despite the fact that CYP2B6 metabolizes IFA primarily via the N-dechloroethylation pathway to yield chloroacet aldehyde rather than by 4-hydroxylation, the major CYP2B6-catalyzed metabolic route for CPA (Roy et al., 1998, manuscript in preparation).

Important differences between CYP2B6-catalyzed CPA and IFA metabolism were also evident from co-culture experiments, where CPA could mediate a striking bystander cytotoxic effect, but IFA could not. This intriguing finding may relate to the lower intrinsic cytotoxicity of 4-hydroxy-IFA compared to 4-hydroxy-CPA in this tumor cell line, coupled with the fact that CYP2B6 primarily metabolizes IFA via an N-dechloroethylation pathway that generates chloroacet aldehyde, which likely contributes to the 9L/2B6 cell's chemosensitivity in these studies, but may confer little or no bystander cytotoxicity. Since the bystander effect provides an important mechanism to enhance the effectiveness of prodrug activation-based cancer gene therapy by compensating for gene transfer efficiencies that may be well below 100% (Pope, I. M., et al., *Eur J. Cancer* 33:1005–1016 (1997)), IFA-based P450 gene therapy is not likely to be as effective using CYP2B6, and will require a more active catalyst of IFA 4-hydroxylation, such as CYP3A4 (FIG. 13C).

The studies described above in Example 1 have shown that co-expression of rat RED with rat CYP2B1 leads to enhanced chemotherapeutic responses (Chen, L., et al., *Cancer Res.* 57:4830–4837 (1997)). This finding was unexpected, in view of the fact that the level of endogenous RED in 9L gliosarcoma cells is at least equimolar to the expressed P450 protein level, and should thus provide for maximal P450 catalytic activity (Yamano, S., et al., *Molec. Pharmacol.* 35:83–88 (1989). Large increases in tumor cell sensitivity to CPA and IFA were also seen in the present study following retroviral transduction of RED, not only with CYP2B6-expressing tumor cells, but also with 9L/CYP2C18-Met cells, which have an extremely low expressed P450 protein level (Table 2). Accordingly, coexpression of RED with cytochrome P450 was shown to be beneficial both under conditions of low P450 protein expression, and under conditions where high expressed P450 protein levels were obtained. The increased chemosensitivity of 9L/P450 cells transduced with a RED gene was paralleled by an enhanced accumulation of active metabolites for both CPA and IFA (FIG. 17) and by a substantial increase in bystander cytotoxicity (FIG. 18A). RED gene transfer in the absence of P450 expression did not confer any chemosensitivity to CPA or IFA, confirming the cytochrome P450 dependence of these enhanced cytotoxic responses.

Of the four human CYP2C genes, CYP2C18 was the most active catalyst of CPA and IFA 4-hydroxylation (Chang, T. K. H., et al., *Pharmacogenetics* 7:211–221 (1997)), and in the study described in this Example, CYP2C18 was the most active in chemosensitizing 9L gliosarcoma cells to both CPA and IFA. Of the two CYP2C18 alleles studied, CYP2C18-Met was particularly active, despite its very low level of expression, as noted above. Indeed, CYP2C18-Met mediated a 9L cell killing effect which was comparable to that seen in CYP3A4-expressing tumor cells, where the P450 protein expression level was several-fold higher. This observation has important implications both for the utility of CYP2C18-Met for CPA-based cancer gene therapy, and with respect to its role in CPA and IFA activation in human liver tissue. Whereas CYP3A4 was the most abundant P450 in a typical human liver sample, CYP2C18 was in much lower abundance (Furuya, H., et al., *Mol Pharmacol.* 40:375–382 (1991); Shimada, T., et al., *J Pharmacol Exp Ther.* 270:414–423 (1994)). Although CYP2C18 was an active CPA and IFA 4-hydroxylase when assayed in a yeast cDNA expression system (Chang, T. K. H., et al., *Pharmacogenetics* 7:211–221 (1997)), its very low abundance in human liver makes it unlikely to contribute significantly to the activities of CPA or IFA in human liver. Rather, the more abundant CYP2C9 is an important catalyst of human hepatic CPA activation (Ren, S., et al., *Cancer Res.* 57:4229–4235 (1997)). Consequently, intratumoral delivery of CYP2C18, in combination with RED, should allow for the utilization of liver P450 inhibitors selectively directed at the human hepatic activators of CPA and IFA (primarily P450s 2B6 and 2C9, in the case of CPA, and P450s 3A4 and 2C9, in the case of IFA) to block liver-catalyzed prodrug activation, and thereby increase chemotherapeutic drug activation occurring within the tumor.

CYP2C9 is the most abundant CYP 2C enzyme expressed in human liver (Shimada, T., et al., *J Pharmacol Exp Ther.* 270:414–423 (1994)) and can activate CPA, and at a 3-fold lower catalytic efficiency IFA, in a yeast expression system (CYP2C9-Cys$^{144}$ allele (Chang, T. K. H., et al., *Pharmacogenetics* 7:211–221 (1997)). The CYP2C9-selective inhibitor sulfaphenazole slows the elimination of CPA in a subset of cancer patients (Faber, O. K., et al., *Br J. Clin Pharmacol.* 2:281–285 (1975)), indicating a role for CYP2C9 in hepatic metabolism of this drug. Consistent with these observations is the inventors' finding that CYP2C9 can sensitize 9L tumor cells to CPA, albeit with lower efficiency than CYP2C18 and CYP2C19, which becomes evident when the several-fold higher level 9L CYP2C9 protein expression is taken into account. While CYP2C9 is thus not the P450 gene of choice for CPA or IFA-based P450 gene therapy, it and other P450 genes (Nelson, D. R., et al., *Pharmacogenetics* 6:1–42 (1996)) should prove useful when combined with other cancer chemotherapeutic prodrugs (LeBlanc, G. A. and Waxman, D. J., *Drug Metab Rev.* 20:395–439 (1989); Goeptar, A. R., et al., *Crit. Rev. Toxicol.,* 25:25–65 (1995)).

The use of retroviruses and other viral vectors for delivery of therapeutic genes to tumor cells has become feasible with recent improvements in vector design (Feng, M., et al., *Nat Biotechnol.* 15:866–70 (1997); Heise, C., et al., *Nat. Med.* 3:639–645 (1997); Robbins, P. D., et al., *Trends Biotechnol.* 16:35–40 (1998)). Non-viral vectors, including cationic liposomes, DNA-protein complexes, non-viral T7 autogene vectors and other approaches (Chen, X., et al., *Hum Gene Ther.* 9:729–736 (1998); Nakanishi, M., *Critical Rev Ther Drug Carrier Systems* 12:263–310 (1995); Pawelek, J. M., et al., *Cancer Res.* 57:4537–4544 (1997)) have also undergone significant development and improvement in recent years, and should also be useful in this regard. Further enhancement of P450/RED gene delivery should be achieved by linking these genes using an IRES (internal ribosome entry site sequence) (Morgan, R. A., et al., *Nucleic Acids Res.* 20:1293–1299 (1992)) to achieve their coordinate expression on a bicistronic message. Alternatively, construction of a fusion gene which encodes a catalytically active P450-RED fusion protein (Fisher, C. W., et al., *Methods Enzymol.* 272:15–25 (1996)) should allow for highly efficient expression of P450 activity.

Limitations associated with comparatively low retroviral titers can, in part, be overcome by the use of more powerful promoters to ensure a high level of gene expression, coupled with the use of drugs, such as CPA, that exhibit a strong bystander cytotoxic effect. Improved retroviral packaging cell lines, such as BOSC23 cells, can be used to obtain retroviral titers of up to $10^7$ cfu/ml of culture supernatant (Pear, W. S., et al., *Proc Natl Acad Sci USA.* 90:8392–8396 (1993)). A further increase in viral titer may be achieved by growing the cells at 32° C. (Kaptein, L. C., et al., *Gene Ther.* 4.172–176 (1997); Kotani, H., et al., *Hum Gene Ther.* 5:19–28 (1994)) or following receptor-mediated, adenovirus-augmented transfection of standard retroviral producer lines (von Ruden, Y., et al., *Biotechniques* 18:484–489 (1995)). Purified retrovirus (Smiley, W. R., et al., *Hum Gene Ther.* 8:965–977 (1997)) can be administered by direct, repeated intratumoral injection, a method that can be quite effective for introduction of a cancer chemotherapeutic gene (Kondo, S., et al., *Cancer Res.* 58:962–967 (1998); Smiley, W. R., et al., *Hum Gene Ther.* 8:965–977 (1997)). If necessary, retroviral titers can be increased dramatically by pseudotyping with VSV glycoprotein G, which allows for concentration of the virus to >$10^9$ cfu/ml, and also broadens the viral host range (Burns, J. C., et al., *Proc Natl Acad Sci USA.* 90:8033–8037 (1993)). Innovative strategies to achieve tumor-selective gene expression, including transcriptional targeting, cellular targeting, and selective delivery in situ of both the prodrug and the therapeutic gene have also been described (Gunzburg, W. H., et al., *Recent Results Cancer Res.* 144:116–126 (1998); Schnierle, B. S. and Groner, B., *Gene Ther.* 3:1069–1073 (1996); Walther, W. and Stein, U., *J Mol Med.* 74:379–392 (1996)).

EXAMPLE 3

Incorporation of Bioreductive Drugs into P450/RED-Based Gene Therapy

Previous reports have shown that RED catalyzes the reductive activation of a number of bioreductive drugs, suggesting that RED may be a determinant of the sensitivity of tumor cells to the cytotoxic effects of several bioreductive drugs, including, for example, Adriamycin, mitomycin C, and tirapazamine (TPZ). The inventors have now demonstrated that bioreductive drugs can be incorporated into a P450/RED-based gene therapy strategy to kill tumor cells that might otherwise escape the cytotoxic effects of radiation or conventional chemotherapies. Furthermore, the inventors now show that the combination of a P450-activated drug with a RED-activated drug, in the context of P450/RED-based gene therapy, can lead to an increase in antitumor activity.

Many tumors, in particular solid tumors, are characterized by poor vascularization leading to regions of hypoxia (Brown, J. M. and Giaccia, A. J., *Cancer Res.* 58:1408–1416 (1998)). Since the presence of oxygen is required for the cytotoxic effects of radiation and many cancer chemotherapeutic drugs, tumor hypoxia is associated with both radiation resistance and chemoresistance. Accordingly, hypoxic tumor cells are among the most difficult to treat using conventional cancer chemotherapeutics. Since oxygen is a P450 cosubstrate that is required for all P450-catalyzed monooxygenase reactions, it is important to determine whether the low $O_2$ concentrations associated with tumor hypoxia block P450/RED-catalyzed activation of cancer chemotherapeutic drugs, such as cyclophosphamide (CPA).

In this Example, recombinant retrovirus was used to deliver the human P450 reductase (hRED) gene to 9L gliosarcoma cells transduced with the human P450 gene 2B6. The impact of this P450 and RED gene transfer combination on the chemosensitivity of the tumor cells to CPA was evaluated under both hypoxic (1% $O_2$) and non-toxic conditions (approximately 20% $O_2$). In addition, the impact of P450 together with RED gene transfer on the cytotoxicity of the bioreductive drugs Adriamycin and tirapazamine (TPZ; 3-amino-1,2,4-benzotriazine-1,4-di-N-oxide; also known as SR4233 and WIN50975) was determined. These latter studies were carried out to assess the impact of P450/RED gene transfer on the chemosensitivity of tumor cells to TPZ, both alone and in combination with the P450-activated chemotherapeutic drug CPA.

As demonstrated below, the cytotoxic activity of CPA in the context of P450/RED gene transfer was not decreased under conditions of hypoxia, indicating that both hypoxic and normoxic tumor cells are efficiently killed using the P450/RED-based chemotherapeutic drug activation gene therapy method. Moreover, the cytotoxicity of the bioreductive drugs TPZ and Adriamycin was shown to be enhanced by P450 gene transfer and by RED gene transfer, demonstrating that the P450/RED-based gene therapy method can be employed with bioreductive drugs. Finally, the combination of the P450-activated chemotherapeutic drug CPA with the RED-activated bioreductive drug TPZ was shown to lead to an increase in tumor cell cytotoxicity compared to that which was conferred by either drug alone. Thus, the efficacy of cancer gene therapy using the P450/RED drug activation system can be substantially increased by combining a P450-activated drug with a RED-activated bioreductive drug.

Materials and Methods

Chemicals: CPA and TPZ were obtained from Sigma Chemical (St. Louis, Mo.). Blasticidin S-hydrochloride was from ICN.

Construction of recombinant retroviruses: cDNA encoding HRED cloned into the Eco RI site of pUV1 (Yamano, S., et al., *Mol. Pharmacol.* 36:83–88 (1989)) was obtained from Dr. F. Gonzalez, NCI. This cDNA was subcloned into the Eco RI site of pWZL-Blast, a retroviral vector based on the pBabe series (Morgenstern, J. P. and Land, H., *Nucleic Acids Res.* 18:3587–3596 (1990)) which encodes a blasticidin resistance gene transcribed from the viral 3'-LTR. The plasmid pWZL-Blast was obtained from Dr. J. P. Morgenstern, Millenium Pharmaceuticals, Cambridge, Mass.

Construction of 9L gliosarcoma cell lines expressing human P450 reductase cDNA by retroviral infection: Transfection of the ecotropic packaging cell line BOSC23 (Pear W. S., et al., *Proc. Natl. Acad Sci. USA* 90:8392–8396 (1993)) with hRED-encoding retroviral plasmid DNA, harvesting of the retroviral supernatant, and infection of 9L gliosarcoma cells (both 9L/wild-type cells and 9L/2B6 cells) was carried out as described under Example 2. Selection of pools of blasticidin-resistant cells was accomplished using 3 µg/ml blasticidin S hydrochloride for 2 days. Drug-resistant pools of cells were propagated and then evaluated for RED enzyme activity in isolated microsomes as described under Example 2. A 5–6 fold increase RED-catalyzed cytochrome C reduction was obtained in both the 9L/hRED and the 9L/2B6/hRED pools of transfectants.

9L gliosarcoma cell lines stably expressing rat P450 2B1 and rat RED: The following rat 9L gliosarcoma transfectants were those already described in Example 1: P3 and P17, which stably express P450 gene CYP2B1; 9L-lacZ, which stably expresses the *E. coli* β-galactosidase gene; R26, which stably expresses rat RED but not P450; and PR1, PR7, PR11, which stably express rat P450 2B1 and rat RED.

Cytotoxicity assays: To evaluate the chemosensitivity of the P450- and P450/RED-expressing 9L tumor cells, cells were plated in triplicate at 4000 cells/well of a 48-well plate 18–24 hours prior to drug treatment. Cells were then treated with drugs (0 to 1 mM CPA or 0 to 50 µM TPZ, as indicated in each experiment) and placed in a tissue culture incubator maintained under hypoxic conditions (1% $O_2$, 5% $CO_2$, 94% $N_2$) or under normoxic conditions (19.6% $O_2$, 5% $CO_2$, 75.4% $N_2$) for a period of 4 days. 9L/pBabe cells, which were transduced with the empty retroviral plasmid pBabe-puro (see, Example 2), served as controls. Cells remaining after this time were quantitated using a crystal violet/alcohol-extraction assay, as described under Example 2. Data are presented as cell number relative to drug-free controls, mean±SD values for triplicate samples, unless indicated otherwise. Error bars not seen in the individual figures are too small to be visible.

Results

Retroviral Transduction of Human RED: 9L gliosarcoma cells transduced with the human P450 gene 2B6 (see Example 2) were infected with retrovirus particles engineered to express a full length HRED cDNA (Yarnano, S., et al., *Mol. Pharmacol.* 36:83–88 (1989)). The cDNA was cloned into a pBabe-based retroviral vector (Morgenstern, J. P. and Land, H., *Nucleic Acids Res.* 18:3587–3596 (1990)) that confers resistance to blasticidin, allowing for the selection of a pool of retrovirally transduced cells that express both P450 2B6 and hRED (designated 9L/2B6/hRED cells). Similarly, a pool of 9L cells transduced with HRED in the absence of P450 co-expression was obtained (9L/hRED cells).

Evaluation of the cytotoxicity of CPA toward 9L/2B6/hRED cells was carried out in comparison to 9L/2B6 cells. Under normoxic conditions (approximately 20% $O_2$), a large increase in CPA cytotoxicity was observed in response to retroviral transduction of hRED (FIG. 20A; 9L/2B6/hRed vs. 9L/2B6). No CPA cytotoxicity was observed in 9L/hRED cells or in 9L/pBabe control cells (FIG. 20A). Thus, human RED gene transfer greatly increases the chemosensitivity of a tumor cell transduced with a cytochrome P450 gene, much in the same way as was shown in Example 2 for a rat RED gene. Rat and human RED show 92% amino acid sequence identity (Yamano, S., et al., *Mol. Pharmacol.* 36:83–88 (1989)). A similar degree of sequence conservation is seen with other mammalian P450 reductases, which are expected to behave similarly in this regard.

Impact of hypoxia on P450/RED-dependent CPA cytotoxicity: To test whether the efficacy of P450/RED-based gene therapy is influenced by the hypoxic conditions found within many solid tumors, the cytotoxic effects of CPA toward 9L/2B6/hRED cells and 9L/2B6 cells were evaluated in cells treated with drug under conditions of hypoxia (1% $O_2$) FIG. 20B shows that hypoxia does not significantly alter the cytotoxicity of CPA toward 9L/2B6/RED cells or toward 9L/2B6 cells (c.f., FIG. 20A). It is concluded that the affinity of the expressed P450 protein for cellular $O_2$ is sufficiently high so that P450-catalyzed chemotherapeutic drug activation is not impaired under hypoxic conditions.

Activation of TPZ by RED and by P450 2B6: TPZ is the lead compound of a novel series of bioreductive drugs with a high specificity for hypoxic tumor cells (Boyer, M. J., *Oncol. Res.* 9:391–395 (1997)). TPZ is activated by RED by a one electron reduction that yields the TPZ nitroxide radical ("TPZ radical") (Patterson, A. V., et al., *Br. J. Cancer* 72:1144–1150 (1995); Patterson, A. V., et al., *Br. J. Cancer* 76:1338–1347 (1997)). This radical causes DNA single and double-strand breaks and has been implicated in the cytotoxicity of TPZ under hypoxic conditions (Jones, G. D. and Weinfeld, M., *Cancer Res.* 56:1584–1590 (1996); Siim, B. G., et al., *Br. J. Cancer* 73:952–960 (1996)). TPZ radical can be further converted to the inactive two electron reduction product SR4317 (3-amino-1,2,4-benzotriazine-1-oxide) either by radical disproportionation or by a second one electron reduction. Under aerobic conditions, TPZ radical is rapidly reoxidized concomitant with the conversion of molecular oxygen to superoxide radical and other reactive reduced oxygen species which mediate TPZ's cytotoxic effects under aerobic conditions (Elwell, J. H., et al., *Biochem. Pharmacol.* 54:249–257 (1997)). Mouse liver P450 enzymes can catalyze the reductive metabolism of TPZ (Riley, R. J., et al., *Biochem. Pharmacol.* 45:1065–1077 (1993)). However, the significance of this P450-catalyzed metabolism is unknown, since these earlier studies only monitored formation of the inactive, two electron reduced metabolite SR4317. Moreover, it has not been determined whether P450-catalyzed TPZ metabolism leads to formation of TPZ radical or to any enhancement of TPZ cytotoxicity.

Accordingly, the inventors investigated whether intratumoral expression of P450 2B6, with or without RED, has any effect on the cytotoxicity of TPZ toward 9L tumor cells. FIG. 21 shows, that in cells cultured under normoxic conditions, P450 2B6 expression alone has no effect on the cytotoxicity of TPZ toward control 9L tumor cells (9L/pBabe vs. 9L/2B6). By contrast, RED gene transfer, with or without P450 2B6 gene transfer, led to an increase in TPZ cytotoxicity (FIG. 21). In a similar series of experiments carried out under hypoxic culture conditions, where TPZ is intrinsically more cytotoxic than it is under normoxic conditions (c.f., 10-fold lower scale of x-axis in FIG. 22 vs. FIG. 21), RED gene transfer also chemosensitized 9L tumor cells to TPZ (FIG. 22; 9L/hRED vs. 9L/pBabe). Some enhanced cytotoxicity of TPZ toward the tumor cells was also observed when the cells were transduced with P450 2B6 retrovirus (FIG. 22; 9L/2B6 vs. 9L/pBabe). Most striking, however, was the substantial increase in cytotoxicity in tumor cells transduced with both P450 2B6 and RED (9L/2B6/hRED vs. 9L/pBabe). This finding establishes: 1) that TPZ can be activated by a P450-dependent metabolic reaction; and 2) that P450 2B6 is an active catalyst of TPZ activation under hypoxic conditions. Thus, the P450/RED gene combination substantially enhanced the tumor cell cytotoxicity of TPZ.

Enhancement of Adriamycin cytotoxicity upon co-transfer of RED with P450 to 9L tumor cells: Adriamycin (doxorubicin) is a cancer chemotherapeutic drug belonging to the anthracycline class. The cytotoxicity of Adriamycin involves several mechanisms, one of which involves bioreductive activation. Adriamycin is toxic to 9L cells in a manner that does not require P450 metabolism, as shown by the cell kill that results from exposure of either parental 9L tumor cells or 9L/lacZ-marked control cells (9L-Z) to 100 nM Adriamycin (FIG. 23). Overexpression of RED (9L cell line R26; approximately 5-fold increase in RED activity compared to 9L wild-type cells) did not enhance the cytotoxicity of Adriamycin. By contrast, a large enhancement in Adriamycin cytotoxicity was achieved by co-expression of RED with P450 2B1. Thus, a substantial increase in Adriamycin cytotoxicity was obtained when P450 and RED genes were both transferred to tumor cells.

Further augmentation of tumor cell cytotoxicity by combination of a bioreductive drug with a P450-activated prodrug: Activated CPA and activated TPZ kill tumor cells by distinct mechanisms. These involve DNA cross-linking induced by phosphoramide mustard derived from CPA, and either direct DNA strand scission (under hypoxic conditions) or DNA damage caused by reactive reduced oxygen species (under aerobic conditions), in the case of TPZ radical. While an increase in cytotoxic activity might therefore be anticipated when these two drugs are combined in treating tumor cells transduced with P450 and RED, it is alternatively possible that the competition between CPA and TPZ for metabolism by the same pair of enzymes (i.e., P450 and RED) could result in no increase, or perhaps even an overall decrease in cytotoxicity. To address this question, the cytotoxic effect of CPA in combination with TPZ was assayed in tumor cells transduced with both P450 2B6 and RED. The concentrations of TPZ used in this study, 5–10 $\mu$M for tumor cells treated under normoxic conditions, were selected to give minimal cytotoxicity toward 9L/hRED and 9L/pBabe cells (c.f, FIG. 21). FIG. 24A shows that the combination of 5 $\mu$M TPZ with CPA at concentrations ranging from 0.05 mM to 0.5 mM led to a substantial increase in antitumor activity in the case of 9L/2B6/hRED cells. This cytotoxicity was greater than that provided by CPA alone, and was readily apparent over the full range of CPA concentrations. In control experiments, TPZ at this concentration had no cytotoxicity on its own, and did not chemosensitize to CPA tumor cells that did not express P450 2B6 (i.e., 9L/hRED and 9L/pBabe cells) (FIG. 24B, 24C). FIG. 24A also shows that an additive effect of TPZ on CPA cytotoxicity can be achieved in cells exposed to a somewhat higher TPZ concentration (10 $\mu$M). Similar effects were apparent from experiments carried out under hypoxic conditions, where TPZ at a much lower concentration (0.5 to 1.5 $\mu$M) increased the sensitivity of the 9L/2B6/hRED cells to CPA (FIG. 25A). Again, this increased chemosensitivity to CPA of TPZ-treated tumor cells was dependent on P450 2B6 gene transfer (FIG. 25A vs. FIGS. 25B, 25C). Thus, significant increases in antitumor effect can be achieved under both hypoxic and normoxic conditions by the treatment of tumor cells with a P450-activated chemotherapeutic drug in combination with a bioreductive drug in the context of P450/RED-based cancer gene therapy.

Discussion

The experiments described in this Example establish that: 1) P450/RED-based cancer gene therapy is effective under both hypoxic and normoxic conditions; 2) the combination of P450 with RED gene transfer leads to enhanced bioreductive drug cytotoxicity over that provided by P450 or RED gene transfer alone, as exemplified for both TPZ and Adriamycin; and 3) an increase in P450/RED antitumor activity can be achieved by combining a P450-activated chemotherapeutic drug, such as CPA, with a bioreductive drug, such as TPZ.

The finding that P450 2B6 does not make a major contribution to TPZ cytotoxicity under normoxic conditions (FIG. 21; compare 9L/2B6 with 9L/pBabe, and 9L/2B6/hRED with 9L/hRED) is consistent with the observation that cytochrome P450-catalyzed reduction of drugs and other foreign chemicals proceeds at a much higher rate under hypoxic or anaerobic conditions compared to aerobic (normoxic) conditions (Goeptar, A. R., et al., *Crit. Rev. Toxicol.* 25:25– 65 (1995)). By contrast, RED catalyzes the one electron reduction of TPZ and other bioreductive drugs under both hypoxic and aerobic conditions. Other cancer chemotherapeutic drugs known to undergo bioreductive metabolism carried out by cytochrome P450 enzymes include various quinone-containing molecules, such as Adriamycin, mitomycin C and 2,3,5,6-tetramethylbenzoquinone (TMQ) (Goeptar, A. R., et al., *Crit. Rev. Toxicol.* 25:25–65 (1995); Goeptar, A. R., et al., *Mol. Pharmacol.* 44:1267–1277 (1993)). Since these same drugs can also be bioactivated through reduction reactions catalyzed by RED (Belcourt, M. F., et al., *Proc. Natl. Acad. Sci. USA* 93:456–460 (1996); Sawamura, A. O., *Oncology*. 53:406–411 (1996); Bartoszek, A. and Wolf, C. R., *Biochem. Pharmacol.* 43:1449–1457 (1992)), an enhanced cytotoxic response can now be expected from the combination of P450 with RED gene transfer for these and other bioreductive drugs as well. Thus, the present finding that the cytotoxicity of bioreductive drugs can be enhanced by combining P450 gene transfer with RED gene transfer extends the range of drugs that can be utilized in a P450-based cancer gene therapy strategy to include bioreductive drugs.

Bioreductive drugs constitute an important class of cancer chemotherapeutic agents with particularly strong activity against hypoxic tumor cells, which are often resistant to traditional radiation and chemotherapy treatments. The demonstration in this Example that an increase in antitumor effect was achieved by combining the P450 activated chemotherapeutic drug CPA with the bioreductive drug TPZ further extends the utility of P450-based gene therapy to include combinations of these two important classes of anticancer agents. This, in turn, extends the range of tumor cells susceptible to P450/RED-based gene therapy to include hypoxic tumor cells.

Examples of bioreductive drugs useful in such a strategy include Adriamycin, mitomycin C, tirapazamine (TPZ), and various other nitroimidazoles, nitroaromatics, quinones, aliphatic, aromatic, or heterocyclic N-oxides, or bioreducible DNA alkylators, that are capable of undergoing RED-catalyzed and/or P450-catalyzed bioreductive activation (Patterson, A. V., et al., *Br J Cancer* 72:1144–1150 (1995); Workman, P., et al., *Cancer Metastasis Rev.* 12:73–82 (1993); Goeptar, A. R., et al., *Crit. Rev. Toxicol* 25:25–65 (1995)). Although this hypoxic tumor cell strategy might seem counter-intuitive, given the requirement of oxygen for P450-catalyzed monooxygenase reactions, the studies in this Example showed no significant loss of P450-dependent prodrug activation in P450-transduced tumor cells grown under hypoxic conditions. Consequently, hypoxia response elements (O'Rourke, J. F., et al., *Oncol. Res.* 9:327–332 (1997)) may be used to achieve transcriptional targeting (Dachs, G. U., et al., *Nat Med.* 3:515–520 (1997)) of both P450 and RED genes to tumors that are characterized by a localized hypoxic environment (Brown and Giaccia, Cancer Res. 58:1408–1416 (1998)).

Combinations of cancer chemotherapeutic drugs are invariably required for effective and durable clinical responses in the cancer patient. TPZ has previously been shown to enhance the activity of CPA and other cancer chemotherapeutics in both rodent and human tumor xenograft models, however this effect does not translate into a therapeutic benefit owing to a corresponding increase in bone marrow toxicity (Lartigau, E. and Guichard, M., *Br. J. Cancer* 73:1480–1485 (1996); Siemann, D. W., *Br. J. Cancer* 74Suppl. 27:S65–69(1996)). The present demonstration that such a drug combination is effective in the context of P450/RED-based intratumoral gene transfer enables those skilled in the art to take advantage of the intrinsic benefits of the combination of a chemotherapeutic drug with a bioreductive drug, while at the same time minimizing undesirable side effects through localized drug activation without an enhancement of host toxic responses. Thus, the present demonstration that a prototypic bioreductive drug subject to RED activation can enhance the cytotoxic activity of a P450-activated chemotherapeutic drug should substantially increase the clinical effectiveness of P450/RED-based cancer chemotherapeutic regimens.

Modifications of the above-described modes for carrying out the invention that are obvious to persons of skill in medicine, genetics, molecular biology, gene therapy, immunology, pharmacology, and/or related fields are intended to be within the scope of the following claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

What is claimed is:

1. A method for killing neoplastic cells in a mammal, said method comprising:
    (a) delivering a vector to said neoplastic cells, said vector comprising the nucleotide coding sequence of a gene encoding cytochrome P450 and the nucleotide coding sequence of a gene encoding NADPH-P450 reductase (RED);
    (b) treating said neoplastic cells with a chemotherapeutic agent that is activated by the product of said cytochrome P450 gene; and
    (c) killing said neoplastic cells.

2. The method of claim 1, wherein said cytochrome P450 gene is a mammalian gene.

3. The method of claim 2, wherein said cytochrome P450 gene is P450 1A1, P450 1A2, P450 1B1, P450 2B1, P450 2B2, P450 2B4, P450 2B5, P450 2B6, P450 2B11, P450 2A6, P450 2C6, P450 2C8, P450 2C9, P450 2C11, P450 2C18, P450 2C19, P450 2D6, P450 2E1, P450 3A4, P450 3A5, P450 3A7, or P4504B1.

4. The method of claim 1, wherein said chemotherapeutic agent is cyclophosphamide, ifosfamide, dacarbazine, procarbazine, thio-TEPA, etoposide (VP-16), 4-ipomeanol, 2-aminoanthracene, or tamoxifen.

5. The method of claim 1, wherein said cytochrome P450 gene is P450 2B1, P450 2B6, or P450 2C18, and said chemotherapeutic agent is cyclophosphamide.

6. The method of claim 1, wherein said cytochrome P450 gene is P450 2B1 or P450 3A4, and said chemotherapeutic agent is ifosfamide.

7. The method of claim 1, wherein said vector is a viral vector.

8. The method of claim 7, wherein said viral vector is derived from retrovirus, adenovirus, adeno-associated virus, herpes virus, poliovirus, papillomavirus, or lentivirus.

9. The method of claim 8, wherein said viral vector is derived from retrovirus or adenovirus.

10. The method of claim 1, wherein said vector is non-viral.

11. The method of claim 10, wherein said non-viral vector is a tumor targeted bacterial vector, cationic liposome, a fusogenic liposome, a DNA-adenovirus conjugate, a DNA-protein complex, a non-viral T7 autogene vector, the direct injection of nucleic acid, particle-mediated gene transfer, receptor-mediated gene transfer, starburst polyamidoamine dendrimers, a cationic peptide, mammalian artificial chromosome, endothelial cell, or macrophage.

12. The method of claim 1, wherein said vector includes an internal ribosome entry site (IRES) sequence to achieve coordinate expression of said cytochrome P450 gene and said NADPH-P450 reductase (RED) gene.

13. The method of claim 1, wherein said cytochrome P450 nucleotide coding sequence and said NADPH-P450 reductase (RED) nucleotide coding sequence are associated in frame to encode a fusion protein.

14. The method of claim 1, further comprising treating said neoplastic cells with a bioreductive drug.

15. The method of claim 14, wherein said bioreductive drug is a nitroimidazole, a nitroaromatic, a quinone, an aliphatic, aromatic, or heterocyclic N-oxide, or a bioreducible DNA alkylator, that is capable of undergoing bioreductive activation catalyzed by cytochrome P450, NADPH-P450 reductase (RED), or both cytochrome P450 and RED.

16. The method of claim 15, wherein said bioreductive drug is Adriamycin, porfiromycin, mitomycin C, tirapazamine, indoloquinone E09, aziridinylnitroimidazole RB6145, dinitrophenylaziridine (CB1954), 2, 3, 5, 6-tetramethylbenzoquinone (TMQ), diaziquone (AZQ), the intercalator amine N-oxide AQ4N, the bioreducible DNA alkylator NSC646394 or the bioreducible DNA alkylator NSC658926.

17. The method of claim 16, wherein said bioreductive drug is tirapazamine.

18. The method of claim 1, further comprising systemically administering to said mammal an agent that will decrease the activity or expression level of hepatic P450 reductase (RED).

19. The method of claim 10, wherein said agent is an anti-thyroid drug.

20. The method of claim 19, wherein said anti-thyroid drug is methimazole or propylthiouracil.

21. The method of claim 20, wherein said anti-thyroid drug is methimazole.

22. The method of claim 1, wherein said vector further comprises the HSV-TK gene and said neoplastic cells are further treated with ganciclovir.

23. The method of claim 1, wherein said vector further comprises the bacterial cytosine deaminase (CD) gene and said neoplastic cells are further treated with 5-fluorocytosine.

24. The method of claim 1, wherein said vector further comprises a cancer therapeutic gene selected from the group consisting of tumor suppressor genes, apoptotic factor genes, and cytokine genes.

25. A method for killing neoplastic cells in a mammal, said method comprising:
 (a) delivering two vectors to said neoplastic cells; one vector comprising the nucleotide coding sequence of a gene encoding cytochrome P450, the other vector comprising the nucleotide coding sequence of a gene encoding NADPH-P450 reductase (RED);
 (b) treating said neoplastic cells with a chemotherapeutic agent that is activated by the product of said cytochrome P450 gene; and
 (c) killing said neoplastic cells.

26. The method of claim 25, wherein said vector comprising a cytochrome P450 gene and said vector comprising a RED gene are both viral vectors or both non-viral vectors.

27. The method of claim 25, wherein said vector comprising a cytochrome P450 gene and said vector comprising a RED gene are either viral or non-viral vectors.

28. The method of claim 25, wherein said cytochrome P450 gene is a mammalian gene.

29. The method of claim 28, wherein said cytochrome P450 gene is P450 1A1, P450 1A2, P450 1B1, P450 2B1, P450 2B2, P450 2B4, P450 2B5, P450 2B6, P450 2B11, P450 2A6, P450 2C6, P450 2C8, P450 2C9, P450 2C11, P450 2C18, P450 2C1 9, P450 2D6, P450 2E1, P450 3A4, P450 3A5, P450 3A7, or P450 4B1.

30. The method of claim 25, wherein said chemotherapeutic agent is cyclophosphamide, ifosfamide, dacarbazine, procarbazine, thio-TEPA, etoposide (VP-16), 4-ipomeanol, 2-aminoanthracene, or tamoxifen.

31. The method of claim 25, wherein said cytochrome P450 gene is P450 2B1, P450 2B6, or P450 2C18, and said chemotherapeutic agent is cyclophosphamide.

32. The method of claim 25, wherein said cytochrome P450 gene is P450 2B1 or P450 3A4, and said chemotherapeutic agent is ifosfamide.

33. The method of claim 25, further comprising treating said neoplastic cells with a bioreductive drug.

34. The method of claim 33, wherein said bioreductive drug is a nitroimidazole, a nitroaromatic, a quinone, an aliphatic, aromatic, or heterocyclic N-oxide, or a bioreducible DNA alkylator, that is capable of undergoing bioreductive activation catalyzed by cytochrome P450, NADPH-P450 reductase (RED), or both cytochrome P450 and RED.

35. The method of claim 34, wherein said bioreductive drug is Adriamycin, porfiromycin, mitomycin C, tirapazamine, indoloquinone E09, aziridinylnitroimidazole RB6145, dinitrophenylaziridine (CB1954), 2, 3, 5, 6-tetramethylbenzoquinone (TMQ), diaziquone (AZQ), the intercalator amine N-oxide AQ4N, the bioreducible DNA alkylator NSC646394 or the bioreducible DNA alkylator NSC658926.

36. The method of claim 35, wherein said bioreductive drug is tirapazamine.

37. The method of claim 25, further comprising systemically administering to said mammal an agent that will decrease the activity or expression level of hepatic P450 reductase (RED).

38. The method of claim 37, wherein said agent is an anti-thyroid drug.

39. The method of claim 38, wherein said anti-thyroid drug is methimazole or propylthiouracil.

40. The method of claim 39, wherein said anti-thyroid drug is methimazole.

41. The method of claim 25, wherein said vector further comprises the HSV-TK gene and said neoplastic cells are further treated with ganciclovir.

42. The method of claim 25, wherein said vector further comprises the bacterial cytosine deaminase (CD) gene and said neoplastic cells are further treated with 5-fluorocytosine.

43. The method of claim 25, wherein said vector further comprises a cancer therapeutic gene selected from the group consisting of tumor suppressor genes, apoptotic factor genes, and cytokine genes.

44. A method for killing neoplastic cells in a mammal, said method comprising:
(a) delivering a vector to said neoplastic cells, said vector comprising the nucleotide coding sequence of a gene encoding cytochrome P450 and the nucleotide coding sequence of a gene encoding NADPH-P450 reductase (RED);
(b) treating said neoplastic cells with a bioreductive drug; and
(c) killing said neoplastic cells.

45. The method of claim 44, wherein said cytochrome P450 gene is P450 1A1, P450 1A2, P450 1B1, P450 2B1, P450 2B2, P450 2B4, P450 2B5, P450 2B6, P450 2B11, P450 2A6, P450 2C6, P450 2C8, P450 2C9, P450 2C11, P450 2C18, P450 2C19, P450 2D6, P450 2E1, P450 3A4, P450 3A5, P450 3A7, or P450 4B1.

46. The method of claim 44, wherein said bioreductive drug is a nitroimidazole, a nitroaromatic, a quinone, an aliphatic, aromatic, or heterocyclic N-oxide, or a bioreducible DNA alkylator, that is capable of undergoing bioreductive activation catalyzed by cytochrome P450, NADPH-P450 reductase (RED), or both cytochrome P450 and RED.

47. The method of claim 46, wherein said bioreductive drug is Adriamycin, porfiromycin, mitomycin C, tirapazamine, indoloquinone E09, aziridinylnitroimidazole RB6145, dinitrophenylaziridine (CB1954), 2, 3, 5, 6-tetramethylbenzoquinone (TMQ), diaziquone (AZQ), the intercalator amine N-oxide AQ4N, the bioreducible DNA alkylator NSC646394 or the bioreducible DNA alkylator NSC658926.

48. The method of claim 44, wherein said cytochrome P450 gene is P450 2B6 and said bioreductive drug is tirapazamine.

49. A method for killing neoplastic cells in a mammal, said method comprising:
(a) administering to said mammal an agent that will decrease the activity or expression level of hepatic P450 reductase (RED) in said mammal;
(b) delivering a vector to said neoplastic cells, said vector comprising the nucleotide coding sequence of a gene encoding cytochrome P450 and the nucleotide coding sequence of a gene encoding RED;
(c) treating said neoplastic cells with a chemotherapeutic agent that is activated by the gene product of said cytochrome P450 gene; and
(d) killing said neoplastic cells.

50. The method of claim 49, wherein said agent that will decrease the activity or expression level of hepatic P450 reductase in said mammal is an anti-thyroid drug.

51. The method of claim 50, wherein said anti-thyroid drug is methimazole or propylthiouracil.

52. The method of claim 51, wherein said anti-thyroid drug is methimazole.

53. The method of claim 49, wherein said cytochrome P450 gene is P450 1A1, P450 1A2, P450 1B1, P450 2B1, P450 2B2, P450 2B4, P450 2B5, P450 2B6, P450 2B11, P450 2A6, P450 2C6, P450 2C8, P450 2C9, P450 2C11, P450 2C18, P450 2C19, P450 2D6, P450 2E1, P450 3A4, P450 3A5, P450 3A7, or P450 4B1.

54. The method of claim 49, wherein said chemotherapeutic agent is cyclophosphamide, ifosfamide, dacarbazine, procarbazine, thio-TEPA, etoposide (VP-16), 4-ipomeanol, 2-aminoanthracene, or tamoxifen.

* * * * *